US012778564B2

(12) United States Patent
Xie et al.

(10) Patent No.: US 12,778,564 B2
(45) Date of Patent: Nov. 3, 2026

(54) COMBINED HEMOSTATIC POWDER AND LIQUID DELIVERY DEVICES FOR CONTROLLING BLEEDING AND SEALING TISSUE AT SURGICAL SITES

(71) Applicants: GUANGZHOU BIOSEAL BIOTECH CO., LTD., Guangzhou Science City (CN); ETHICON, INC., Raritan, NJ (US)

(72) Inventors: Shiwei Xie, Guangzhou Science City (CN); Jianxin Guo, Somerville, NJ (US); Yufu Li, Raritan, NJ (US); Xuelin Guo, Piscataway, NJ (US); Samantha Weber, Cincinnati, OH (US)

(73) Assignees: Guangzhou Bioseal Biotech Co., Ltd., Guangzhou Science City (CN); Ethicon, Inc., Raritan, NJ (US)

( * ) Notice: Subject to any disclaimer, the term of this patent is extended or adjusted under 35 U.S.C. 154(b) by 181 days.

(21) Appl. No.: 18/700,441

(22) PCT Filed: Sep. 10, 2021

(86) PCT No.: PCT/CN2021/117624
§ 371 (c)(1),
(2) Date: Apr. 11, 2024

(87) PCT Pub. No.: WO2023/035216
PCT Pub. Date: Mar. 16, 2023

(65) Prior Publication Data

US 2024/0350126 A1 Oct. 24, 2024

(51) Int. Cl.
*A61B 17/00* (2006.01)

(52) U.S. Cl.
CPC .................. *A61B 17/00491* (2013.01); *A61B 2017/00495* (2013.01); *A61B 2017/00522* (2013.01)

(58) Field of Classification Search
CPC .... A61B 17/00491; A61B 2017/00495; A61B 2017/005; A61B 2017/00504;
(Continued)

(56) References Cited

U.S. PATENT DOCUMENTS 369,767 A 9/1887 Beall
3,844,284 A 10/1974 Schoenfeld et al.
(Continued)

FOREIGN PATENT DOCUMENTS

CN 201346338 Y 11/2009
EP 1955727 B1 8/2008
(Continued)

OTHER PUBLICATIONS

Nipro Corp WO 2013183476 A1 (Year: 2013).*
(Continued)

*Primary Examiner* — Kankindi Rwego
(74) *Attorney, Agent, or Firm* — David R. Crichton

(57) ABSTRACT

A combined powder and liquid delivery device includes a housing having a powder chamber and a liquid chamber. The device includes an applicator tip having a powder delivery channel extending between a proximal end and a distal end of the applicator tip that is in fluid communication with the powder chamber, and a liquid delivery channel that extends from the proximal to the distal end of the applicator tip that is in fluid communication with the liquid chamber. The delivery device includes a powder inlet port in fluid communication with the powder chamber, and a liquid inlet port in fluid communication with the liquid chamber. A powder delivery system is in fluid communication with the powder inlet port, the powder chamber, and the powder delivery channel. A liquid delivery system is in fluid communication with the liquid inlet port, the liquid chamber, and the liquid delivery channel.

13 Claims, 42 Drawing Sheets

(58) Field of Classification Search

CPC ........... A61B 2017/00508; A61B 2017/00513; A61B 2017/00517; A61B 2017/00522; A61L 24/043; A61M 2202/064; A61M 11/00; A61M 11/001; A61M 11/002; A61M 11/003; A61M 11/005; A61M 11/02; B05B 7/14; B05B 7/1422; B05B 7/1445; B05B 7/1459; B05B 7/1463; B05B 7/1468; B05B 7/1472; B05B 7/1477; B05B 7/1481; B05B 7/1486; B65D 83/14; B65D 83/384

USPC .................................................. 606/213, 214

See application file for complete search history.

(56) References Cited

U.S. PATENT DOCUMENTS

| | | | |
|---|---|---|---|
| 4,411,656 | A | 10/1983 | Cornett, III |
| 4,723,691 | A | 2/1988 | Minkevitch et al. |
| 5,957,340 | A | 9/1999 | Sawicki |
| 6,458,095 | B1 | 10/2002 | Wirt et al. |
| 6,699,229 | B2 | 3/2004 | Zinger et al. |
| 6,764,467 | B1 | 7/2004 | Roby et al. |
| 7,923,031 | B2 | 4/2011 | Moeller |
| 7,946,417 | B2 | 5/2011 | Plishka et al. |
| 7,951,108 | B2 | 5/2011 | Harper et al. |
| 7,967,779 | B2 | 6/2011 | Bertron et al. |
| 8,056,762 | B2 | 11/2011 | Wright et al. |
| 8,376,989 | B2 | 2/2013 | Rissman et al. |
| 10,183,132 | B2 | 1/2019 | Wang et al. |
| 10,507,293 | B2 | 12/2019 | Goodman et al. |
| 2003/0040701 | A1 | 2/2003 | Dalmose |
| 2010/0219200 | A1 | 9/2010 | Plishka et al. |
| 2011/0021982 | A1 | 1/2011 | Keller |
| 2011/0178495 | A1 | 7/2011 | Ji |
| 2012/0108509 | A1 | 5/2012 | Hissong et al. |
| 2014/0005636 | A1 | 1/2014 | Wang et al. |
| 2016/0074579 | A1 | 3/2016 | Ilan et al. |
| 2016/0074602 | A1 | 3/2016 | Wang et al. |
| 2021/0101162 | A1 | 4/2021 | Trezza, II et al. |
| 2021/0402106 | A1* | 12/2021 | Trexler ................. B05B 7/1413 |

FOREIGN PATENT DOCUMENTS

| | | | | |
|---|---|---|---|---|
| JP | H09182786 | A | 7/1997 | |
| JP | 2013183476 | A1 * | 12/2013 | ....... A61B 17/00491 |
| WO | 2013183476 | B2 | 12/2013 | |

OTHER PUBLICATIONS

Invitation to Pay Additional Fees, received for PCT Application No. PCT/CN2021/117624, mailed on Mar. 16, 2022, 14 pages.

International Search Report and Written Opinion, PCT/CN2021/117624, dated May 11, 2022, pp. 1-23.

* cited by examiner

COMBINED HEMOSTATIC POWDER AND LIQUID DELIVERY DEVICES FOR CONTROLLING BLEEDING AND SEALING TISSUE AT SURGICAL SITES

BACKGROUND OF THE INVENTION

Field of the Invention

The present patent application is generally related to methods and devices for sealing and/or controlling bleeding and is more specifically related to methods and devices that are capable of dispensing therapeutic powders and activation fluids that interact to control bleeding and seal wounds.

Description of the Related Art

In a wide variety of circumstances, animals, including humans, can suffer from bleeding due to wounds or during surgical procedures. In some circumstances, the bleeding is relatively minor, and normal blood clotting functions in addition to the application of simple first aid is all that is required. In other circumstances substantial bleeding can occur. These situations usually require specialized equipment and materials as well as personnel trained to administer appropriate aid.

To address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin, collagen, chitin, chitosan, starch, etc. To improve the hemostatic performance, scaffolds based on the above materials can be combined with biologically derived clotting factors, such as thrombin and fibrinogen.

The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. Several methods for forming various types of hemostats based on oxidized cellulose materials are known, whether made in powder, woven, non-woven, knit, and other forms. Currently utilized hemostatic wound dressings include knitted or non-woven fabrics comprising oxidized regenerated cellulose (ORC), which is oxidized cellulose with increased homogeneity of the cellulose fiber.

U.S. Pat. No. 7,923,031 "Haemostatic sprays and compositions" discloses a powder delivery system comprising: a chamber storing a haemostatic composition comprising dry gelatin powder having a mean particle size in the range of 30-250 micrometers and hyaluronic acid, said chamber having at least one discharge opening sized for distributing said composition.

U.S. Pat. No. 8,056,762 discloses a hand-held dispenser for dispensing a pharmaceutical product, the dispenser comprising: a housing providing a duct; a frangible membrane provided in the duct; a probe with a piercing tip mounted in the duct, the probe being arranged such that, in use, the piercing tip pierces the frangible membrane; an air compression device to compress air for expelling a pharmaceutical product through the probe; and a channel to substantially equalize the pressure in the air compression device and the pressure above the frangible membrane, wherein the frangible membrane is provided on a sheath which comprises a first larger diameter portion and a second axially spaced smaller diameter portion defining an external shoulder therebetween, and the inside surface of the duct has a corresponding internal shoulder to be engaged by the external shoulder of the sheath and an axial spacer is provided on one or both of the external and internal shoulders to maintain the channel past the engaged shoulders.

U.S. Patent Publication No. 2012/108509, entitled "Artificial Scab For Use In An Airway," discloses a bellows-type dispenser.

U.S. Patent publication No. 2011/0178495 "Internal dry powder delivery system and method thereof" discloses powder supply device that comprises a gas powder mixer providing a gas powder mixing chamber and a powder dispenser (bellow) which is screwed to the gas powder mixer and communicated with the gas powder mixing chamber therein. The hemostat powder is filled in the powder dispenser (bellow) and is adapted to be delivered via the powder delivery catheter to the site of bleeding.

U.S. Pat. No. 4,411,656 "Compressible syringe" discloses a compressible syringe comprised of a hollow body which is made compressible by bellow structures which extend the entire length of body.

U.S. Pat. No. 4,723,691 "Powder dispenser" discloses a hand-held and hand-operable powder dispenser having a container including a handle/nozzle section terminating at its discharge end in an unobstructed powder dispensing opening, a hand gripping section, and a central, flexible bellows section coupled between the handle/nozzle section and the hand-gripping section. The bellows section is adapted to be collapsed and expanded axially to serve as a pump. The inside diameters of the handle/nozzle section decrease substantially linearly and continually as a function of the length of the handle/nozzle section in a direction toward the powder dispensing opening. The ratio of the length of the handle/nozzle section to the greatest value of its inside diameter is substantially greater than 1.4.

U.S. Pat. No. 3,844,284 discloses a disposable douche comprised of a collapsible bellows forming a syringe and containing a pre-measured amount of cleansing powder and an elongated dispensing nozzle adapted to be secured to an open end of the bellows.

U.S. Pat. No. 5,957,340 "Container with surmounting bellows pump" discloses a container for storing and for positively dispelling and delivering therefrom fluid compositions contained therein, said container comprising a body defining a fluid reservoir, said body including a floor-like base, and walls extending upwardly thereof, a vertically-compressible bellows integrally formed with and surmounting said walls of said container as a coaxial extension thereof, said bellows defining an interior zone in fluid flow communication with said fluid reservoir of said container, a neck-like collar integrally formed with, and coaxial with, and mounted on said bellows at an upper limit thereof, said collar being formed with an upwardly-opening port through which said container is filled, cap-like closure means for sealing said port after introduction of a fluid composition into said reservoir, tubular conduit means including dispenser tube means integrally formed with and supported exteriorly of and radially outwardly of diametric bounds of said container for establishing fluid flow communication with said reservoir at a locale adjacent said base of said container, said conduit means projecting upwardly of said base and extending within vertical limits consistent with upper and lower bounds of said body of said container, said conduit means having a terminal discharge end, a nozzle integrally formed with said dispenser tube means at said terminal discharge end thereof, orifice means at said terminal discharge end of said conduit means for delivery of a fluid composition positively dispelled from said reservoir upon application of downwardly-directed, manually impressed compression forces to said bellows of said container, web means projecting outwardly of and extending along said wall means for connecting said wall means with said tubular conduit means for supporting and for stabilizing said conduit means; and said web means being integrally formed with said wall means and with said conduit means, and extending along an upward reach of said conduit means.

Patent Publication No. CN201346338 "Surgery styptic powder unidirectional propeller" discloses a surgery styptic powder unidirectional propeller, which belongs to a propeller structure attached to an endoscope, is used for delivering forwards styptic powder and comprises an inserted tube and a flexible drug-feeding bottle, wherein the inserted tube is butted and communicated with the flexible drug-feeding bottle; and the styptic powder is placed in the flexible drug-feeding bottle. The unidirectional propeller also comprises a unidirectional air inlet valve which is opened in the forward air inlet direction and is closed in the backward air inlet direction. The unidirectional propeller has the advantages that the unidirectional air inlet valve is combined with the inserted tube of a drug-feeding device for powder administration under the endoscope, thus effectively and quickly delivering the styptic powder to a required part, decreasing the reciprocation of the styptic powder in the inserted tube, preventing blood backflow and blockage and improving the styptic effect in the process of clinical endoscope surgery minimally invasive surgery; and biocompatible medical materials such as high density polyethylene, low density polyethylene, polypropylene, medical silicon rubber and the like are adopted to manufacture the propeller.

Reference is made to U.S. Patent publication No. 2014/0005636 "Multi-Compartment Pre-filled Mixing Syringes with Bypass" and to references cited therein; also a reference is made to commercially available Dermabond™ products and Evicel™ products.

U.S. Pat. No. 8,376,989 "Compartmented syringe" discloses a syringe, comprising: a first fluid conduit having at least two chambers for accommodating at least two substances of a plurality of substances and at least two bypasses operably coupled to the at least two chambers for enabling the at least two substances of the first fluid conduit to intermix; a second fluid conduit disposed adjacent the first fluid conduit and having at least one chamber for accommodating at least one substance of the plurality of substances; each substance being intermixable to form a discharge material for external application upon advancement of a plunger operably associated with each fluid conduit, the discharge material defined by the intermixed composition of predetermined volumes of at least two substances of the fluid conduits; and an end cap disposed on the distal end of at least one of the fluid conduits, the end cap including at least one vent and a filter, the filter in fluid communication with the at least one vent for facilitating the passage of gas from the end cap, the at least one vent defined through a wall of the end cap, the filter being disposed within the end cap and spaced from the at least one vent.

U.S. Pat. No. 7,946,417 "Curable material mixing and delivery device" discloses an apparatus and method for mixing two components and delivering the mixture to a patient. The apparatus contains a mixing chamber for mixing a liquid component and a powder component. The liquid component and powder component are mixed within the mixing chamber by rotation of a collapsible mixing element. A plunger is then advanced through the mixing chamber to force the mixture out of the mixing chamber and deliver the mixture to the patient.

U.S. Pat. No. 7,951,108 "Dual chamber mixing syringe and method for use" discloses a mixing syringe and method for using the mixing syringe are provided. The mixing syringe comprises a housing having a first compartment for containing a first component, an outer plunger having a second compartment for containing a second component, and an inner plunger. Prior to use, a seal separates the first and second components. To prepare the mixture, the seal is pierced, and the two components are mixed. The mixing syringe and its method of use are particularly suited to applications in which at least one of the mixture components is a relatively highly viscous material.

U.S. Pat. No. 7,967,779 "Powder and liquid mixing syringe" discloses a mixing syringe having a first sealed chamber containing a powder (powder housing) and a second sealed chamber containing a liquid (liquid housing). When the user needs to inject a patient, the device is held approximately upright while depressing a plunger. This motion causes a piercing element to pierce a foil seal separating the two chambers. Liquid then drops down into the powder housing. The liquid flows through a passage in a piston located in the powder housing, where it then meets the powder itself. As the user continues pressing the plunger downward, the piercer comes to rest within the piston and seals the passage through the piston, thereby locking the piercer and piston together. The device is then ready for an injection. As the plunger is further depressed, the piston expels the powder and liquid mixture through a needle.

U.S. Pat. No. 6,458,095 "Dispenser for an adhesive tissue sealant having a housing with multiple cavities" discloses a dispenser for simultaneously dispensing first and second components of an adhesive tissue sealant, wherein at least the first component is stored in the dispenser as dry powder that is dissolved prior to use by introduction of a solvent, the dispenser comprising the combination of: (a) a first container comprising a first septum at one end, an open end opposite the first septum, and a first movable plug disposed therein, the first container containing a quantity of the first component in the form of a dry powder stored between the first septum and the first movable plug; (b) a second container comprising a second septum at one end, an open end opposite the second septum, and a second movable plug disposed therein, the second container containing a quantity of the second component; (c) a housing having a pair of cavities sized and configured to receive and support the first and second containers, each cavity having a base, (d) pistons sized and configured to be received in the open ends of the first and second containers to advance the first and second movable plugs; and the housing including a manifold sized and configured to fit over and pierce the first and second septums and to afford passage of the first and second components via first and second flow paths to a nozzle from which the first and second components are dispensed to combine to form the adhesive tissue sealant, first and second piercers mounted in the manifold for piercing the first and second septums, each piercer extending through and being supported by a disk that is supported adjacent the base of said each cavity, each disk being supported a distance spaced from the base of the first and second cavities to form first and second plenums, each plenum defined by said each disk and adjacent walls of said each cavity, the first and second piercers affording passage of the first and second components to the first and second plenums.

U.S. Pat. No. 6,699,229 "Fluid transfer device" discloses a fluid transfer and mixing device for use in the aseptic intermixing of a powder component with a fluid component. The device is of a simple, compact construction that includes a first adapter that can be easily connected to a container containing the powder component and a second adapter that can be removably interconnected with the first adapter and can also be readily connected to a container containing a fluid such as a diluent to permit aseptic intermixing of the diluent with the powder. In use a conventional needleless syringe can be easily connected to the first adapter so that the mixture of the powder and diluent can be aseptically aspirated from the first container for subsequent delivery to the patient.

Patent publication JP9182786A discloses an enema syringe to enable both liquid and powder enema to be injected that consists of an injection cylinder projected on one of the ends of a bellows-like cylinder, a puncturing means provided on the injection cylinder at the internal base end part of the bellows-like cylinder, and a powder storage bag and a liquid storage bag made of a pliable material respectively arranged sequentially from the base end part side of the injection cylinder in the bellows-like cylinder.

U.S. Pat. No. 369,767 discloses a combined atomizer and syringe.

U.S. Patent publication No. 2011/0021982 "DISPENSING DEVICE WITH BYPASS" discloses a device for dispensing multiple components has a syringe housing comprising at least one storage container that is divided into at least two chambers and has a bypass arrangement, and a second storage container with or without a bypass arrangement, the syringe housing being realized as part of a double syringe or double cartridge having a double plunger and a common outlet. The bypass arrangement comprises at least two indentations.

U.S. Patent publication No. 2010/0219200 discloses an apparatus and method for mixing two components and delivering the mixture to a patient. The apparatus contains a mixing chamber for mixing a liquid component and a powder component. The liquid component and powder component are mixed within the mixing chamber by rotation of a collapsible mixing element. A plunger is then advanced through the mixing chamber to force the mixture out of the mixing chamber and deliver the mixture to the patient.

U.S. Patent publication No. 2003/0040701 "Dual chamber syringe with a dual function piston" discloses a dual chamber syringe in which a dual function piston divides the syringe into two compartments containing powder or fluid in one compartment and fluid in the other. For mixture of the two substances, a passage is opened between the two compartments before or during retraction of the piston to force the substances to be mixed in the front compartment. During forward movement of the piston, the passage between the two compartments is closed to force the mixture of substances through the discharge opening of the syringe.

U.S. Pat. No. 10,183,132, assigned to Ethicon LLC, the disclosure of which is hereby incorporated by reference herein, teaches an integrated delivery device that is operable with one hand and provides co-delivery of a liquid medicant and a powder medicant onto a tissue or wound from a liquid medicant expression subunit and a powder medicant expression subunit. Each expression subunit has an actuator for the liquid medicant and the powder medicant contained therein, which are positioned near one other at proximal ends of the expression subunits and delivery cannulas for each of the said expression subunits that positioned near one other at distal ends of the expression subunits.

U.S. Pat. No. 10,507,293 to Goodman et al., assigned to Ethicon, Inc. of Somerville, New Jersey, the disclosure of which is hereby incorporated by reference herein, teaches a device for the expression of a hemostatic powder. The device has an elongated reservoir with a manual air pump, such as a bellows, at a proximal end and an expression port at a distal end. A porous filter is slidably disposed within the reservoir between the bellows and plunger and the expression port, and a spring is disposed within the reservoir between the air pump and the plunger. The powder is disposed within the reservoir between the porous filter and the expression port, and the pump is in a fluid communication with the expression port through the porous filter and through the powder.

Despite the above advances, there remains a continuing need for improved devices for delivering powders and liquids for sealing tissue and/or controlling bleeding.

SUMMARY OF THE INVENTION

In one embodiment, a combined powder and liquid delivery device configured for dispensing a powder (e.g., a therapeutic powder; a hemostatic powder) and a liquid that activates the powder to form a sealing gel.

In one embodiment, the combined powder and liquid delivery device preferably includes a delivery device housing having a first chamber that is configured to hold the powder and a second chamber that is configured to hold the liquid.

In one embodiment, each chamber may have separate ports for conveniently loading the powder and the liquid into the respective chambers.

In one embodiment, the chambers may be pre-filled with the powder and the liquid.

In one embodiment, the combined powder and liquid delivery device preferably includes a powder delivery system that delivers the powder through a delivery channel or lumen to a surgical site. In one embodiment, the powder delivery system preferably includes a manual actuator (e.g., a bellows) for dispensing the powder.

In one embodiment, when the manual actuator is activated (e.g., the bellows is pushed), the air stream generated by the manual actuator carries and delivers the powder through the powder delivery channel to the surgical site.

In one embodiment, a liquid delivery system may be used for delivering the liquid (e.g., activation fluid, saline solution) to activate the powder for forming a tissue sealing gel. In one embodiment, the liquid delivery system may include one of more components of a syringe such as a syringe barrel that holds a liquid and a syringe plunger that may be depressed for dispensing the liquid from the syringe barrel. In one embodiment, the liquid may be sprayed as a fine mist over a powder layer that has been dispensed onto tissue or a wound at the surgical site.

In one embodiment, the combined powder and liquid delivery device may include an applicator tip having a bi-lumen cannula with separate the delivery channels for the powder and the liquid.

In one embodiment, the applicator tip may have a tri-lumen cannula construction including a first lumen for delivering the powder, a second lumen for delivering the liquid, and a third lumen that contains a malleable wire that enables a user to change the angle of the distal end of the applicator tip for accessing a variety of surgical sites. In one embodiment, the malleable wire enables surgeons to selectively angulate the dispensing tip to various angles relative to the elongated shaft of the applicator tip.

In one embodiment, a combined powder and liquid delivery device may have a dual lumen dispensing tip that enables both powder dispensing and liquid spraying from the same dual lumen dispensing tip. In one embodiment, the liquid exit (e.g., a liquid spray exit) and the powder dispensing exit may be staggered relative to one another to prevent the liquid from entering the powder dispensing channel. In one embodiment, the liquid exit is preferably located downstream to the powder exit to prevent the liquid from entering the powder dispensing channel.

In one embodiment, the combined powder and liquid delivery device is configured so that the powder and the liquid may be applied sequentially (e.g., first the power is delivered and then the liquid is sprayed onto a powder layer) or simultaneously (e.g., the powder and the liquid are delivered to a surgical site at the same time). In one embodiment, a combined powder and activation liquid applicator may single-handedly apply powder and liquid to a surgical site, sequentially or simultaneously.

In one embodiment, for sequential application, a layer of powder may be applied onto the surgical site, followed by the spray of liquid (e.g., activation fluid, saline solution) over the powder layer to form a tissue sealing gel layer.

In one embodiment, for simultaneous application, the powder and the liquid may be applied by pushing the bellows and the syringe plunger at the same time.

In one embodiment, a one-way valve may be in the powder delivery channel, such as between a powder reservoir and the applicator tip, to prevent moist air in the surgical site being sucked back into the powder reservoir. The presence of the one-way valve eliminates the possibility of moist air entering the powder reservoir and activating the powder while it is located inside the powder reservoir. The presence of the one-way valve also preferably eliminates the possibility of fine liquid/water droplets being sucked into the powder delivery channel and causing clogging of the powder delivery channel due to a premature powder/liquid reaction.

In one embodiment, a combined powder and liquid delivery device preferably provides powder dose control. In one embodiment, the dose control may be achieved by storing a certain amount of powder (i.e., a dose) in the powder delivery channel by the sucking action of the bellows when the bellows returns to an extended position.

In one embodiment, the powder is a therapeutic powder that may be used to control bleeding at surgical sites and to seal wounds.

In one embodiment, the powder may be a composite of fibrinogen and thrombin powders that are agglomerated with ORC fibers to allows for fast dissolution and gel formation to stop bleeding and seal tissue surfaces.

In one embodiment, a ready-to-use powder (e.g., a hemostatic powder) may be dispensed onto the sealing surface of a lung to form a highly adherent gel sealing layer. The powder may be sprayed with an activation fluid (e.g., saline solution) to accelerate gel formation.

In one embodiment, multiple layers of the powder may be applied to improve efficacy.

In one embodiment, the powder may have a density of about 0.20~0.25 g/cm3.

In one embodiment, the powder may have a particle size of <355 um.

In one embodiment, the powder may be supplied in a reservoir (e.g., a vial bottle).

In one embodiment, a powder vial may contain about 1-2 grams of powder and more specifically about 1.2 grams of powder.

In one embodiment, a vial bottle may have a size of about 10 ml.

In one embodiment, a vial bottle may have a seal that may be removed and/or pierced for dispensing the powder. In one embodiment, the seal may include a removeable foil tip or a septum top.

In one embodiment, the vial bottle may be made of glass or polymer materials (e.g., plastic).

In one embodiment, the ratio of the powder and the liquid that is delivered from the applicator tip is preferably about Ig of powder: 2.5 ml liquid.

In one embodiment, a combined powder and liquid delivery device preferably includes a delivery device housing having a powder chamber and a liquid chamber. The powder and liquid chambers are preferably isolated from one another.

In one embodiment, a combined powder and liquid delivery device preferably includes an applicator tip having a powder delivery channel extending between a proximal end and a distal end of the applicator tip that is in fluid communication with the powder chamber.

In one embodiment, the applicator tip preferably has a liquid delivery channel that extends from the proximal end to the distal end of the applicator tip that is in fluid communication with the liquid chamber.

In one embodiment, a combined powder and liquid delivery device preferably includes a powder inlet port that is in fluid communication with the powder chamber, and a liquid inlet port that is in fluid communication with the liquid chamber.

In one embodiment, the combined powder and liquid delivery device preferably includes a powder delivery system in fluid communication with the powder inlet port, the powder chamber, and the powder delivery channel.

In one embodiment, the combined powder and liquid delivery device preferably includes a liquid delivery system in fluid communication with the liquid inlet port, the liquid chamber, and the liquid delivery channel.

In one embodiment, the combined powder and liquid delivery device preferably includes a powder vial connector secured to the delivery device housing, the powder vial including the powder inlet port.

In one embodiment, the combined powder and liquid delivery device preferably includes a liquid vial connector secured to the delivery device housing, the liquid vial including the liquid inlet port.

In one embodiment, the combined powder and liquid delivery device preferably includes a powder vial coupled with the powder vial connector. The powder vial preferably has an opening that is in fluid communication with powder inlet port.

In one embodiment, the combined powder and liquid delivery device preferably includes a liquid vial coupled with the liquid vial connector. The liquid vial preferably has an opening that is in fluid communication with the liquid inlet port.

In one embodiment, a powder is disposed inside the powder vial, and a liquid is disposed inside the liquid vial.

In one embodiment, the powder may include a hemostatic powder and the liquid may include an activation fluid (e.g., saline solution) that activates the hemostatic powder to form a sealing gel for sealing tissue or controlling bleeding.

In one embodiment, the powder delivery system is moveable between a depressed configuration and an extended configuration. In one embodiment, when moving from the depressed configuration to the extended configuration the powder delivery system generates a vacuum within the powder chamber for drawing a dose of powder from the powder vial into the powder chamber. In one embodiment, when moving from the extended configuration to the depressed configuration the powder delivery system generates positive pressure within the powder chamber for expressing the dose of powder from the powder chamber and forcing the powder to flow into the powder delivery channel.

In one embodiment, the liquid delivery system is moveable between a depressed configuration and an extended configuration. In one embodiment, when moving from the depressed configuration to the extended configuration the liquid delivery system generates a vacuum within the liquid chamber for drawing a dose of liquid from the liquid vial into the liquid chamber. In one embodiment, when moving from the extended configuration to the depressed configuration the liquid delivery system generates positive pressure within the liquid chamber for expressing the dose of liquid from the liquid chamber and forcing the liquid to flow into the liquid delivery channel.

In one embodiment, the combined powder and liquid delivery device preferably includes a dual-lumen powder and liquid connector that may be secured to the distal end of the applicator tip. In one embodiment, the dual-lumen powder and liquid connector desirably has a powder exit opening in fluid communication with the powder delivery channel, and a liquid spray opening in fluid communication with the liquid delivery channel.

In one embodiment, the powder exit opening, and the liquid spray opening are staggered from one another. In one embodiment, the liquid spray opening is located downstream of the powder exit opening for preventing moisture in the liquid delivery channel from entering the powder delivery channel.

In one embodiment, the combined powder and liquid delivery device preferably includes a one-way valve located downstream of the powder chamber, which is in fluid communication with powder delivery system.

In one embodiment, the one-way valve is disposed within the powder delivery channel and is located between the powder chamber and the proximal end of the applicator tip. In one embodiment, when negative pressure is present in the powder chamber for drawing powder into the powder chamber, the one-way valve prevents moisture or liquid from being drawn into the powder chamber. In one embodiment, the one-way valve may include a ball that is free to move toward the proximal end of the delivery device under negative pressure and is free to move toward the distal end of the delivery device under position pressure.

In one embodiment, the powder delivery system may include a first air inlet in fluid communication with the powder chamber and a one-way valve disposed in the first air inlet that enables ambient air to be drawn into the powder chamber as the powder delivery system moves from the depressed configuration to the extended configuration.

In one embodiment, the liquid delivery system may include a second air inlet in fluid communication with the liquid chamber and a one-way valve disposed in the second air inlet that enables ambient air to be drawn into the liquid chamber as the liquid delivery system moves from the depressed configuration to the extended configuration.

In one embodiment, the liquid delivery system may include a first one-way valve disposed within the liquid inlet port that enables the liquid to be drawn from the liquid vial into the liquid chamber of the delivery device housing.

In one embodiment, the liquid delivery system may include a second one-way valve disposed within the liquid delivery channel and downstream of the first one-way valve disposed within in the liquid inlet port that enables the liquid in the liquid chamber to flow downstream into the liquid delivery channel.

In one embodiment, the powder delivery system preferably includes a bellows assembly having threads for releasably securing the bellows assembly to a proximal end of the delivery device housing. In one embodiment, the bellows assembly is configured for being unscrewed and released from the delivery device housing for enabling powder to be loaded into the powder chamber.

In one embodiment, the proximal end of the delivery device housing preferably has an access opening for providing access to the powder chamber. In one embodiment the access opening has internal threads that are configured to mesh with the threads of the bellows assembly for securing the bellows assembly to the proximal end of the delivery device housing.

In one embodiment, the powder chamber may be surrounded by a tube-shaped wall having a closed distal end. In one embodiment, the closed distal end has a distal exit opening formed therein that provides fluid communication between the powder chamber and the powder delivery channel.

In one embodiment, the combined powder and liquid delivery device preferably includes in anti-compaction wall disposed inside the powder chamber that is spaced away from the closed distal end of the tube-shaped wall. In one embodiment, the anti-compaction wall is located between the closed distal end of the tube-shaped wall and a proximal end of the powder chamber. In one embodiment, the anti-compaction wall has an outer perimeter that is spaced away from an inner surface of the tube-shaped wall that surrounds the powder chamber.

In one embodiment, the bellows assembly may include an end cap disposed in the access opening of the delivery device housing, a bellows projecting from a proximal face of the end cap, an elongated shaft projecting from a distal face of the end cap, whereby the distal end of the elongated shaft is disposed inside the powder chamber and opposes a proximal face of the anti-compaction wall, a filter holder mounted on the elongated shaft between the end cap and the distal end of the elongated shaft, a filter mounted on the filter holder between the filter holder and the distal end of the elongated shaft, and a compression spring extending between the bellows and the filter holder, the compression spring having a proximal end disposed inside the bellows and a distal end located adjacent a proximal face of the filter holder.

In one embodiment, when the bellows is depressed toward the distal end of the powder chamber, the compression spring is compressed so that the distal end of the compression spring urges the filter holder and the filter to move closer to the anti-compaction wall.

In one embodiment, the filter holder and the filter are configured to move simultaneously with one another within the powder chamber. In one embodiment, the filter holder and the filter have respective outer diameters that match an inner diameter of the tube-shaped wall that surrounds the powder chamber for forming an air-tight seal between the respective outer diameters of the filter holder and the filter and the inner surface of the tube-shaped wall that surrounds the powder chamber.

In one embodiment, a combined powder and liquid delivery device preferably includes a delivery device housing having a powder chamber and a liquid chamber that is isolated from the powder chamber.

In one embodiment, the delivery device preferably includes an applicator tip having a powder delivery channel extending between a proximal end and a distal end of the applicator tip that is in fluid communication with said powder chamber.

In one embodiment, the applicator tip preferably has a liquid delivery channel that extends from the proximal end to the distal end of the applicator tip that is in fluid communication with the liquid chamber.

In one embodiment, the delivery device preferably includes a powder inlet port in fluid communication with the powder chamber and a liquid inlet port in fluid communication with the liquid chamber.

In one embodiment, the delivery device desirably includes a powder delivery system in fluid communication with the powder inlet port, the powder chamber, and the powder delivery channel.

In one embodiment, the delivery device desirably includes a liquid delivery system in fluid communication with the liquid inlet port, the liquid chamber, and the liquid delivery channel.

In one embodiment, the liquid delivery system is moveable between a depressed configuration and an extended configuration.

In one embodiment, when moving from the depressed configuration to the extended configuration the liquid delivery system generates a vacuum within the liquid chamber for drawing a dose of liquid into the liquid chamber.

In one embodiment, when moving from the extended configuration to the depressed configuration the liquid delivery system generates positive pressure within the liquid chamber for expressing the dose of liquid from the liquid chamber and forcing the liquid to flow into the liquid delivery channel.

In one embodiment, a powder vial assembly for delivery powder to a combined powder and liquid delivery device preferably includes a powder housing having a proximal end, a distal end, an outer wall extending between the proximal and distal ends, a proximal opening located at the proximal end of the powder housing, and a powder dispensing opening located at the distal end of the powder housing.

In one embodiment, the powder vial assembly preferably includes a fixed guide disposed within the powder housing and secured to an inner surface of the outer wall adjacent the proximal end of the powder housing.

In one embodiment, the powder vial assembly preferably includes an actuator assembly disposed within the fixed guide, the actuator assembly including a knob that is accessible at the proximal end of powder housing and a guide shaft that extends distally between the knob and the distal end of the powder housing.

In one embodiment, the powder vial assembly desirably includes an air inlet extending though the actuator assembly that is in fluid communication with the powder dispensing opening, and a one-way valve (e.g., a one-way duck bill valve) disposed within the air inlet.

In one embodiment, the powder vial assembly desirably includes a filter carriage mounted on the guide shaft of the actuator assembly and being configured for sliding over the guide shaft toward the distal end of the powder housing.

In one embodiment, a filter is mounted on the filter carriage between the filter carriage and the distal end of the powder housing. The filter is desirably configured for sliding simultaneously with the filter carriage toward the distal end of the powder housing.

In one embodiment, a compression spring is mounted on the guide shaft of the actuator assembly. In one embodiment, the compression spring preferably has a proximal end in contact with the actuator assembly and a distal end in contact with the filter carriage for urging the filter carriage and the filter toward the distal end of the powder housing.

In one embodiment, the actuator assembly is moveable between a locked position in which the filter carriage is coupled with the fixed guide for preventing the filter carriage from moving toward the distal end of the powder housing and an unlocked position in which the filter carriage is uncoupled from the fixed guide for enabling the compression spring to urge the filter carriage and the filter to slide in a distal direction over the guide shaft toward the distal end of the powder housing.

In one embodiment, the fixed guide may include a stop, and the filter carriage may include one or more hooks that are in contact with the stop of the fixed guide when the actuator assembly is in the locked position. In one embodiment, the one or more hooks of the filter carriage are uncoupled from the stop of the fixed guide when the actuator assembly is in the unlocked position.

In one embodiment, the powder vial assembly may include a powder chamber located inside the powder housing between the filter and the powder dispensing opening. A powder may be packed into the powder chamber.

In one embodiment, a filter carriage guide shaft support may be located inside the powder housing adjacent the powder dispensing opening for supporting a distal end of the guide shaft.

In one embodiment, the actuator assembly preferably includes a pair of actuating legs for engaging and rotating the filter carriage to uncouple the filter carriage from the fixed guide. In one embodiment, the actuator assembly preferably includes a rotatable knob that may be rotated about a longitudinal axis of the guide shaft. The actuating legs are preferably coupled with the rotatable knob and rotate simultaneously with the rotatable knob.

In one embodiment, the distal ends of the actuating legs may include hooks for axially locking the actuator assembly to the fixed guide.

In one embodiment, the actuator assembly preferably includes an air inlet opening that extends therethrough, and air channels that are in communication with the air inlet opening. The air channels may be located adjacent a proximal end of the guide shaft for the filter carriage. The air inlet enables air to be drawn into the proximal end of the powder vial housing for dispensing powder via the powder dispensing opening.

In one embodiment, the distal end of the guide shaft preferably includes a compressible structure that may be compressed for installing (e.g., mounting) the filter carriage onto the guide shaft. In one embodiment, the distal end of the guide shaft preferably includes a step (e.g., an annular step) that functions as a stop for preventing the filter carriage from sliding off of the distal end of the guide shaft after the filter carriage has been mounted on the guide shaft.

In one embodiment, may be beneficial to use the powder vial assembly disclosed herein when the powder that is disposed within the powder vial housing is not very flowable.

In one embodiment, the powder vial assembly may be effectively operated in any orientation so that it is capable of dispensing powder through the powder dispensing opening when the powder and liquid delivery device is held in any orientation (e.g., upright, inverted, vertical, horizontal, sideways, angled, etc.).

In one embodiment, the filter carriage is initially locked onto the fixed guide while the compression spring is in a compressed state and has energy stored therein.

In one embodiment, users may fill the powder chamber with powder via the proximal opening located at the proximal end of the powder vial housing. In one embodiment, the powder vial assembly may be pre-filled with powder (e.g., at the factory) prior to being shipped to an end user.

In one embodiment, the knob of the actuator assembly may be rotated for turning the actuator legs, which, in turn rotate the filter carriage for uncoupling the hooks of the filter carriage from the stop of the fixed guide so that the compression spring can urge the filter carriage to slide toward the distal end of the filter carriage guide shaft.

In one embodiment, the stop of the fixed guide has axially extended slots that are used for uncoupling the filter carriage from the fixed guide. In one embodiment, upon rotating the rotatable knob of the actuator assembly, the actuating legs of the actuator assembly engage the hooks of the filter carriage for rotating the hooks into alignment with the axially extending slots of the stop, whereupon the compressed spring forces the filter carriage to slide distally over the guide shaft, which, in turn, pushes the powder in the powder chamber toward the dispensing opening of the powder vial housing.

In one embodiment, the inner surface of the outer wall of the powder vial housing preferably includes one or more surfaces (e.g., slots or pads) that engage a corresponding structure (e.g., an inverse structure) on an outer surface of the fixed guide to prevent rotation of the fixed guide relative to the powder vial housing.

In one embodiment, the inner surface of the powder vial housing has internal locking features that engage an outer surface of the fixed guide for axially locking the position of the fixed guide relative to the powder vial housing so that the fixed guide does not wove axially relative to the powder vial housing.

In one embodiment, the distal end of the powder vial housing preferably includes an internal support (e.g., a support ring) that is configured for engaging a distal end of the filter carriage guide shaft for supporting and stabilizing the guide shaft inside the powder vial housing.

In one embodiment, the filter carriage has a proximally extending hub that is adapted to engage a distal end of the compression spring.

In one embodiment, the filter carriage has a distally extending hub that is adapted to seat the filter. The filter carriage may include a stop ring located at the distal end of the distally extending hub for holding the filter on the distally extending hub after the filter has been mounted onto the filter carriage.

In one embodiment, the filter carriage preferably includes one or more hooks that project toward the proximal end of the powder vial housing for coupling the filter carriage with the fixed guide.

In one embodiment, the proximal end of the fixed guide preferable includes one or more anti-rotation components (e.g., slots, pads) that engage corresponding structure at the proximal end of the powder vial housing for preventing the fixed guide from rotating relative to the powder vial housing.

In one embodiment, the proximal end of the fixed guide may include structure (e.g., an annular projection) that engages an inner surface of the powder housing at the proximal end of the powder housing for preventing axial movement of the fixed guide relative to the powder vial housing.

In one embodiment, the distal end of the fixed guide may include a stop that engages the hooks of the filter carriage for locking the filter carriage to the fixed guide.

In one embodiment, the stop on the fixed guide desirably includes one or more axially extending slots that may be used for uncoupling the hooks of the filter carriage from the stop of the fixed guide. In one embodiment, the hooks of the filter carriage are rotated into alignment with the slots of the stop for uncoupling the filter carriage from the fixed guide, whereupon the potential energy stored in the compression spring will urge the filter carriage (and the filter) to slide toward the distal end of the guide shaft.

These and other preferred embodiments of the present patent application will be described in more detail herein.

DETAILED DESCRIPTION OF PREFERRED EMBODIMENTS

Figure 1A:
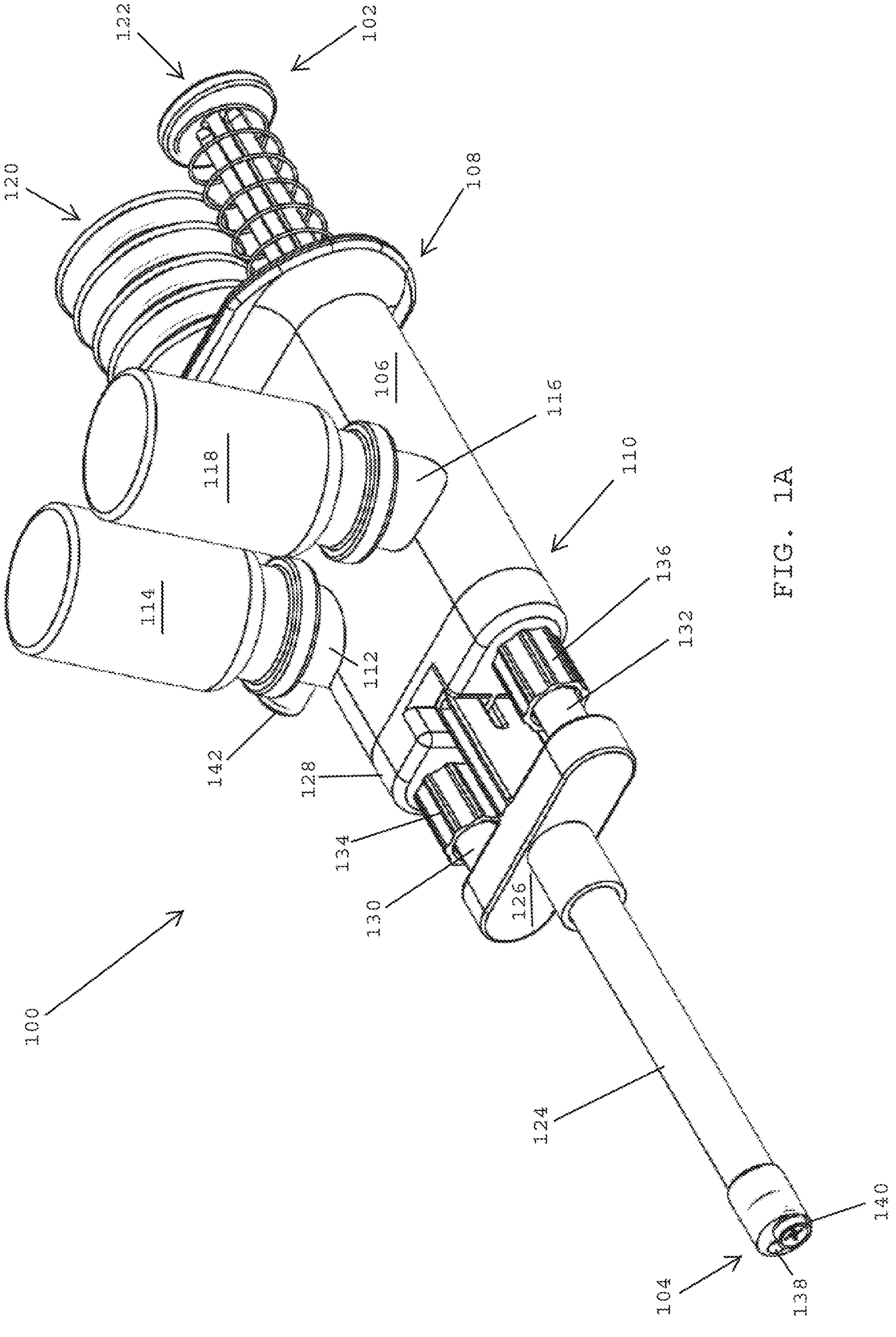
FIG. 1A is a perspective view of a combined powder and liquid delivery device, in accordance with one embodiment of the present patent application.
Figure 1B:
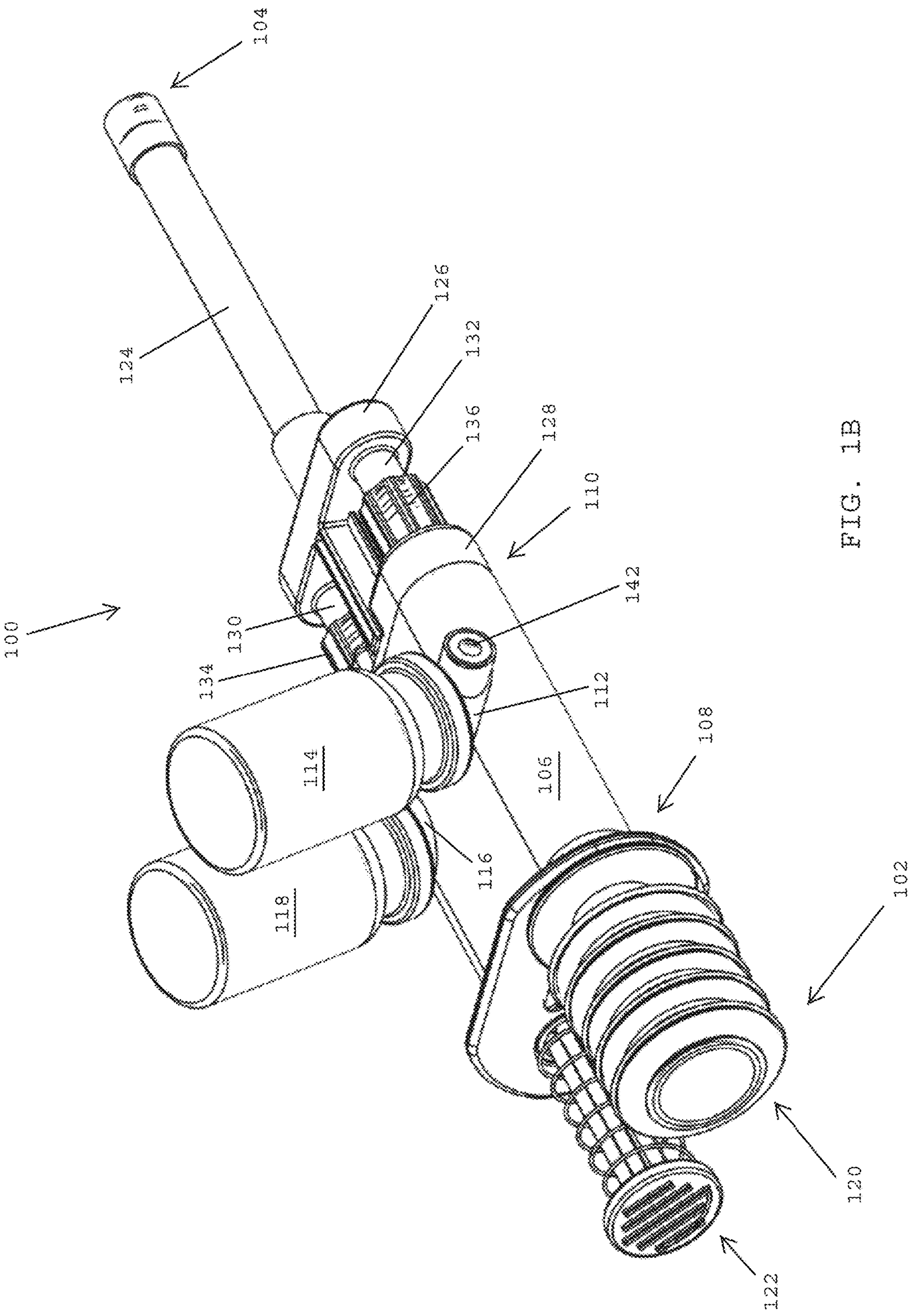
FIG. 1B is another perspective view of the combined powder and liquid delivery device shown in FIG. 1A.
Figure 1C:
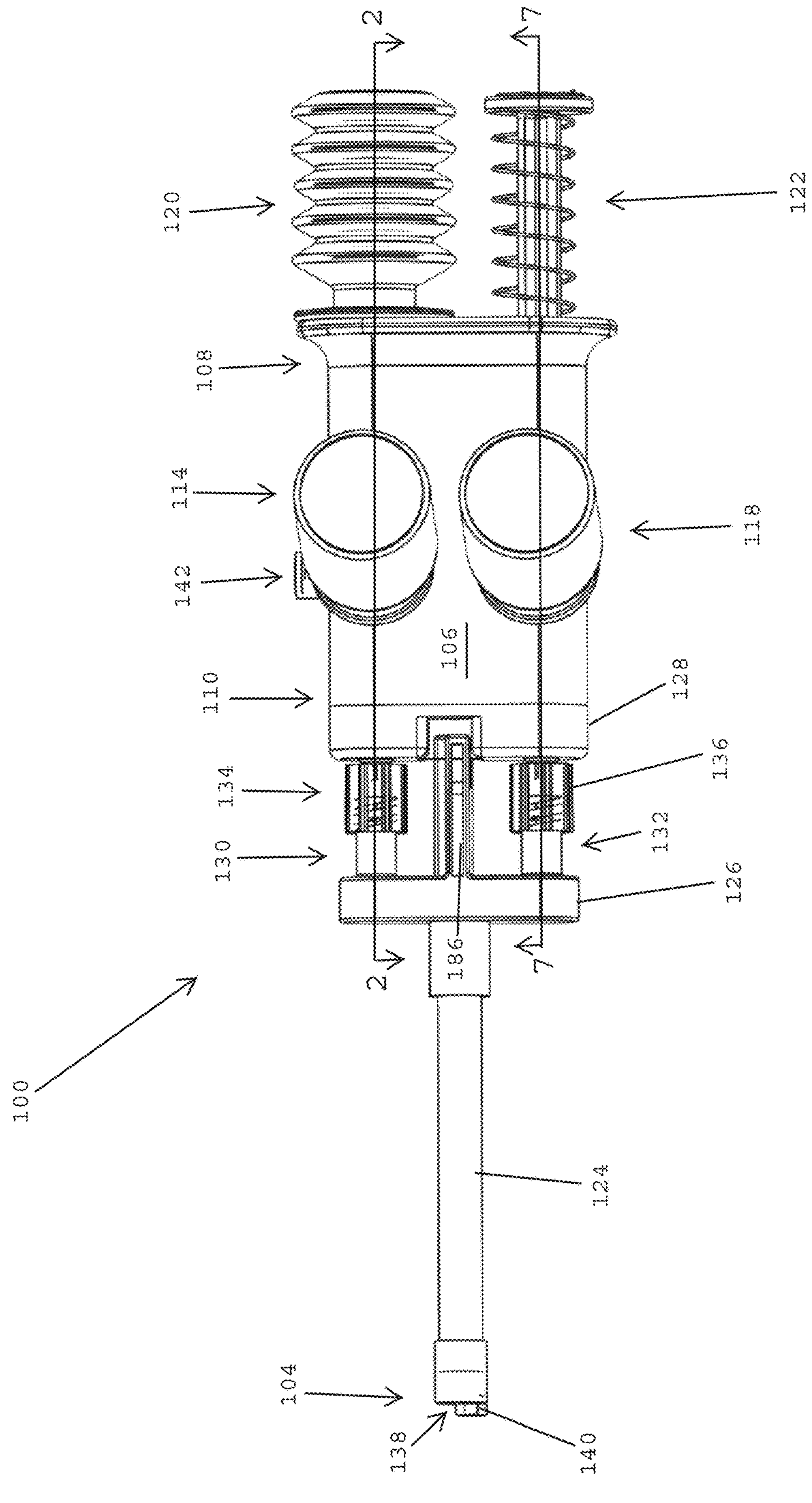
FIG. 1C is a top view of the combined powder and liquid delivery device shown in FIGS. 1A and 1B.

Referring to FIGS. 1A-ID, in one embodiment, a combined powder and liquid delivery device 100 is configured for delivering a powder (e.g., a hemostatic powder) and a liquid (e.g., activation fluid, saline solution) to a surgical site. In one embodiment, the combined powder and liquid delivery device has a proximal end 102 that is generally positioned closer to a surgeon and a distal end 104 that is generally positioned further away from the surgeon. The powder and the liquid are preferably dispensed from the distal end 104 of the combined powder and liquid delivery device 100.

In one embodiment, the combined powder and liquid delivery device 100 preferably includes a delivery device housing 106 having a proximal end 108 and a distal end 110. In one embodiment, the delivery device housing 106 preferably includes a first vial connector 112 adapted to connect a first vial 114 (e.g., a vial containing a hemostatic powder) to the delivery device housing 106.

In one embodiment, the delivery device housing 106 preferably includes a second vial connector 116 that is adapted to connect a second vial 118 (e.g., a vial containing a liquid such as a saline solution) to the device housing 106. In one embodiment, the powder is dispensed onto tissue and the liquid is sprayed onto the powder to activate the powder to form a sealing layer of a hemostatic material.

In one embodiment, the combined powder and liquid delivery device 100 preferably includes a powder delivery system 120 that is connected to a proximal end 108 of the delivery device housing 106. In one embodiment, the powder delivery system 120 is preferably configured for drawing a dose of a powder from the first vial 114, whereupon the dose of powder is directed into a powder chamber of the delivery device housing 106. The powder delivery system 120 may be activated for delivering the dose of the powder from the powder chamber to the distal end 104 of the combined powder and liquid delivery device 100.

In one embodiment, the combined powder and liquid delivery device 100 preferably includes a liquid delivery system 122 that is connected to the proximal end 108 of the delivery device housing 106. In one embodiment, the liquid delivery system 122 is preferably configured for drawing a dose of a liquid from the second first vial 118 into a liquid chamber of the delivery device housing 106 and delivering the dose of the liquid from the distal end 104 of the combined powder and liquid delivery device 100.

In one embodiment, the powder that is delivered from the distal end 104 of the combined powder and liquid delivery device 100 is preferably dispensed onto tissue or a wound to form a powder layer and the liquid is sprayed onto the dispensed powder layer for transforming the powder into a hemostatic layer (e.g., a sealing gel) that seals the tissue or the wound.

In one embodiment, the combined powder and liquid delivery device 100 preferably includes an applicator tip 124 that is configured for delivering the powder and the liquid from the distal end 104 of the combined powder and liquid delivery device 100. In one embodiment, the applicator tip 124 preferably includes an applicator tip base 126 that is utilized for connecting a proximal end of the applicator tip 124 to an applicator tip connector 128, which, in turn, is secured to the distal end 110 of the delivery device housing 106. In one embodiment, applicator tip base 126 preferably includes a powder connector 130 for connecting the applicator tip base 126 to the applicator tip connector 128, and a liquid connector 132 for connecting the applicator tip base 126 to the applicator tip connector 128. In one embodiment, the applicator tip 124, the applicator tip base 126, the powder connector 130 and the applicator tip connector 128 preferably have a powder channel (not shown) extending therethrough that is configured for delivering the powder to the distal end 104 of the applicator tip 124. In one embodiment, the applicator tip 124, the applicator tip base 126, the liquid connector 132 and the applicator tip connector 128 preferably define a liquid channel (not shown) for delivering the liquid to the distal end 104 of the applicator tip 124.

In one embodiment, the combined powder and liquid delivery device 100 preferably includes a first connecting collar 134 that is adapted for connecting the powder connector 130 with the applicator tip connector 128. In one embodiment, the combined powder and liquid delivery device 100 preferably includes a second connecting collar 136 that is adapted for connecting the liquid connector 132 with the applicator tip connector 128.

In one embodiment, the distal end 104 of the applicator tip 124 preferably includes a powder delivery opening 138 (FIGS. 1A and 1D) that is adapted for delivering the powder (e.g., a hemostatic powder) from the distal end 104 of the combined powder and liquid delivery device. 100. In one embodiment, the combined powder and liquid delivery device 100 preferably includes a liquid spray cap 140 that is connected to the distal end of the applicator tip 124 for spraying the liquid from the distal end 104 of the delivery device 100. In one embodiment, the liquid spray cap 140 is preferably located downstream from the powder delivery opening 138 so that the moisture present in the liquid is not drawn into the powder delivery opening 138, which could clog the powder channel as the powder moves distally through the applicator tip 124.

In one embodiment, the combined powder and liquid delivery device 100 preferably includes a one-way valve 142 that is in communication with the first vial connector 112 and the powder delivery system 120 for enabling ambient air to be drawn into the delivery device housing 106 and the powder delivery system 120. As will be described in more detail herein, the ambient air that is drawn into the powder delivery system is used for pulling a dose of powder from the first vial 114 and delivering the dose of the powder from the distal end 104 of the combined powder and liquid delivery device 100.

Figure 2:
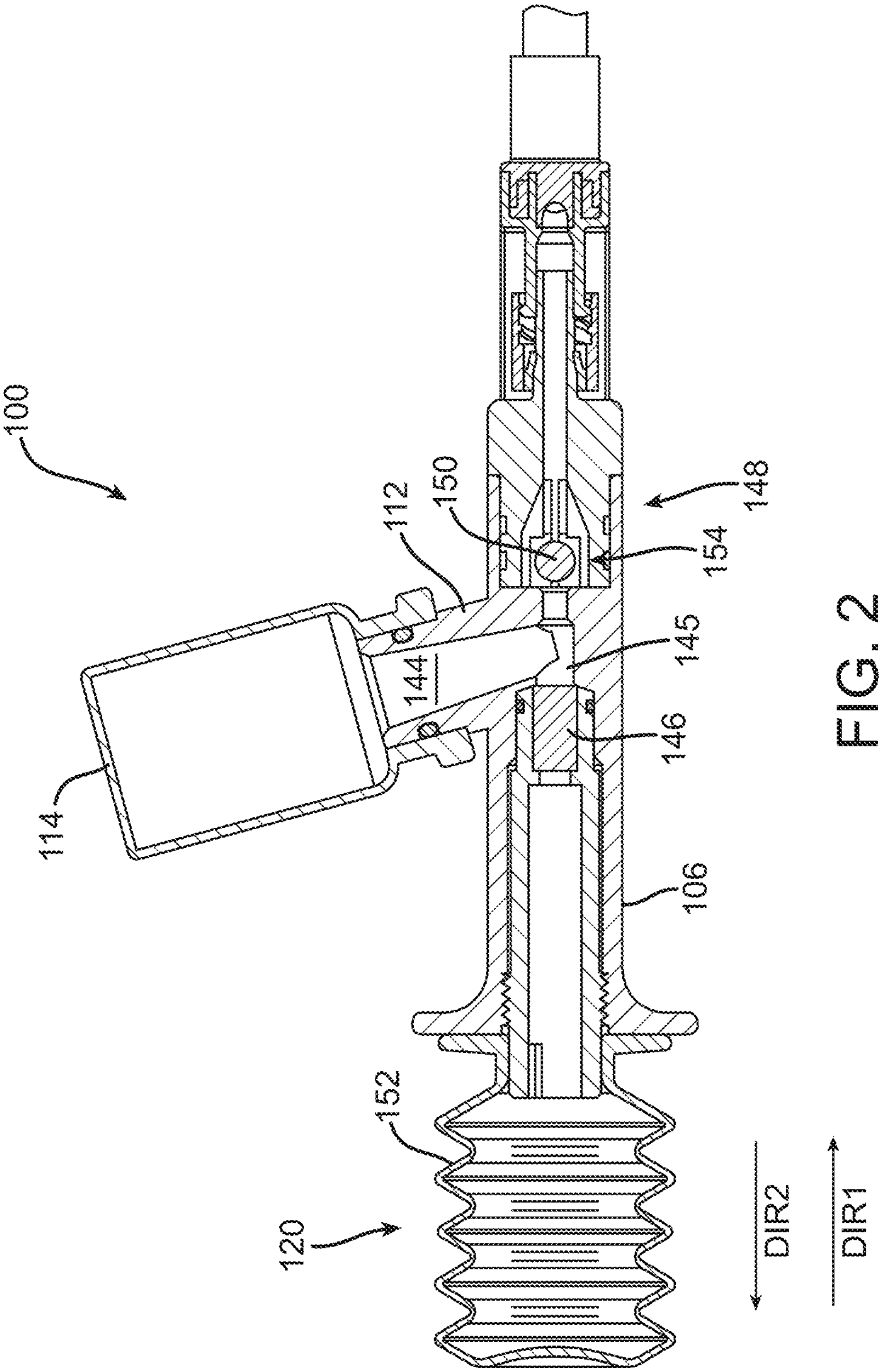
FIG. 2 is a cross-sectional view of a powder delivery system of the combined powder and liquid delivery device shown in FIG. 1C.

Referring to FIG. 2, in one embodiment, the combined powder and liquid delivery device 100 preferably includes the delivery device housing 106 having the first vial connector. 112 that is adapted for connecting the first vial 114 to the delivery device housing 106, whereupon the first vial 114 is in fluid communication with the powder delivery system 120 and a powder chamber 145 of the combined powder and liquid delivery device 100.

In one embodiment, the powder delivery system 120 may be operated to generate a vacuum for drawing a dose of powder from the first vial 114 into the powder chamber 145 of the delivery device housing 106, and then generating high pressure air for dispensing the dose of the powder from the distal end of the combined powder and liquid delivery device 100. In one embodiment, the powder delivery system 120 preferably includes the powder chamber 145 that is in communication with a powder supply channel 144 of the first vial connector 112.

In one embodiment, the size of the dose of powder that may be drawn into the powder chamber 145 may be controlled by adjusting and/or modifying the diameter and/or length of the powder chamber. For example, a larger diameter will result in a larger dose and a smaller diameter will result in a smaller dose.

In one embodiment, the powder delivery system 120 preferably includes a filter 146 that allows air to pass therethrough in proximal and distal directions, but which prevents the powder from passing through the filter.

In one embodiment, the powder delivery system 120 preferably includes a one-way valve 148 that includes a ball 150 that is free to move in proximal and distal directions within a central chamber 154 the one-way valve 148.

In one embodiment, the powder delivery system 120 preferably includes a bellows 152 that may be compressed in the distal direction DIR1 for forcing air to flow in the distal direction through the powder chamber 145. In one embodiment, the powder delivery system 120 preferably includes an internal spring 180 (FIG. 7) located inside the bellows 152 that normally urges the bellows into the extended position shown in FIG. 2. Thus, when the bellows 152 is compressed in a distal direction DIR1, after the compressing force is removed, the internal spring 180 located inside the bellows urges the bellows to move in the proximal direction DIR2 to return the bellows to the extended position shown in FIG. 2.

In one embodiment, when the internal spring forces the bellows 152 to expand in the proximal direction DIR2, ambient air is drawn through the one-way valve 142 (FIGS. 1A-1D) that is in communication with the first vial connector 112. The expanding bellows 152 generates a vacuum that draws ambient air into the powder chamber 145. The ambient air flows through the filter 146 and fills the interior volume of the bellows 152. The vacuum generated by the bellows. 152 pulls a dose of powder from the first vial 114. Under vacuum, the dose of powder preferably flows from the first vial 114, through the powder supply channel 144 and into the powder chamber 145. The filter 146 preferably blocks the dose of powder from being drawn into the bellows 152. After the dose of powder has been loaded into the powder chamber 145, the bellows 152 may be compressed in the distal direction DIR1 for forcing the powder to flow in the distal direction DIR1 toward the one-way valve 148 and the distal end of the combined powder and liquid delivery device 100.

In one embodiment, the one-way valve 148 preferably includes the ball 150 that is configured to move in the proximal direction DIR2 in response to a vacuum being generated by the bellows 152 of the powder delivery system 120 and move in the distal direction DIR1 in response to higher pressure air being generated by compressing the bellows 152 of the powder delivery system 120.

Figure 3:
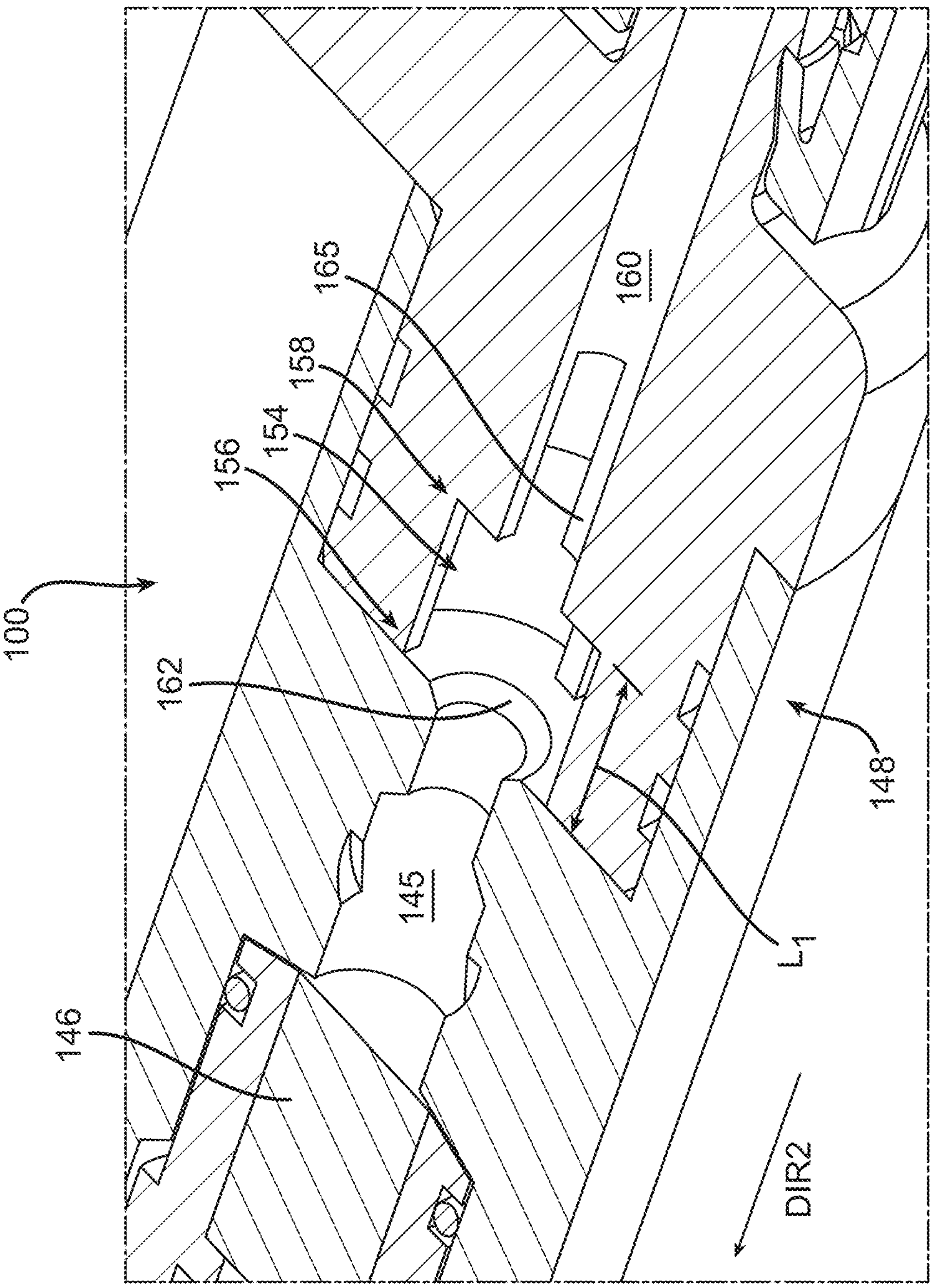
FIG. 3 is a cross-sectional view of a central chamber of a one-way valve of a powder and liquid delivery device, in accordance with one embodiment of the present patent application.

Referring to FIG. 3, in one embodiment, the one-way valve 148 is desirably located downstream from the filter 146 and the powder chamber 145. In one embodiment, the one-way valve 148 preferably includes a central chamber 154 that is adapted to contain the ball 150 (FIG. 2). The ball is free to move in proximal and distal directions along the length of the central chamber 154 of the one-way valve 148.

In one embodiment, the central chamber 154 of the one-way valve 148 preferably has a length Li that is greater than the outer diameter of the ball 150 (FIG. 2) so that the ball can move in proximal and distal directions along the length of the central chamber 154.

In one embodiment, the central chamber 154 has a proximal end 156 with a proximal sealing surface 162, which is adapted to engage an outer surface of the ball to form a seal.

In one embodiment, as the bellows 152 (FIG. 2) moves from a compressed configuration to an extended configuration, a vacuum is generated in the powder chamber 145. The vacuum pulls the ball 150 (FIG. 2), located in the central chamber 154, in the proximal direction DIR2 so that the ball seals against the proximal sealing surface 162 of the one-way valve 148. By sealing the proximal sealing surface 162, the ball 150 prevents moisture from being drawn into the powder chamber 145, which prevents premature activation of the powder.

Figure 4:
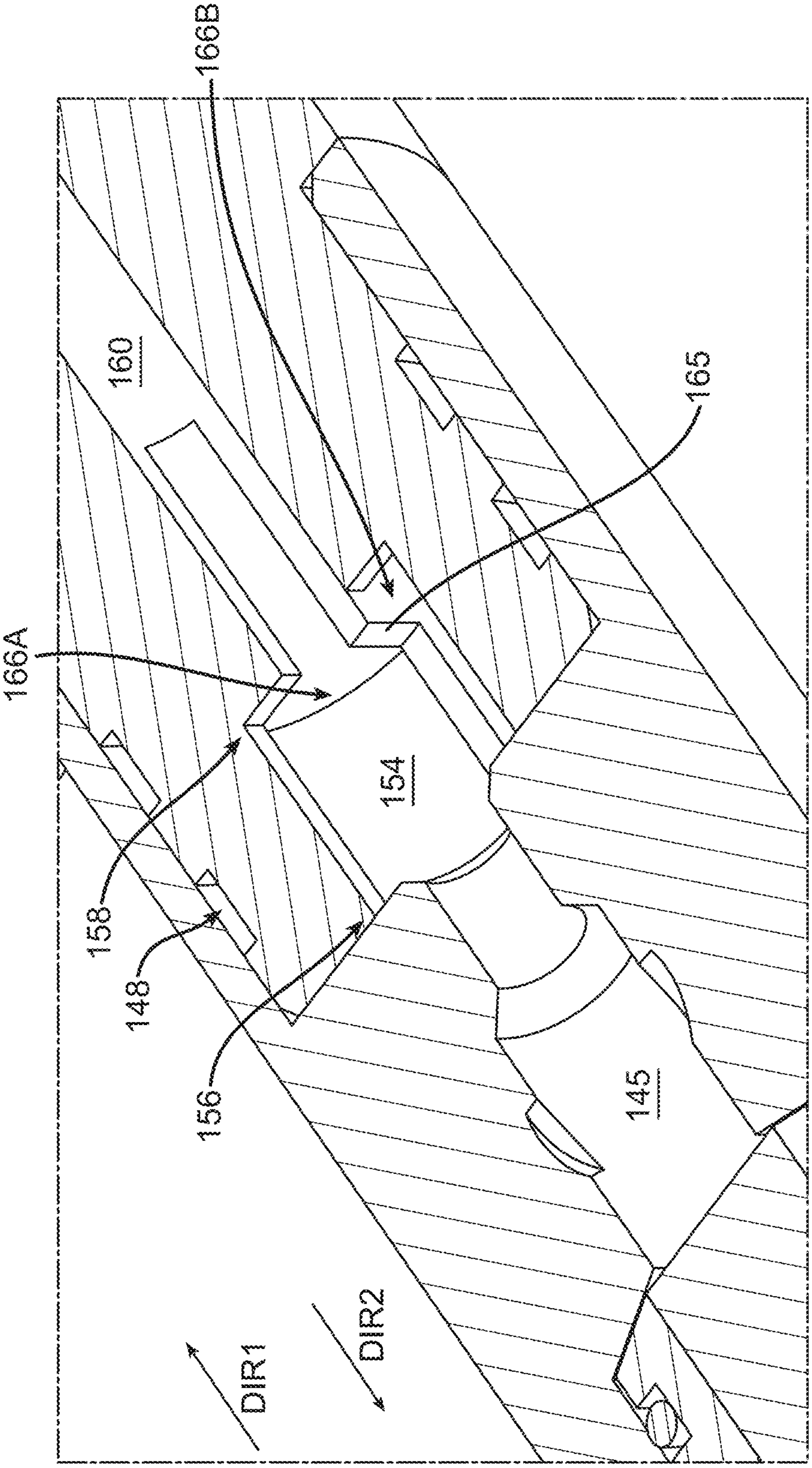
FIG. 4 is another cross-sectional view of the central chamber of the one-way valve shown in FIG. 3.

Referring to FIG. 4, the one-way valve 148 preferably includes a ball stop 165 that is adjacent the distal end 158 of the central chamber 154 of the one-way valve 148. The ball stops 165 preferably has a proximal face that is located proximal to the distal end 158 of the central chamber 154. When the ball 150 (FIG. 2) is forced by positive air pressure to move to the distal end 158 of the central chamber 154, the ball stop 165 holds the ball away from the distal end 158 to prevent a seal from being formed between the outer surface of the ball and the distal end of the central chamber of the one-way valve. Thus, when the ball engages the ball stop 165, the high-pressure air and the powder flowing in the distal direction DIR1 is free to flow through gaps 166A, 166B that are located on opposite lateral sides of the ball stop 165, whereupon the powder can flow downstream to reach the powder delivery channel 160.

Figure 5:
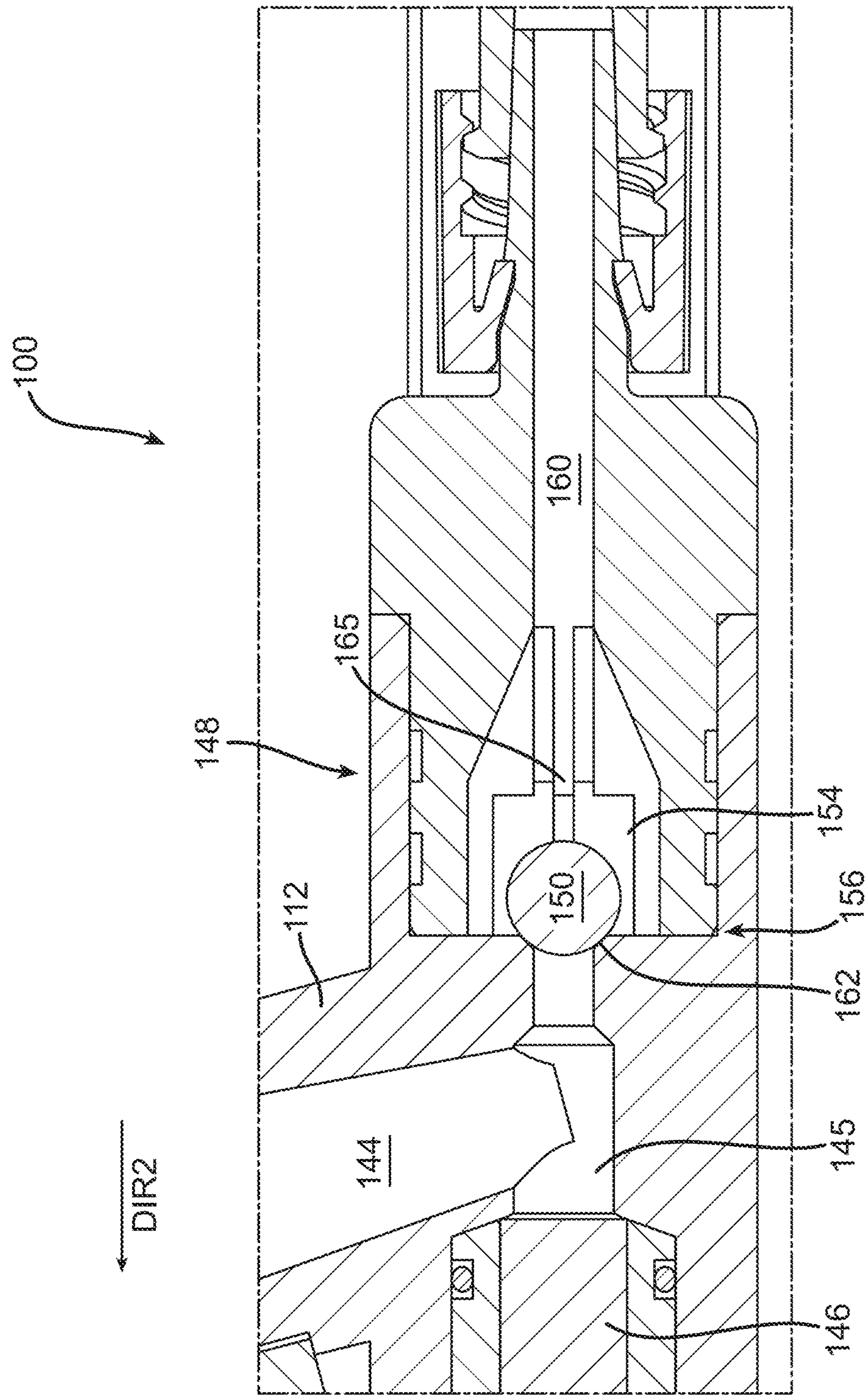
FIG. 5 is a cross-sectional view of a one-way valve of a powder and liquid delivery device, with a ball in a proximal position, in accordance with one embodiment of the present patent application.

Referring to FIG. 5, in one embodiment, when the bellows expands to generate a vacuum within the powder chamber 145, a dose of the powder in the first vial 114 (FIG. 2) is drawn through the powder supply channel 144 of the first vial connector 112 and fills the powder chamber 145. The vacuum preferably pulls the ball 150 in a proximal direction DIR2 until the outer surface of the ball seats against the proximal sealing surface 162, which is located at the proximal end of the central chamber 154 of the one-way valve 148. The seal formed between the outer surface of the ball 150 and the proximal sealing surface 162 desirably prevents any moisture that may be present in the powder dispensing channel 160 from travelling upstream beyond the proximal end 156 of the one-way valve 148, which prevents clogging and/or clumping of any of the powder that is in the powder chamber 145 or the powder supply channel. 144. Thus, the one-way valve 148 preferably prevents clogging of the powder and liquid delivery system 100, which would occur due to activation of the powder (e.g., by a liquid) prior to the powder being dispensed from the distal end of the device.

Figure 1D:
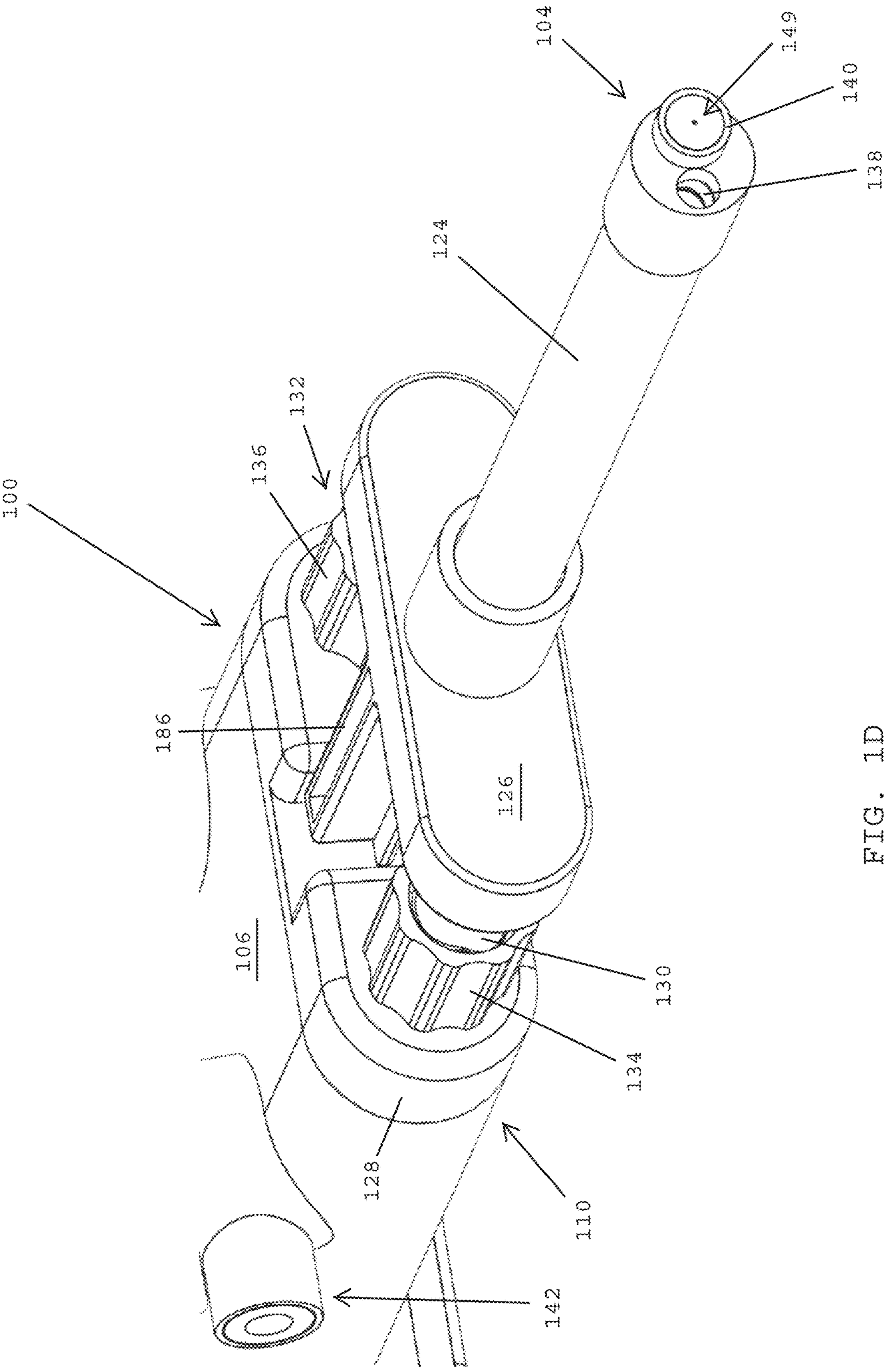
FIG. 1D is a perspective view of a distal end of the combined powder and liquid delivery device shown in FIGS. 1A-IC.
Figure 6:
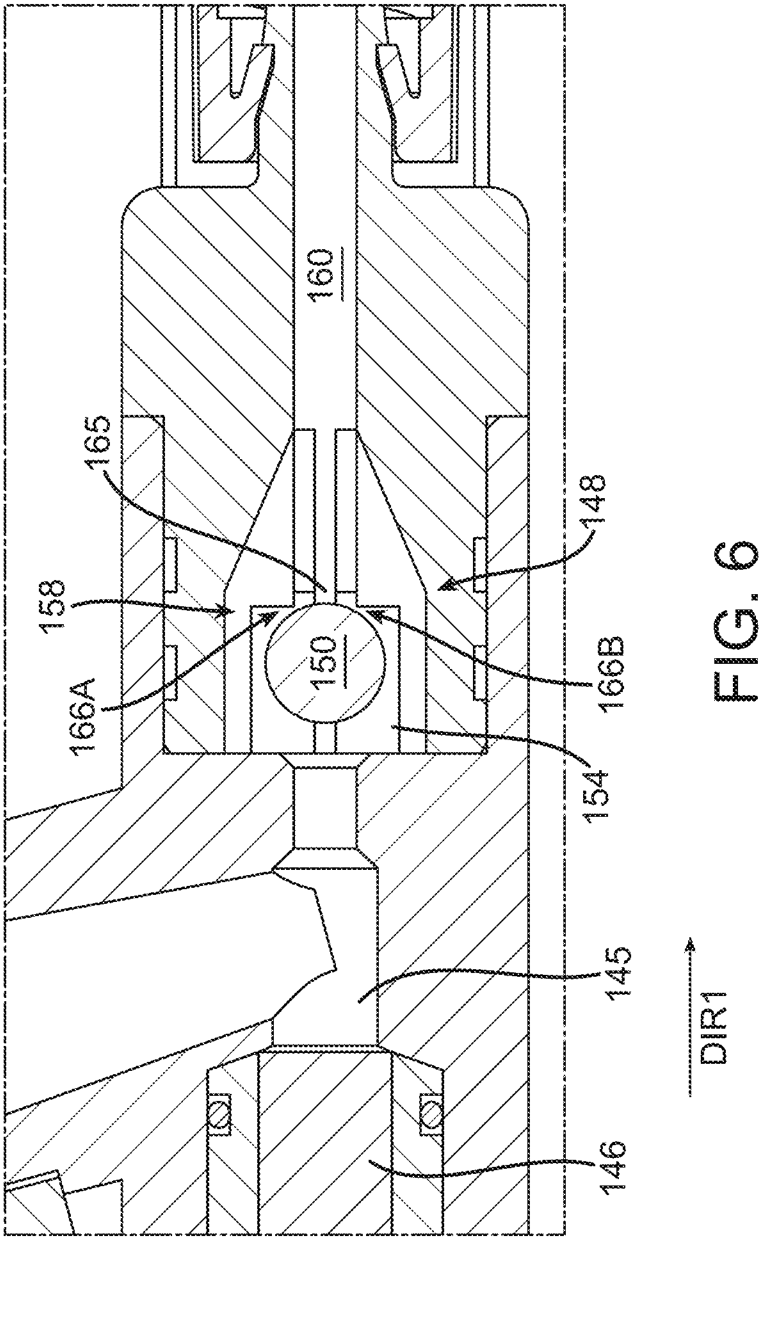
FIG. 6 is a cross-sectional view of the one-way valve shown in FIG. 5, with the ball in a distal position.

Referring to FIG. 6, in one embodiment, when the bellows 152 (FIG. 2) is compressed in the distal direction DIR1, positive air pressure flows in the distal direction DIR1 through the filter 146 and the powder chamber 145 for forcing the dose of powder within the powder chamber to flow in the distal direction until it reaches the one-way valve 148. The distally flowing air forces the ball 150 to move in the distal direction DIR1 until the outer surface of the ball abuts against a proximal face of the ball stop 165. The proximal face of the ball stop, located proximal to the distal end 158 of the central chamber 154 of the one-way valve 148, spaces the outer surface of the ball 150 away from the distal end 158 of the central chamber 154 so that the distally flowing powder and air can pass through the gaps 166A, 166B that are present on opposite lateral sides of the ball stop 165. Thus, the outer surface of the ball 150 does not seal the powder delivery channel 160 so that the powder is free to flow distally beyond the ball 150 and the ball stop 165 until it reaches the powder delivery channel 160. The high-pressure air generated by the powder delivery system preferably forces the powder to flow distally through the powder delivery channel 160 until the powder is delivered from the powder delivery opening 138 located at the distal end 104 of the applicator tip 124 of the combined powder and liquid delivery device 100 (FIG. 1D).

Figure 7:
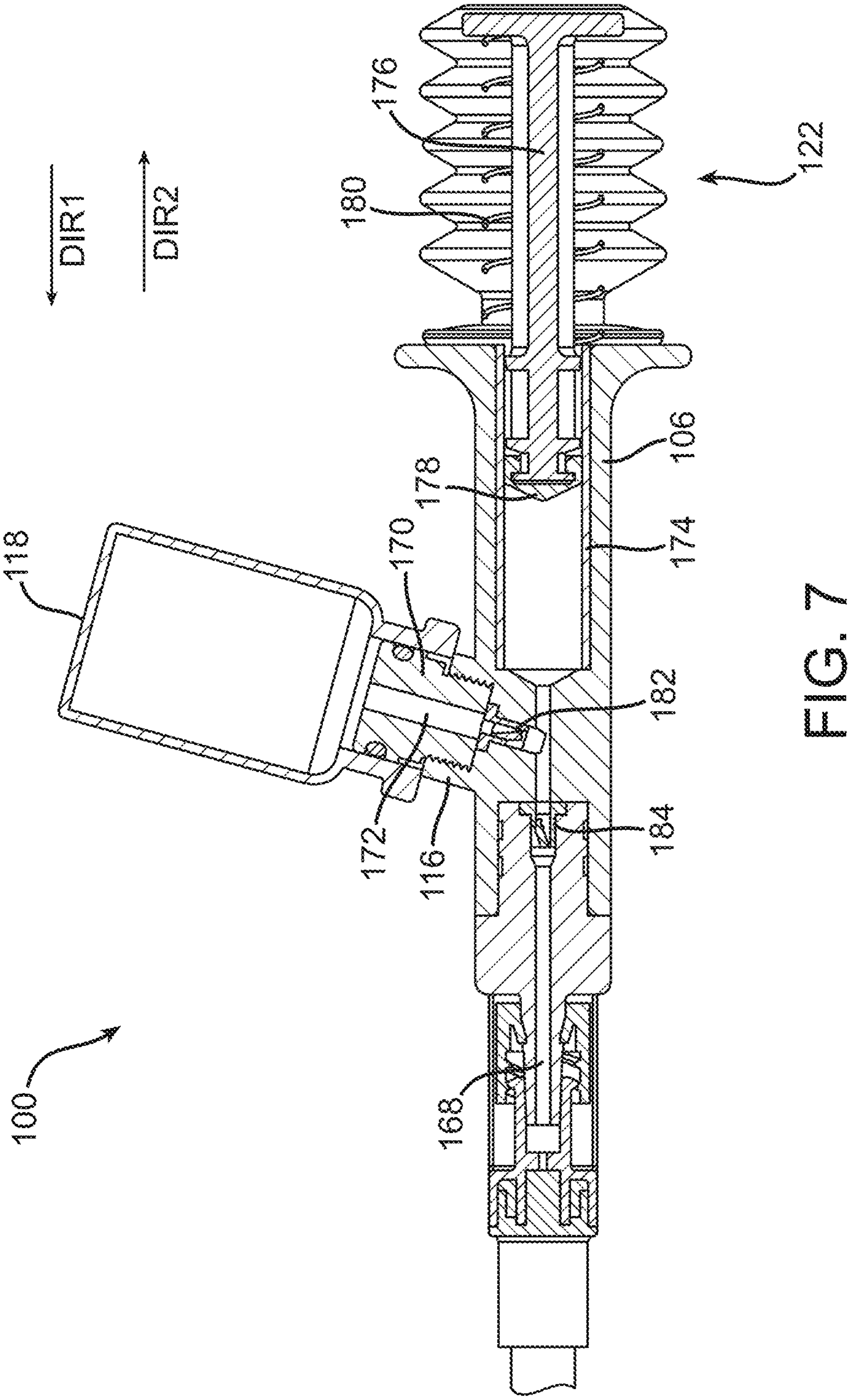
FIG. 7 is a cross-sectional view of a liquid delivery system of the combined powder and liquid delivery device shown in FIGS. 1A-1D.

Referring to FIG. 7, in one embodiment, the combined powder and liquid delivery device 100 preferably includes a liquid delivery system 122 for drawing liquid (e.g., activation fluid, saline solution) into a liquid chamber or liquid reservoir of the delivery device housing 106 and dispensing the liquid at the distal end of the applicator tip of the delivery device. In one embodiment, the combined powder and liquid delivery device 100 preferably includes the second vial connector 116 (FIG. 1A) that is adapted to connect the second vial 118 to the delivery device housing 106. In one embodiment, the combined powder and liquid delivery device 100 desirably includes a liquid reservoir connector 170 having a liquid supply channel 172 that is adapted to direct the liquid from the second vial 118 into the liquid chamber of the delivery device housing 106.

In one embodiment, the liquid delivery system 122 preferably includes a syringe barrel 174 that is disposed inside the delivery device housing 106, a syringe plunger 176 that is disposed inside the syringe barrel, a syringe piston 178 that is secured to the distal end of the syringe plunger 176. In one embodiment, the syringe plunger 176 preferably engages the inner surface of the syringe barrel 174 for forcing liquid from an opening at the distal end of the syringe barrel 174. In one embodiment, the liquid delivery system 122 preferably includes a syringe plunger spring 180 that urges the syringe plunger 176 to return to the extended position shown in FIG. 7. In one embodiment, the volume of the liquid that is drawn into the syringe barrel 174 (i.e., dose control) is responsive to how far the syringe plunger 176 is extended by the syringe plunger spring 180. In particular, less extension of the syringe plunger by the syringe plunger spring will result in a relatively lower volume of liquid being drawn into the syringe barrel and more extension of the syringe plunger by the syringe plunger spring will result in a relatively greater volume of liquid being drawn into the syringe barrel.

In one embodiment, the liquid delivery system 122 preferably includes a first one-way valve 182 that allows liquid stored in the second vial 118 to be drawn into the syringe barrel. 174 when the syringe plunger 176 is retracted in the proximal direction DIR2. The liquid delivery system 122 preferably includes a second one-way valve 184 that is located downstream of the first one-way valve 182. The second one-way valve 184 desirably allows the liquid from the syringe barrel 174 to flow in the distal direction DIR1, however, the second one-way valve 184 prevents the liquid from reversing direction and flowing in the proximal direction DIR2. In one embodiment, when the syringe plunger 176 is retracted, the liquid within the second vial 118 passes through the liquid supply channel 172 and through the first one-way valve 182 for filling the syringe barrel 174. When the syringe plunger 176 is depressed in the distal direction DIR1, the liquid within the syringe barrel 174 is forced to flow through the opening at the distal end of the syringe barrel 174 and through the second one-way valve 184, whereupon it flows distally into the liquid delivery channel 168 so that it can be delivered to the distal end of the combined powder and liquid delivery device 100.

Figure 8:
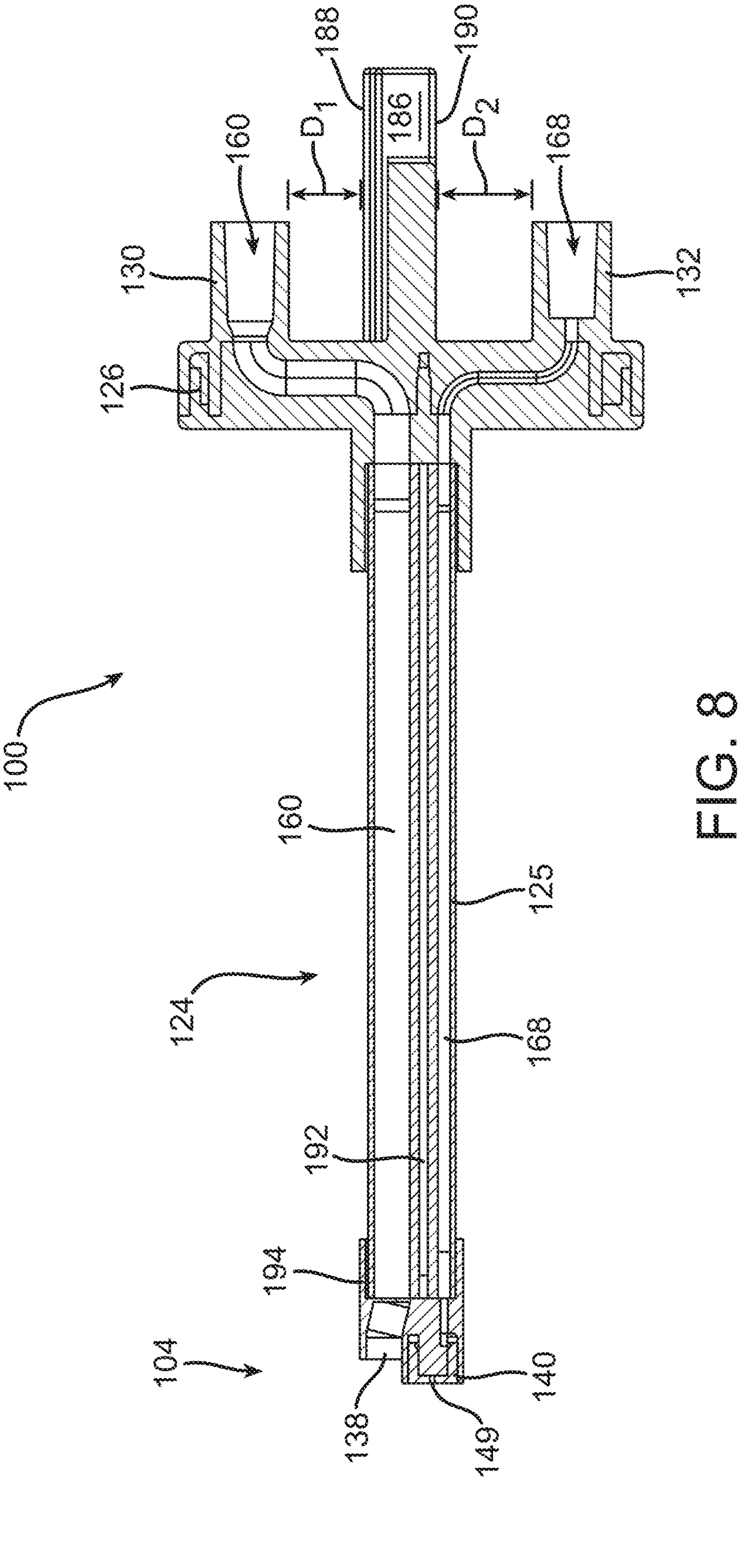
FIG. 8 is a cross-sectional view of an applicator tip of a powder and liquid delivery device, in accordance with one embodiment of the present patent application.

Referring to FIG. 8, in one embodiment, the combined powder and liquid delivery device 100 preferably includes the applicator tip 124 that is configured for delivering the powder and the liquid to the distal end 104 of the delivery device 100 (FIG. 1A). In one embodiment, the combined powder and liquid delivery device 100 desirably includes the applicator tip base 126 that is designed for interconnecting the proximal end of the applicator tip 124 with the distal end 110 of the delivery device housing 106 (FIG. 1A). The applicator tip base 126 preferably includes a stabilizing bar 186 that is configured to engage a distal end of the applicator tip connector 128 (FIG. 1C) for stabilizing the applicator tip 124 and preventing the applicator tip from twisting and/or rotating about its longitudinal axis.

In one embodiment, the stabilizing bar 186 is positioned off-center relative to the center of the elongated tube 125 of the applicator tip 124 to ensure that the applicator tip can only be attached in one orientation relative to the distal end of the delivery device housing. In one embodiment, the stabilizing bar 186 desirably has a first lateral surface 188 that defines a first distance $D_1$ between the first lateral surface 188 and the inner surface of the powder connector 130. The stabilizing bar 186 preferably includes a second lateral surface 190 that defines a second distance $D_2$ between the second lateral surface 190 and the inner surface of the liquid connector 132. In one embodiment, the second distance $D_2$ is greater than the first distance $D_1$ so that the spacing between the stabilizing bar 186 and the powder connector 130 is less than the spacing between the stabilizing bar 186 and the liquid connector 132. The off-center positioning of the stabilizing bar 186 allows the applicator tip 124 to be assembled with the combined powder and liquid delivery device in only one orientation so that the powder delivery channel 160 of the applicator tip 124 is in fluid communication with the powder delivery system and so that the liquid delivery channel 168 of the applicator tip 124 is in fluid communication with the liquid delivery system. Thus, the configuration of the stabilizing bar 186 provides a fail-safe method of making a connection that prevents erroneous coupling of the applicator tip 124 with the respective powder delivery system and liquid delivery system. As a result, a user is guaranteed that the powder delivery channel in the applicator tip is in fluid. communication with the powder delivery system and the liquid delivery channel in the applicator tip is in fluid communication with the liquid delivery system.

In one embodiment, the distal end of the applicator tip 124 preferably includes the powder delivery opening 138 that is in communication with the powder delivery channel 160 (FIG. 5) of the powder delivery system. The distal end of the applicator tip 124 also preferably includes the liquid spray cup 140 that is adapted to spray the liquid from the distal end 104 of the liquid delivery channel 168 of the combined powder and liquid delivery device 100. In one embodiment, the spray cup 140 has a liquid spray opening 149 that is preferably located distal to the powder delivery opening 138 to prevent any moisture that is present in the liquid from entering into the powder delivery opening 138 or the powder delivery channel 160, which could clog the powder delivery channel and/or the powder delivery system of the combined powder and liquid delivery device 100.

Figure 9:
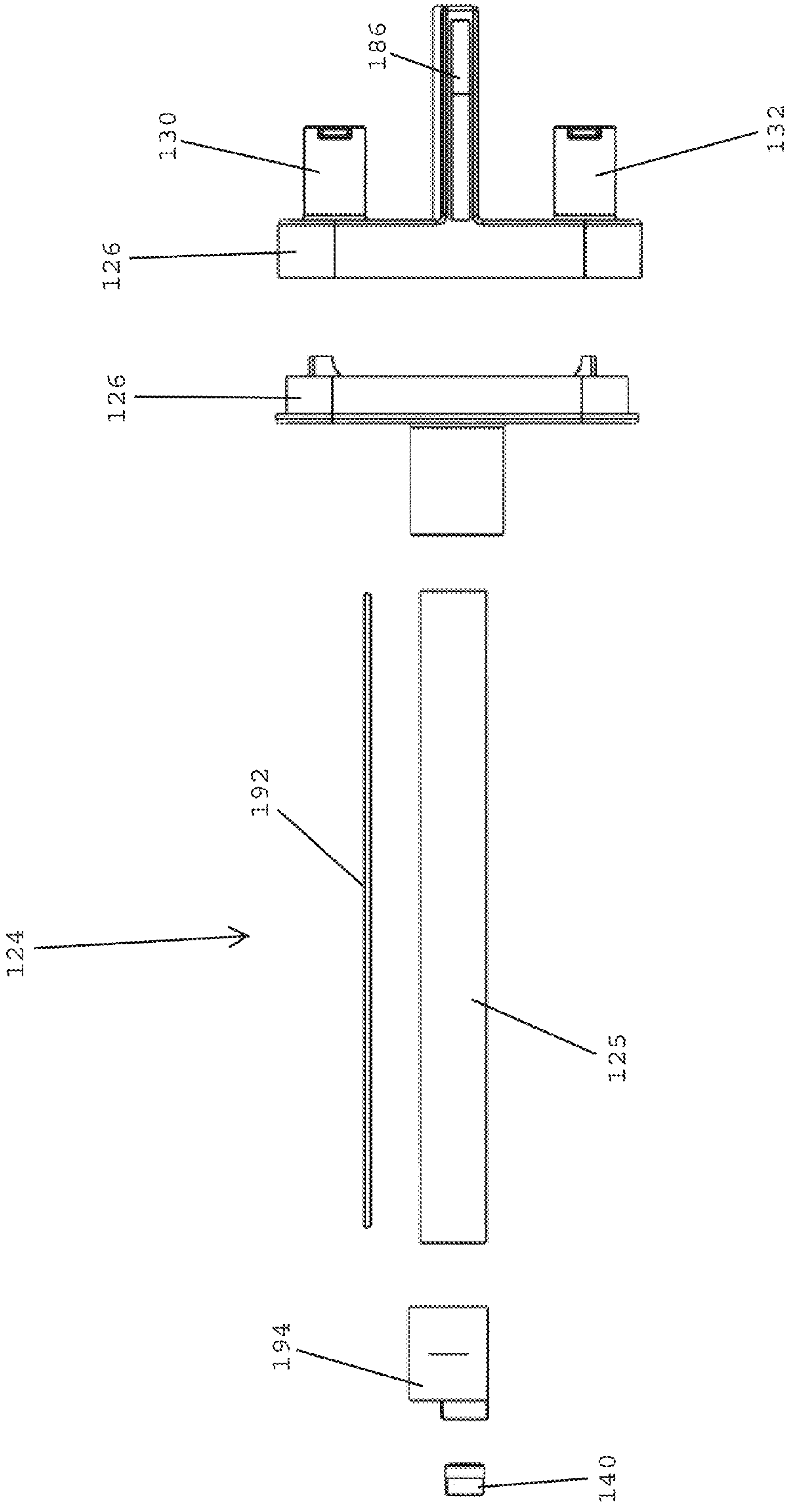
FIG. 9 is an exploded view of the applicator tip shown in FIG. 8.

Referring to FIGS. 8 and 9, in one embodiment, the applicator tip 124 preferably includes the elongated tube 125 that contains the powder delivery channel 160 and the liquid delivery channel 168. The applicator tip 124 preferably includes the applicator tip base 126 having the powder connector 130 that is adapted for being coupled with the powder delivery channel and the liquid connector 132 that is adapted for being coupled with the liquid delivery channel 168. The applicator tip base 126 preferably includes the stabilizing bar 186 that projects in a proximal direction and that is adapted to engage the distal end of the applicator tip connector 128 (FIG. 1C) for stabilizing the applicator tip 124 when it is secured to the distal end of the delivery device housing 106 (FIG. 1A).

In one embodiment, the applicator tip 124 preferably includes a malleable wire 192 that is located between the powder delivery channel 160 and the liquid delivery channel 168. The malleable wire 192 preferably enables the distal end of the applicator tip 124 to be moved into certain angles for facilitating delivery of the hemostat powder and the liquid to tissue or a wound. A surgeon can bend the malleable wire to select an angle for delivering the powder and the liquid.

In one embodiment, the applicator tip 124 preferably includes a dual-lumen powder and liquid connector 194 that is secured over the distal end of the elongated tube 125. The dual-lumen powder and liquid connector 194 preferably includes the powder delivery opening 138 for delivering the powder that is within the powder delivery channel/lumen 160. The dual-lumen powder and liquid connector 194 is also in communication with the distal end of the liquid delivery channel 168 and has an opening that is adapted to seat the liquid spray cup 140 that is utilized for spraying the liquid from the distal end of the applicator tip 124. In one embodiment, the dual-lumen powder and liquid connector 194 desirably positions the spray cup 140 at a location that is distal to the powder delivery opening 138 so that the liquid dispensed from the spray cup does not move and/or migrate into the powder delivery opening 138, which could clog the powder delivery channel 160.

Figure 10A:
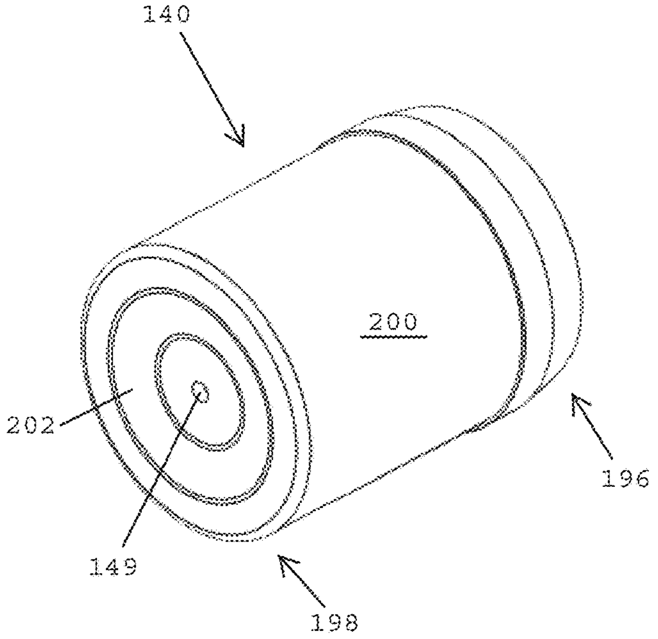
FIG. 10A is a perspective view of a distal end of a liquid spray cup of an applicator tip of a powder and liquid delivery device, in accordance with one embodiment of the present patent application.
Figure 10B:
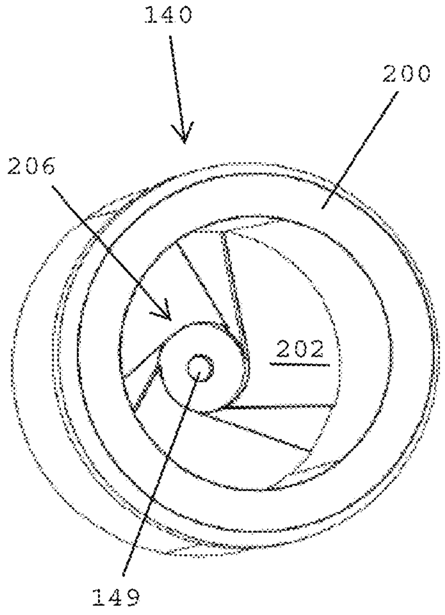
FIG. 10B is a perspective view of a proximal end of the liquid spray cup shown in FIG. 10A.
Figure 10C:
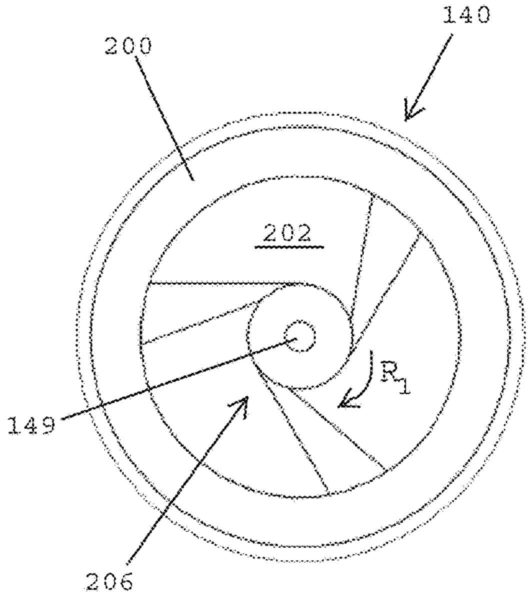
FIG. 10C is a proximal end view of the liquid spray cup shown in FIGS. 10A and 10B.
Figure 10D:
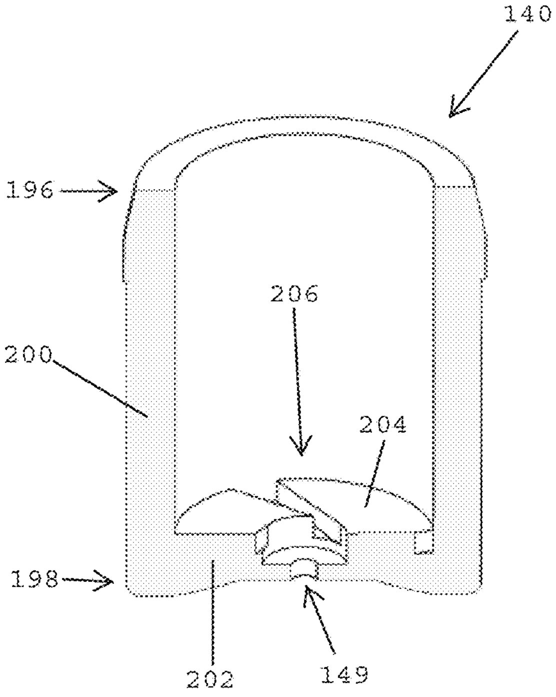
FIG. 10D is a cross-sectional view of the liquid spray cup shown in FIGS. 10A-10C.

Referring to FIGS. 10A-10D, in one embodiment, the liquid spray cup 140 preferably has a proximal end 196, a distal end 198 and a cylindrical shaped outer wall 200 that extends from the proximal end 196 to the distal end 198. In one embodiment, the proximal end of the cylindrical shaped outer wall 200 is open and the distal end of the cylindrical shaped outer wall 200 is closed by an end wall 202 having the liquid spray opening 149 formed therein. Referring to FIGS. 10B-10D, in one embodiment, the end wall 202 has a proximal face 204 with a swirl chamber 206 formed therein that is adapted to spin the liquid, such as in a clockwise direction $R_1$ (FIG. 10C), as the liquid is dispensed from the liquid spray opening 149 of the liquid spray cup 140 to preferably produce a fine mist of liquid that is sprayed from the distal end of the combined powder and liquid delivery device.

In one embodiment, the opening at the proximal end 196 of the liquid spray cup 140 is preferably in fluid communication with the liquid delivery lumen 168 that passes through the elongated tube 125 of the applicator tip 124 (FIG. 8).

In one embodiment, the liquid spray cup 140 shown and described in FIGS. 10A-10D preferably incorporates one or more of the structural features disclosed in U.S. Patent Application Publication No. 2021/0101162 to Trezza, II, et al., assigned to Ethicon, Inc. of Somerville, New Jersey, the disclosure of which is hereby incorporated by reference herein.

The combined powder and liquid delivery device disclosed herein may have broad functionality and provide numerous benefits.

In one embodiment, a combined powder and liquid delivery applicator device may single-handedly apply powder and liquid to the surgical site, sequentially or simultaneously. In one embodiment, the powder may be dispensed at a surgical site, followed by the liquid being dispensed onto the powder. In one embodiment, the powder and the liquid may be simultaneously dispensed at a surgical site.

In one embodiment, a combined powder and liquid delivery device may provide a system in which the powder dispensing is dose controlled so that the powder may be uniformly dispensed and applied in a controlled manner.

In one embodiment, a combined powder and liquid delivery device may provide a system in which the liquid dispensing is dose controlled so that the liquid may be uniformly dispensed and applied in a controlled manner. In one embodiment, a spray tip may be utilized to spray an activation liquid over powder (e.g., a previously applied powder layer).

In one embodiment, the spray tip used to dispense a liquid and the powder delivery opening used to deliver the powder are staggered from one another to prevent the liquid from moving into and/or contacting the powder delivery opening.

In one embodiment, a one-way valve is disposed within the powder delivery channel to prevent moist air and/or liquid from being sucked into the powder chamber, thereby preventing clogging and/or premature powder activation.

In one embodiment, a combined powder and liquid delivery device may include and/or utilize vials that are pre-filled with the powder and the activation liquid. For example, a first vial may be pre-filled with a powder and a second vial may be pre-filled with an activation liquid.

In one embodiment, a combined powder and liquid delivery device preferably includes one or more powder vials that are designed to assist feeding the powder into a powder chamber or a powder delivery channel. In one embodiment, a powder vial may include a spring/filter assembly that is configured to push the powder onto a powder dispensing opening and/or the powder delivery channel.

In one embodiment, a powder vial may include an air valve (e.g., located at the proximal end of the powder vial) to allow air to flow into the powder vial as a dose of powder is being dispensed and/or sucked into the powder delivery channel.

Figure 11:
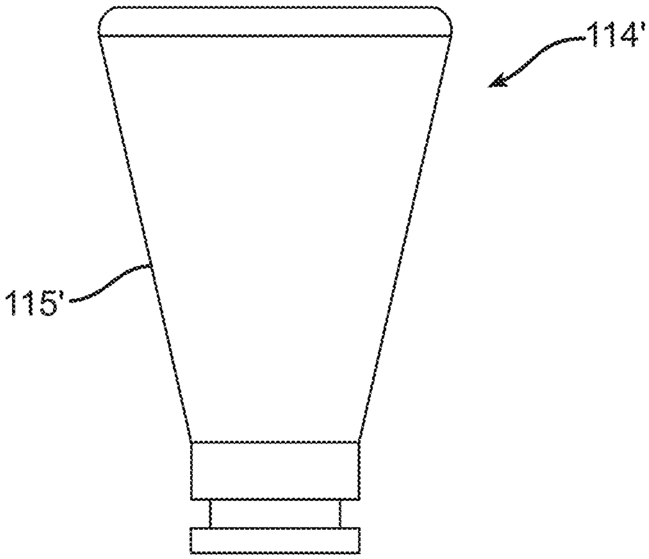
FIG. 11 is a side view of a powder vial for a powder and liquid delivery device, in accordance with one embodiment of the present patent application.

Referring to FIG. 11, in one embodiment, a powder vial 114' for use in a powder delivery system of a combined powder and liquid delivery device is preferably designed to ensure that the powder stored within the powder vial may be reliably and efficiently drawn from an open end of the vial. In prior art vials, the opening of a powder vial may be surrounded by a shelf or ledge that extends orthogonal or perpendicular to the longitudinal axis of the powder vial. The orthogonally extending shelf or ledge may present an obstacle that blocks the flow of the powder out of the open end of the prior art powder vial. To avoid the above-described blockage problems that are observed in prior art vials, in one embodiment, the powder vial 114' preferably has an outer wall 115' that defines a conical-shaped inner surface 117' (FIG. 12) that functions as a funnel and that eliminates the presence of any ledges or shelves inside the powder vial 114' that could block the powder from exiting the open end of the powder vial.

Figure 12:
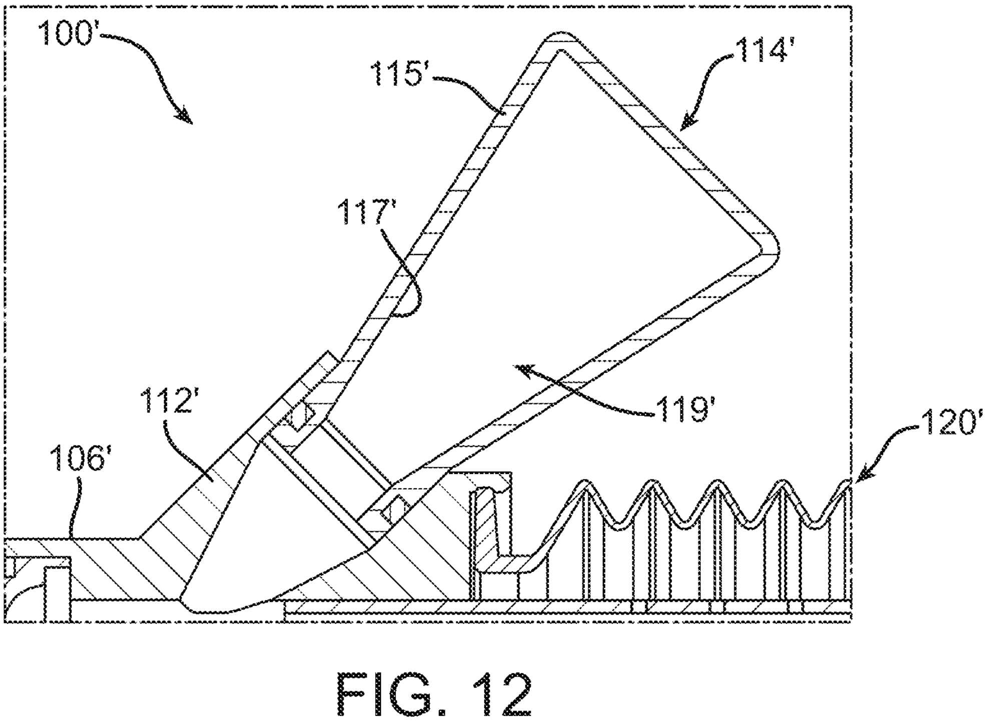
FIG. 12 is a cross-sectional view of the powder vial shown in FIG. 11 with the powder vial attached to a powder vial connector of a powder and liquid delivery device, in accordance with one embodiment of the present patent application.

Referring to FIG. 12, in one embodiment, the powder vial 114' may be coupled with a powder vial connector 112' on a delivery device housing 106' of a combined powder and liquid delivery device 100' The conical-shaped inner surface 117' of the powder vial 114' desirably ensures that the powder within the powder chamber 119' of the powder vial 114' will flow through the powder vial connector 112' and into the delivery device housing 106' so that it may be dispensed using the powder delivery system 120' of the combined powder and liquid delivery device 100'.

Figure 13:
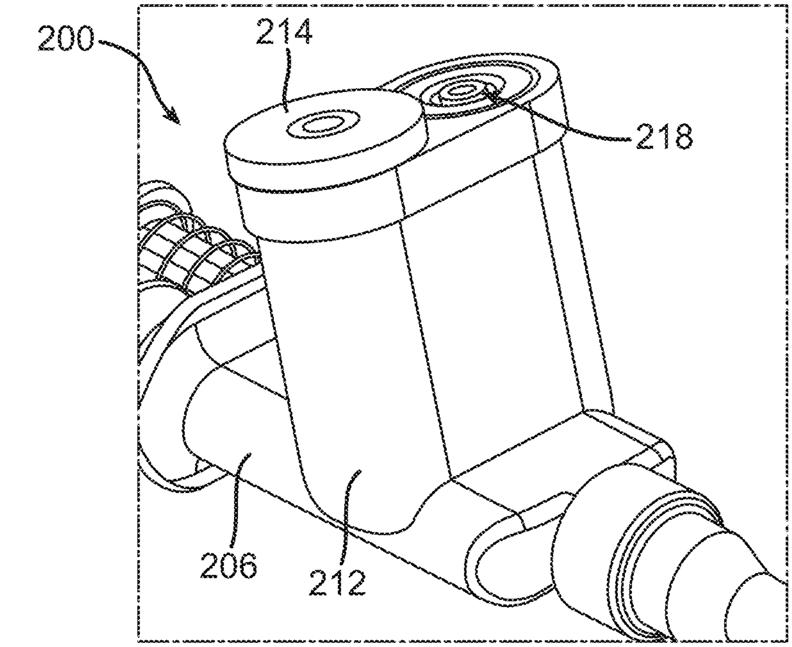
FIG. 13 is a perspective view of a powder and liquid connector of a powder and liquid delivery device, in accordance with one embodiment of the present patent application.

Referring to FIG. 13, in one embodiment, a combined powder and liquid delivery device 200 for delivering a powder and a liquid from a distal end of the device preferably includes a delivery device housing 206 having a powder/liquid connector 212 that is adapted to connect both a powder vial 214 and a liquid vial 218 with the delivery device housing 206. In one embodiment, the upper end of the powder/liquid connector 212 preferably includes a first opening that is adapted to receive a powder vial 214 that contains a powder (e.g., a hemostatic powder) and a second opening that is adapted to receive a liquid vial 218 that contains a liquid (e.g., a saline solution).

Figure 14:
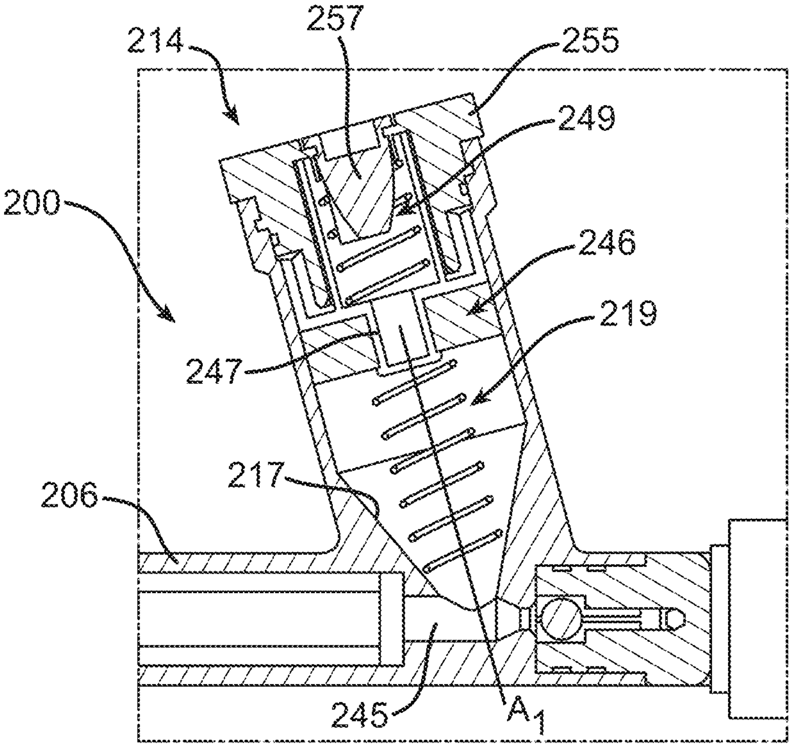
FIG. 14 is a cross-sectional view of the powder and liquid connector shown in FIG. 13, in accordance with one embodiment of the present patent application.

Referring to FIG. 14, in one embodiment, the powder vial 214 preferably includes a powder reservoir 219 that is adapted to receive powder. The powder vial 214 preferably has a conical-shaped inner surface 217 that eliminates perpendicular ledges or shelves that could prevent and/or block the powder from traveling into the powder chamber 245 of the combined powder and liquid delivery device 200.

In one embodiment, the powder vial 214 preferably includes a filter 246 that is held by a filter holder 247, which is adapted to support the filter 246 as the filter moves along the axis $A_1$ toward the lower end of the powder vial 214 and the powder chamber 245.

In one embodiment, the powder vial 214 preferably includes a spring 249 that urges the filter holder 247 and the filter 246 toward the lower, open end of the powder vial 214 for forcing the powder from the powder reservoir 219 and into the powder chamber 245.

In one embodiment, the powder reservoir 219 is maintained so that the volume of the powder chamber 245 is substantially filled with powder, with substantially no free air space or minimal free air space. The inventors of U.S. Pat. No. 10,507,293, the disclosure of which is hereby incorporated by reference herein, discovered that such an arrangement results in better uniformity of powder expression throughout an expression cycle, i.e., from when the combined powder and liquid delivery device 200 is fully charged with powder to when the powder reservoir 219 has been fully substantially emptied of all remaining powder, as well as resulting in better directional expressing uniformity, i.e., in minimal differences between the expression of powder with the applicator tip directed horizontally relative to being directed vertically.

In one embodiment, the spring 249 serves as a compressible advancer of the filter holder 247 and the filter 246. In one embodiment, when the powder delivery system is activated, a flow of air expresses the powder from the distal end of the combined powder and liquid delivery device 200. Simultaneously, the filter holder 247 and the filter 246 are compressed by the spring 249, which, in turn, applies pressure on the filter holder 247 and the filter 246, thereby causing the filter holder 247 and the filter 246 to move along the axis $A_1$ toward the lower end of the powder vial 214 for decreasing the volume of the powder reservoir 219 as the powder is expressed from the combined powder and liquid delivery device 200.

Thus, upon each expression of the powder from the combined powder and liquid delivery device 200, the filter holder 247 and the filter 246 advance toward the lower end of the powder vial 214 to take up the space within the powder reservoir 219 that is freed by the expressed powder. This action results in the volume of the powder reservoir 219 being constantly adjusted to correspond to the volume of the powder remaining in the powder reservoir 219 of the powder vial 214.

In one embodiment, the powder vial 214 preferably includes an end cap 255 having a one-way valve 257 incorporated therein that enables ambient air to be drawn through the length of the powder vial and into the delivery device housing 206. In one embodiment, when a powder delivery system generates a vacuum within the powder chamber 245, a dose of powder within the powder vial 214 is drawn into the powder chamber 245.

In one embodiment, when the vacuum is generated by the powder delivery system, ambient air is drawn into the powder vial 214 via the one-way valve 257. The ambient air passes through one or more apertures in the filter holder 247 and through the filter 246. The air preferably fills the bellows of a powder delivery system. As the powder is supplied from the lower end of the powder vial 214, the spring 249 forces the filter holder 247 and the filter 246 in a downward direction (i.e., toward the lower, open end of the powder vial) for pushing the powder that remains within the powder reservoir 219 of the powder vial 214 toward the lower end of the powder reservoir 219.

Figure 15A:
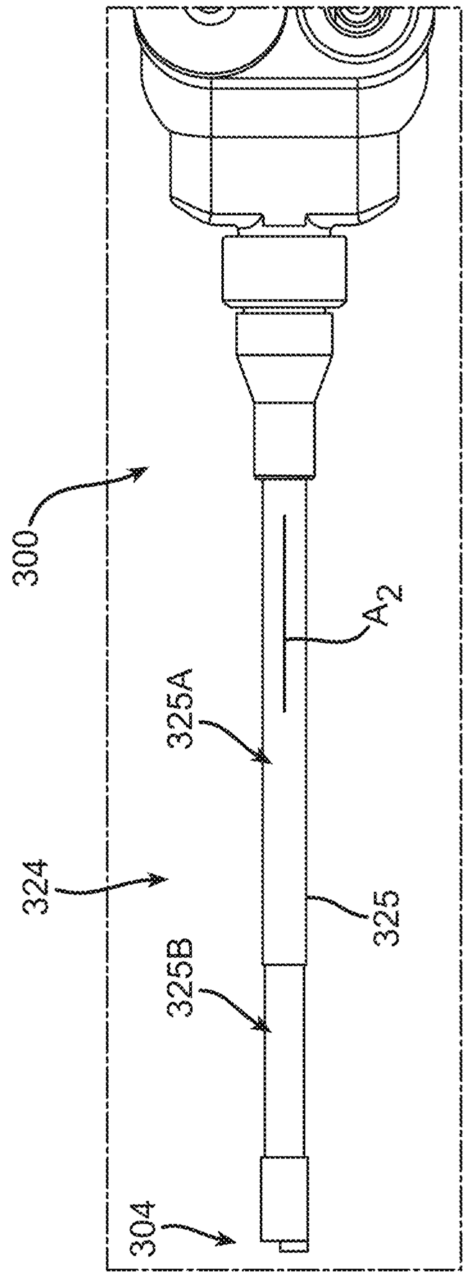
FIG. 15A is a side view of an applicator tip of a powder and liquid delivery device, in accordance with one embodiment of the present patent application.
Figure 15B:
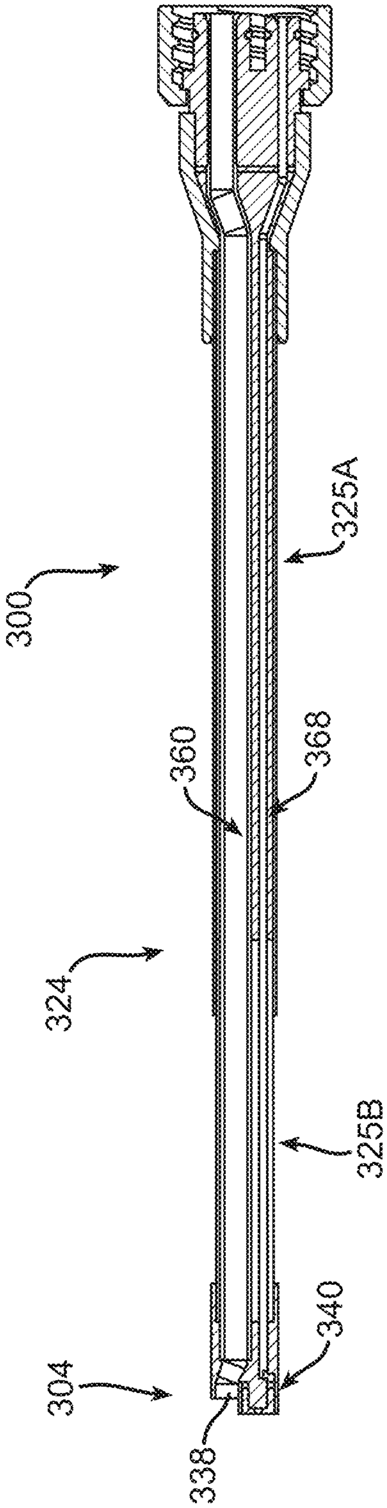
FIG. 15B is a cross-sectional view of the applicator tip shown in FIG. 15A.

Referring to FIGS. 15A and 15B, in one embodiment, an applicator tip 324 of a combined powder and liquid delivery device 300 preferably includes an elongated tube 325 having a rigid sheath section 325A and a flexible sheath section 325B that enables the distal end 304 of the applicator tip to be angulated for delivering the powder and the liquid at selected angles relative to the longitudinal axis $A_2$ of the rigid sheath section 325A.

Referring to FIG. 15B, in one embodiment, the powder delivery channel 360 passes through both the rigid sheath section 325A and the flexible sheath section 325B for delivering the powder to the distal end 304 of the combined powder and liquid delivery device 300, whereupon the powder may be delivered through the powder delivery opening 338 located that the distal end of the applicator tip 324. The liquid delivery channel 368 also desirably passes. through the rigid sheath section 325A and the flexible sheath section 325B of the applicator tip for delivering the liquid to the distal end 304 of the combined powder and liquid delivery device 300. In one embodiment, the liquid may be sprayed as a fine mist via a liquid spray opening 349 formed in a liquid spray cup 340. In one embodiment, the liquid is dispensed at a location that is distal to the powder delivery opening 338.

Figure 16:
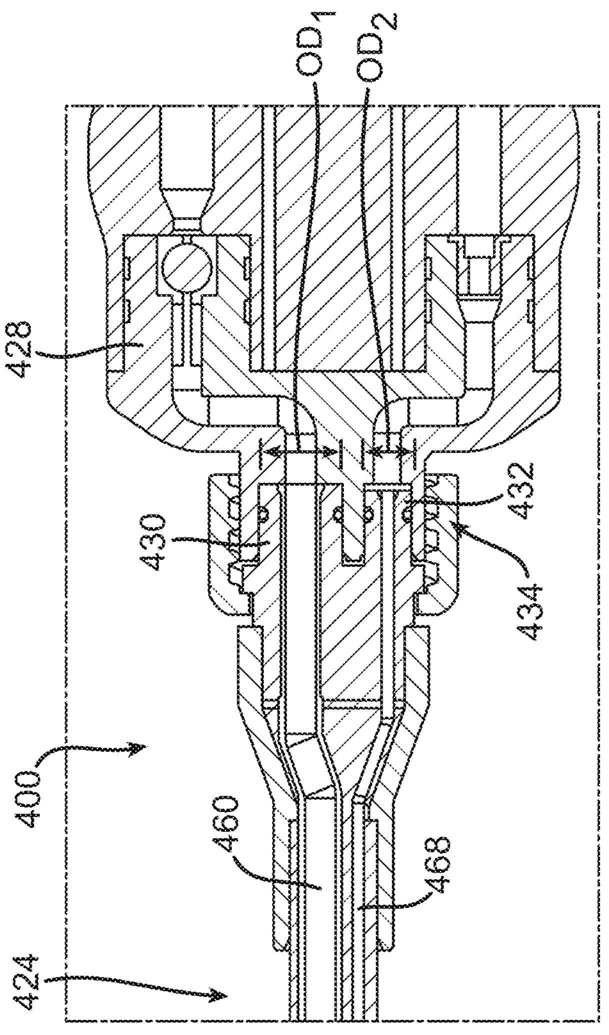
FIG. 16 is a cross-sectional view of a proximal end of an applicator tip and a tip connector utilized to connect the proximal end of the applicator tip to a device housing of a powder and liquid delivery device, in accordance with one embodiment of the present patent application.

Referring to FIG. 16, in one embodiment, the proximal end of an applicator tip 424 of a combined powder and liquid delivery device 400 preferably includes a powder connector 430 having an outer surface that defines a first outer diameter $OD_1$ and a liquid connector 432 having an outer surface that defines a second outer diameter $OD_2$ that is smaller than the first outer diameter $OD_1$. The different outer diameters of the respective powder connector 430 and liquid connector 432 provide a fail-safe means to ensure that the applicator tip 424 can be connected to the delivery device in only a single orientation so that the powder delivery channel 460 in the applicator tip 424 is properly aligned with the powder delivery system of the combined powder and liquid delivery device 400 and so that the liquid delivery channel 468 in the applicator tip 424 is properly aligned with the liquid delivery system of the combined powder and liquid delivery device 400. In one embodiment, a connecting collar 434 may be used for securing the powder connector 430 and the liquid connector 432 with the applicator tip connector 428. The connecting collar 434 may have threads for making a secure connection.

In one embodiment, the outer diameter of a powder connector may be smaller than an outer diameter of a liquid connector to provide a fail-safe means to ensure that the applicator tip can be connected in only a single orientation so that the powder delivery channel in the applicator tip is properly aligned with the powder delivery system of the combined powder and liquid delivery device and so that the liquid delivery channel is properly aligned with the liquid delivery system of the combined powder and liquid delivery device.

Figure 17:
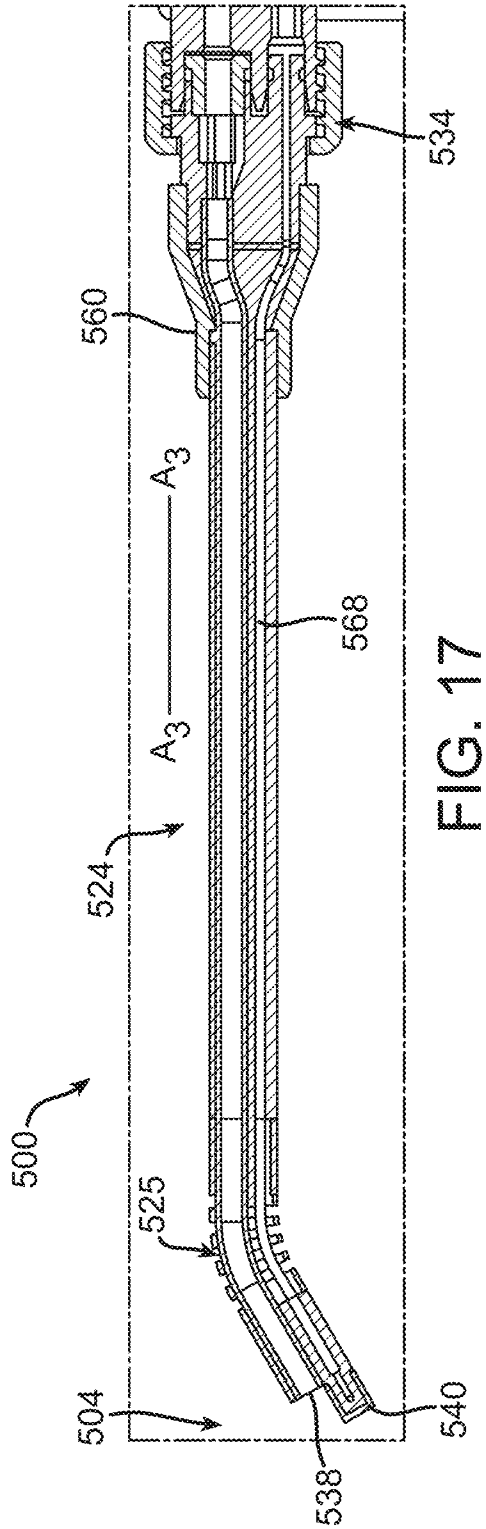
FIG. 17 is a side view of an applicator tip of a powder and liquid delivery device, in accordance with one embodiment of the present patent application.

Referring to FIG. 17, in one embodiment, an applicator tip 524 of a combined powder and liquid delivery device 500 preferably includes a flexible connector 525 that preferably enables the liquid spray cup 540 and the powder delivery opening 538 to be angulated relative to the longitudinal axis $A_3$ of a proximal section of the applicator tip 524. In one embodiment, a powder delivery channel 560 preferably passes through the length of the applicator tip 524 for delivering powder via the powder delivery opening 538 at the distal end 504 of the combined powder and liquid delivery device 500. In one embodiment, a liquid delivery channel 568 preferably extends through the length of the applicator tip 524 for delivering liquid to the liquid spray cup 540 located at the distal end 504 of the combined powder and liquid delivery device 500.

Figure 18A:
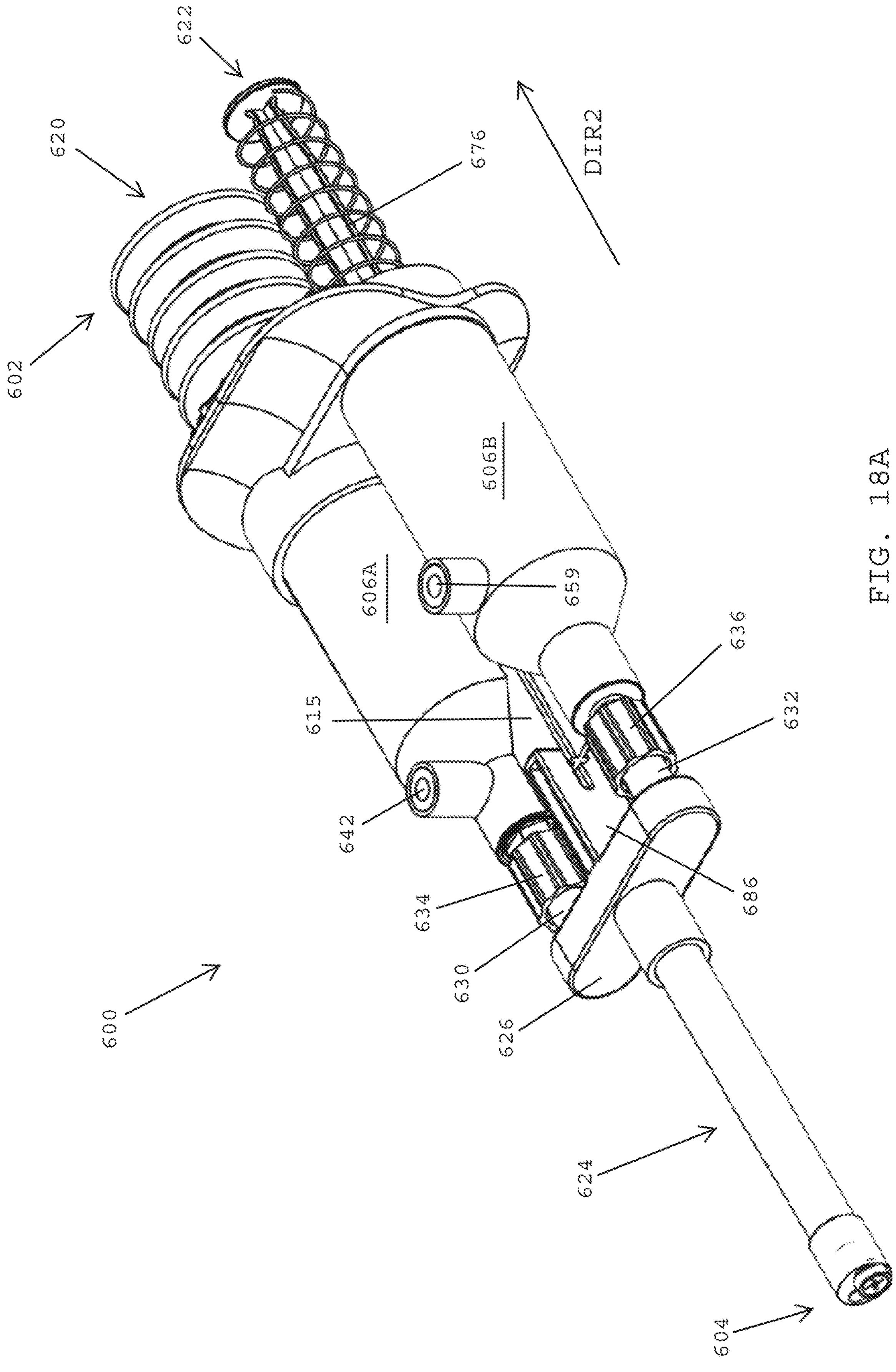
FIG. 18A is a perspective view of a powder and liquid delivery device, in accordance with one embodiment of the present patent application.
Figure 18B:
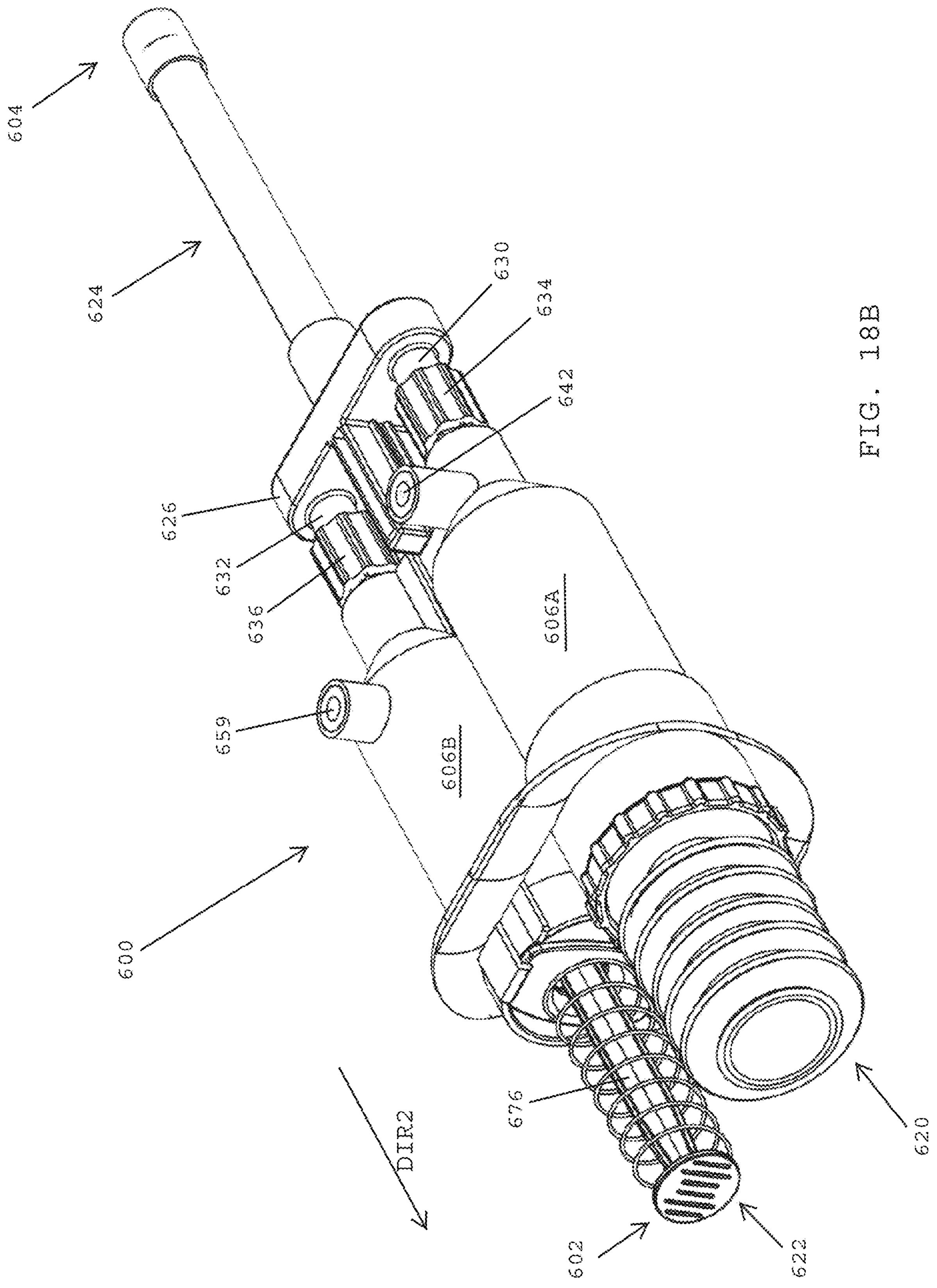
FIG. 18B is another perspective view of the combined powder and liquid delivery device shown in FIG. 18A.
Figure 18C:
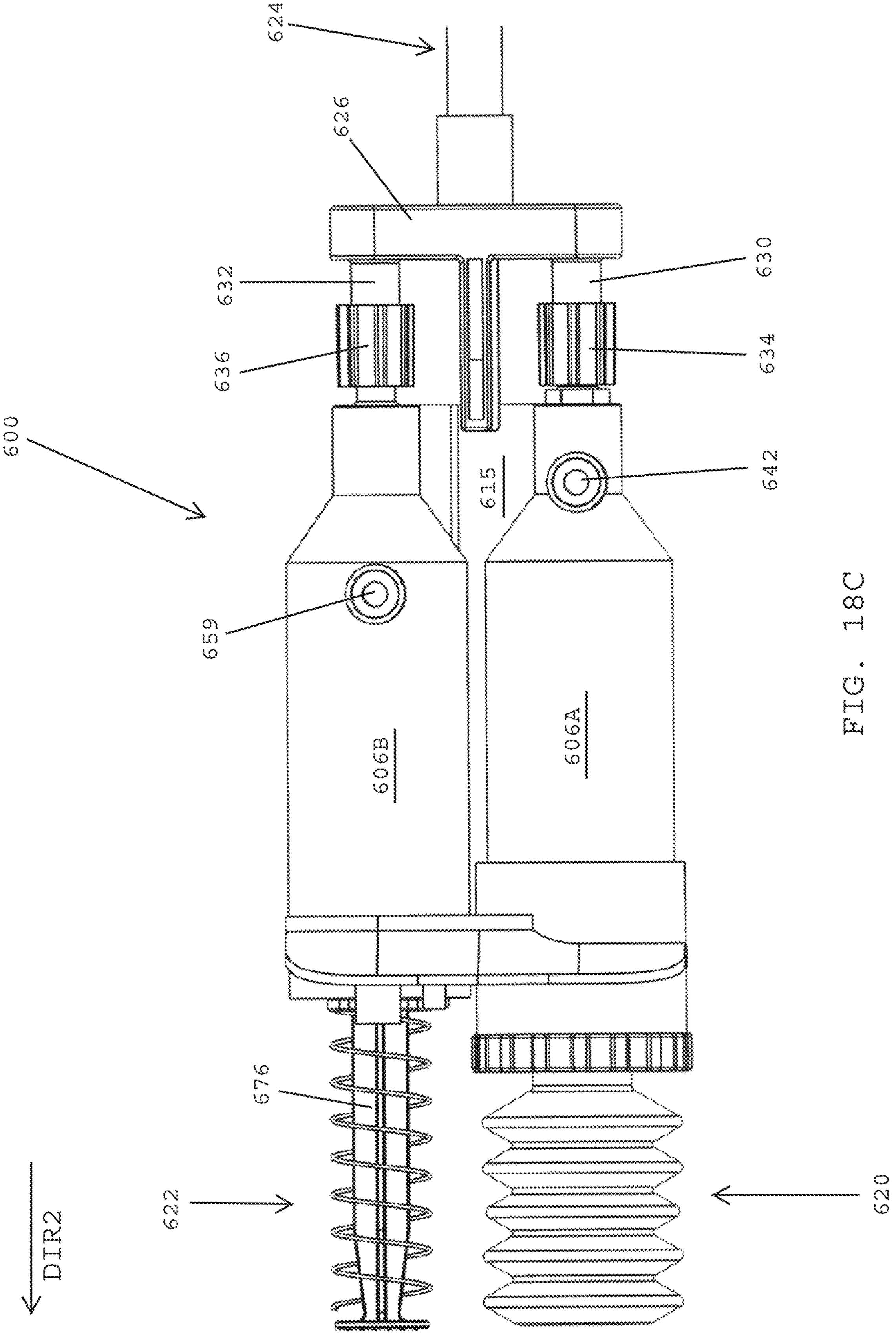
FIG. 18C is a top view of the combined powder and liquid delivery device shown in FIGS. 18A and 18B.

Referring to FIGS. 18A-18C, in one embodiment, a combined powder and liquid delivery device 600 for delivering a powder and a liquid to a surgical site preferably has a proximal end 602 and distal end 604. In one embodiment, the combined powder and liquid delivery device 600 preferably includes a powder housing 606A that is adapted to receive a powder, and a liquid housing 606B that is adapted to receive a liquid. In one embodiment, the combined powder and liquid delivery device 600 desirably includes a powder delivery system 620 that is adapted to deliver a powder (e.g., a dose of a hemostatic powder) from the distal end 604 of the combined powder and liquid delivery device 600, and a liquid delivery system 622 that is adapted to deliver a liquid (e.g., a spray of saline solution) from the distal end 604 of the combined powder and liquid delivery device 600.

In one embodiment, the combined powder and liquid delivery device 600 preferably includes an applicator tip 624 that contains a powder delivery channel (e.g., a powder lumen) that is in fluid in communication with the powder housing 606A and the powder delivery system 620, and a liquid delivery channel (e.g., a liquid lumen) that is in fluid communication with the liquid housing 606B and the liquid delivery system 622. In one embodiment, the combined powder and liquid delivery device 600 desirably includes an applicator tip base 626 having a powder connector 630 and a liquid connector 632, which include segments of the respective powder and liquid delivery channels.

In one embodiment, the combined powder and liquid delivery device 600 preferably includes a delivery device frame 615 that interconnects and supports the powder housing 606A and the liquid housing 606B. In one embodiment, the applicator tip base 626 preferably includes a stabilizing bar 686 that is coupled with a distal end of the delivery device frame 615 for stabilizing the applicator tip 624 to prevent the applicator tip 624 from twisting and/or rotating about its longitudinal axis.

In one embodiment, a first connecting collar 634 secures the powder connector 630 of the applicator tip 624 with the distal end of the powder housing 606A and a second connecting collar 636 secures the liquid connector 632 of the applicator tip 624 with the distal end of the liquid housing 606B.

In one embodiment, the combined powder and liquid delivery device 600 preferably includes a first one-way valve 642 that is in communication with the powder housing 606A for enabling ambient air to be drawn into the powder housing 606A when the powder delivery system 620 is operated to generate a vacuum inside the powder housing 606A.

In one embodiment, the combined powder and liquid delivery device 600 preferably includes a second one-way valve 659 that enables ambient air to be drawn into the liquid housing 606B when a syringe plunger 676 of the liquid delivery system 622 is retracted in a distal direction DIR2.

Figure 19:
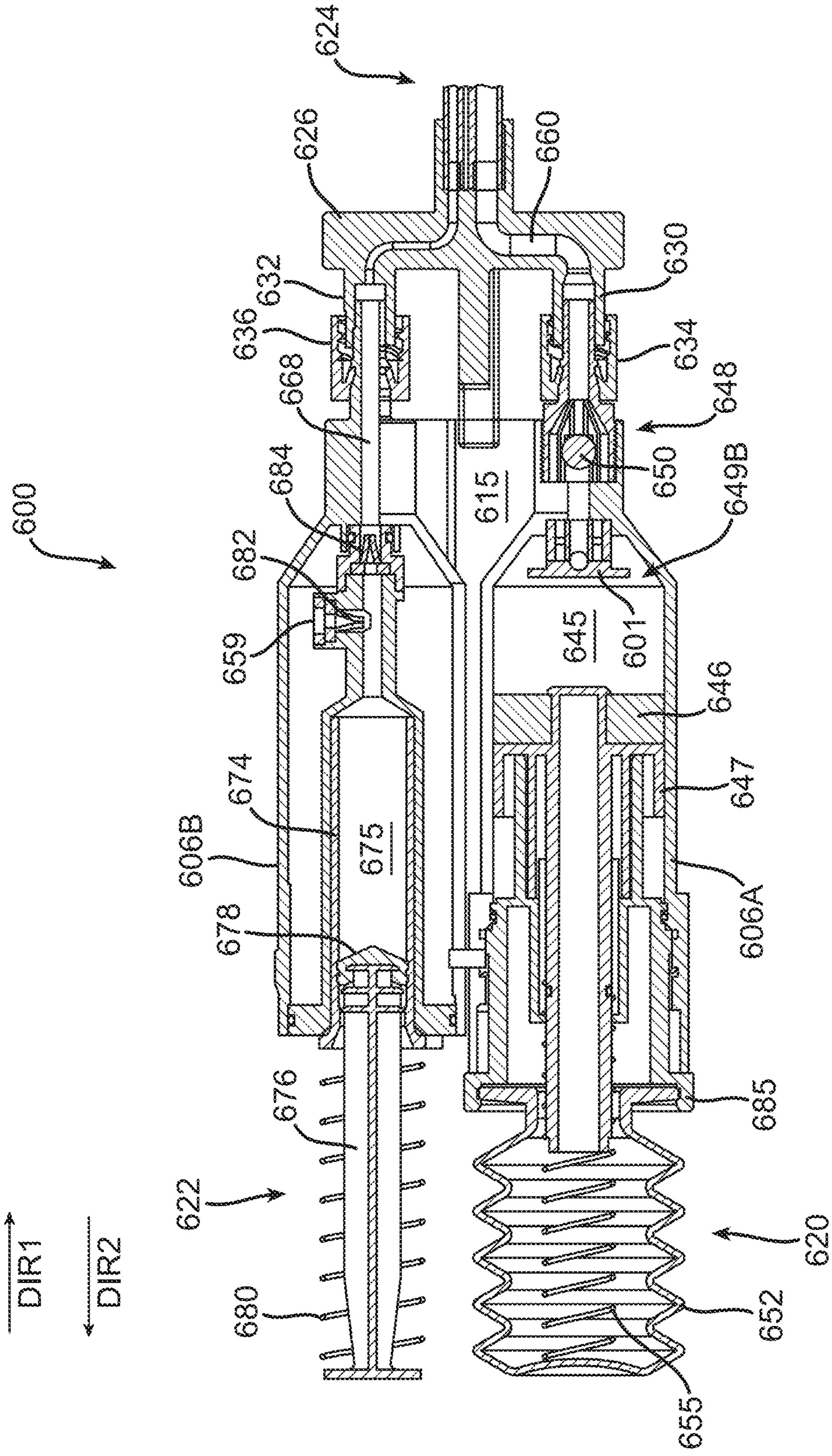
FIG. 19 is a cross-sectional view of a proximal end of the combined powder and liquid delivery device shown in FIGS. 18A-18C.

Referring to FIG. 19, in one embodiment, the powder housing 606A is adapted to receive the powder delivery system 620. The powder delivery system 620 preferably includes a bellows 652, an internal spring 655 that normally urges the bellows 652 into the extended position shown in FIG. 19, a filter holder 647, and a filter 646 that is secured to the filter holder. The powder housing 606A preferably includes a powder chamber 645 that contains powder. In one embodiment, the bellows may be detached (e.g., unscrewed) from the powder housing 606A so that powder may be placed into the powder chamber 645.

In one embodiment, the combined powder and liquid delivery device 600 preferably includes the device frame 615 that supports the powder housing 606A and the liquid housing 606B. In one embodiment, a powder delivery system 620 is assembled with the powder housing 606A and a liquid delivery system 622 is assembled with the liquid housing 606B. In one embodiment, the powder delivery system 620 is activated for dispensing a powder from the distal end of the combined powder and liquid delivery device 600, and the liquid delivery system 622 is activated for dispensing a liquid from the distal end of the combined powder and liquid delivery device 600.

In one embodiment, the powder housing 606A preferably includes a powder chamber 645 that is adapted to receive a powder, which may be delivered from the distal end of the combined powder and liquid delivery device 600 using the powder delivery system 620. In one embodiment, the powder chamber 645 is in fluid communication with the powder delivery channel 660 of the combined powder and liquid delivery device 600. The powder delivery channel 660 desirably extends to the distal end 604 of the applicator tip 624 (FIG. 18A).

In one embodiment, the powder delivery system 620 including the bellows 652 may be detached from the proximal end of the powder housing 606A so that powder may be inserted and/or packed into the powder chamber 645. Once the powder has been packed into the powder chamber 645, the powder delivery system 620 may be reattached to the proximal end of the powder housing 606A. In one embodiment, the powder delivery system 620 preferably includes an end cap 685 that may be releasably secured to the proximal end of the powder housing 606A. In one embodiment, the powder delivery system 620 preferably includes the filter 646 and the filter holder 647 that supports the filter 646 as the filter moves distally (DIR1) within the powder housing 606A.

Figure 20:
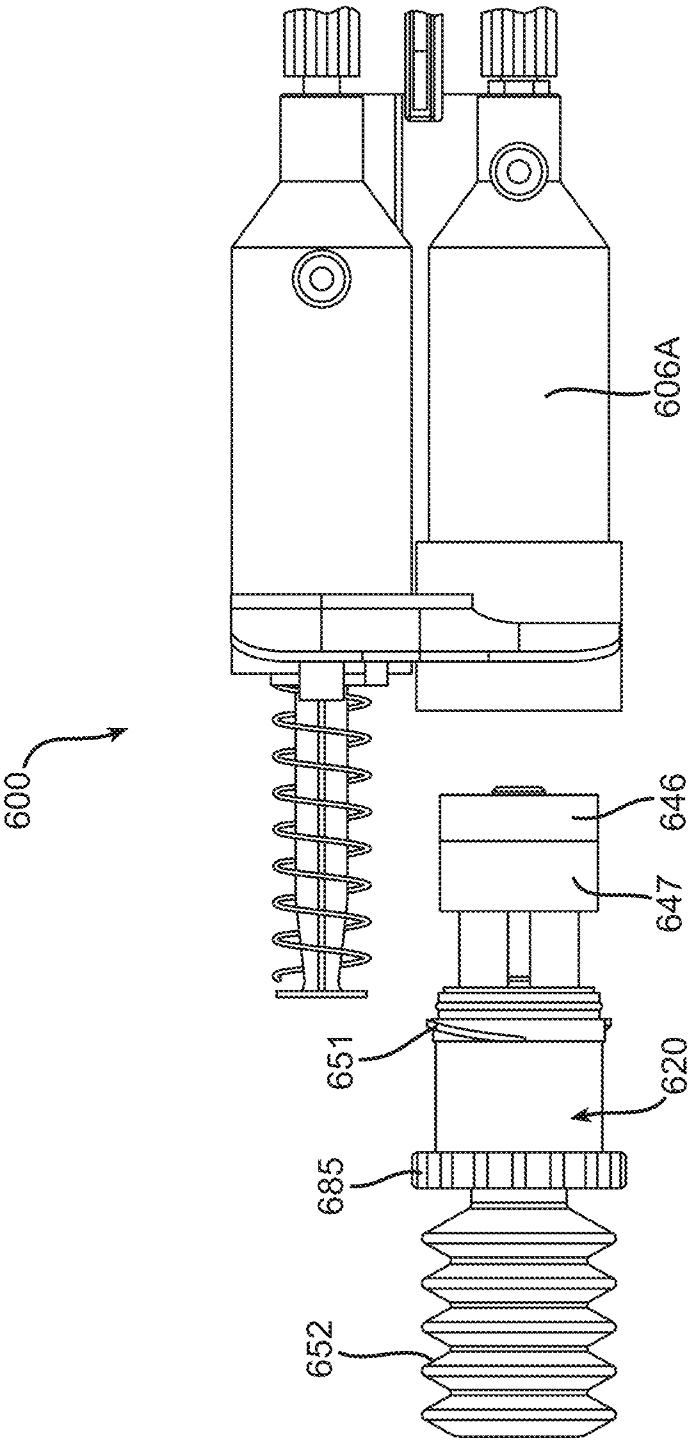
FIG. 20 shows a proximal end of the combined powder and liquid delivery device of FIG. 18C with a bellows portion of a powder delivery system removed from a powder reservoir, in accordance with one embodiment of the present patent application.

In one embodiment, the powder delivery system 620 preferably includes the bellows 652 and an internal bellows spring 655 that urges the bellows 652 to return to the extended position shown in FIGS. 19 and 20.

Figure 21:
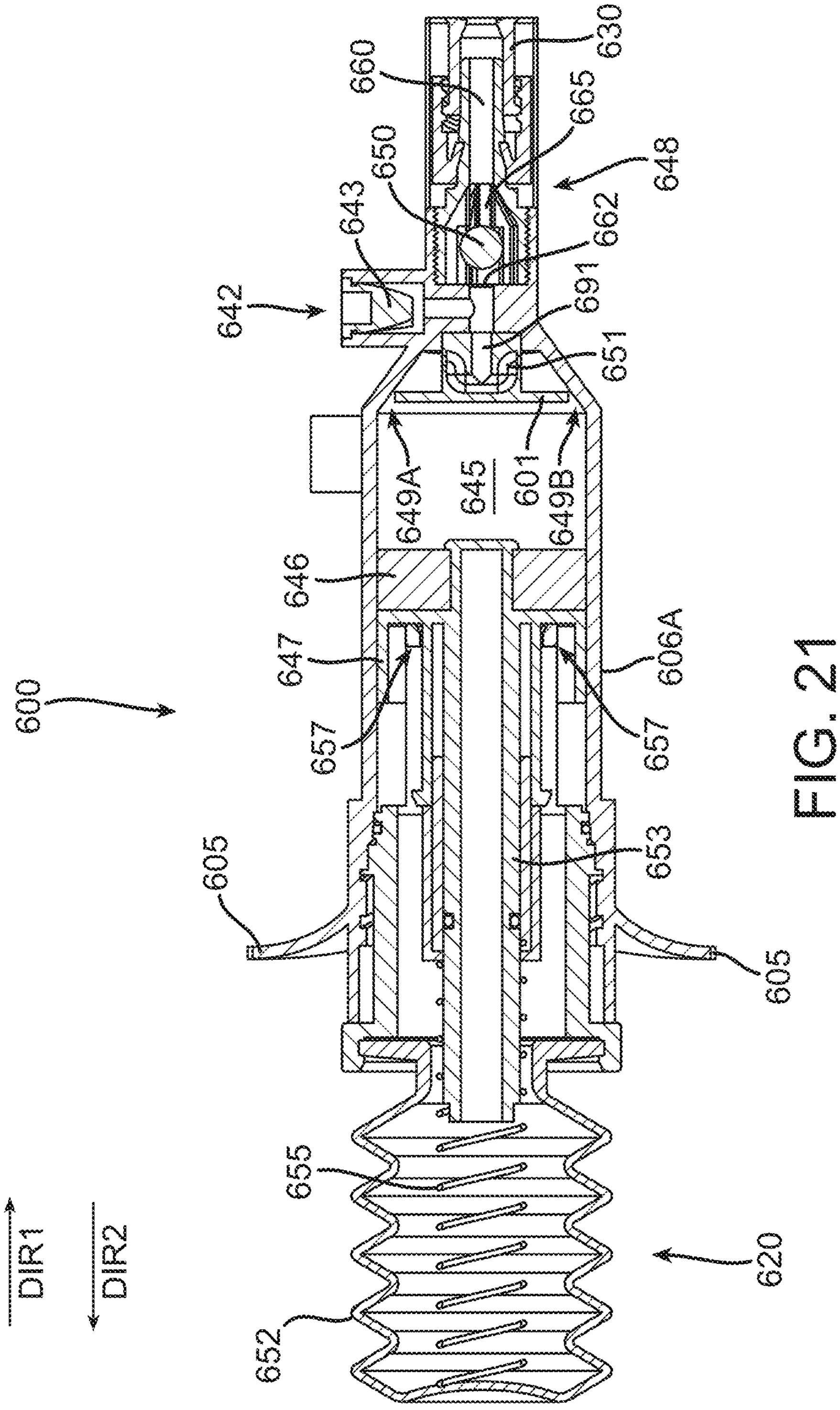
FIG. 21 is a cross-sectional view of a powder delivery system of a powder and liquid delivery device, in accordance with one embodiment of the present patent application.
Figure 22:
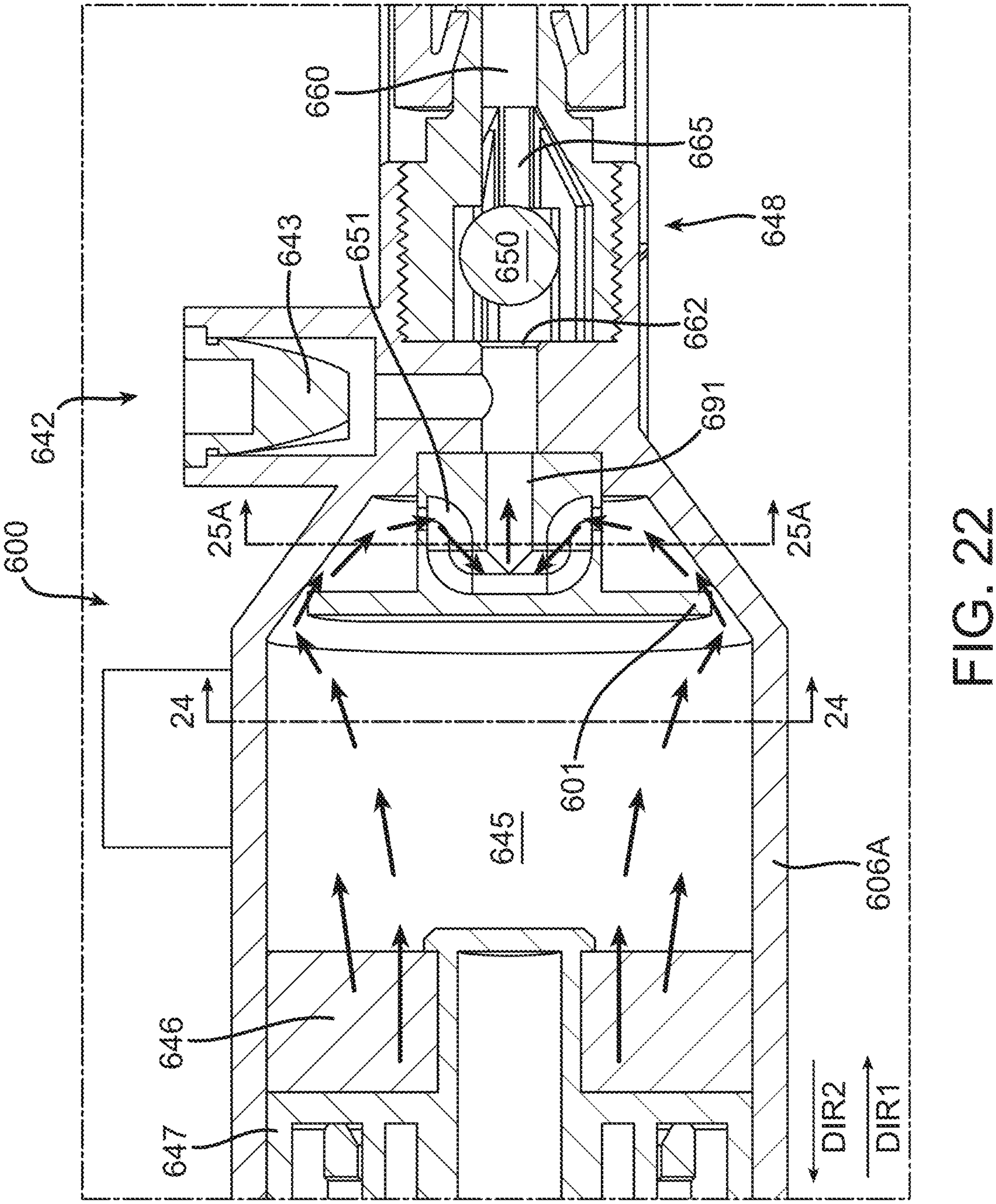
FIG. 22 is a magnified view of a section of the powder delivery system shown in FIG. 21.
Figure 23A:
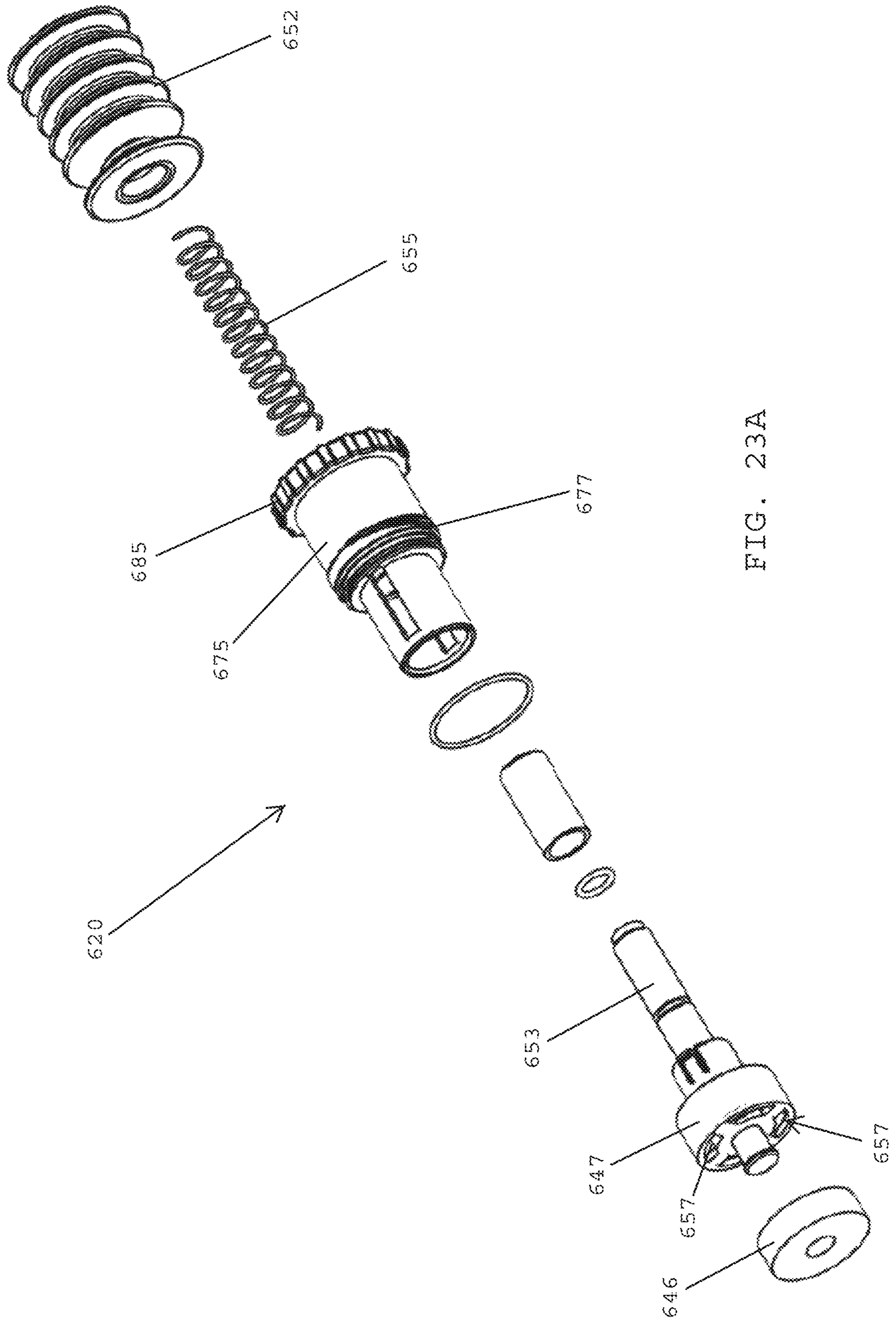
FIG. 23A is an exploded view of the powder delivery system shown in FIGS. 21 and 22.
Figure 23B:
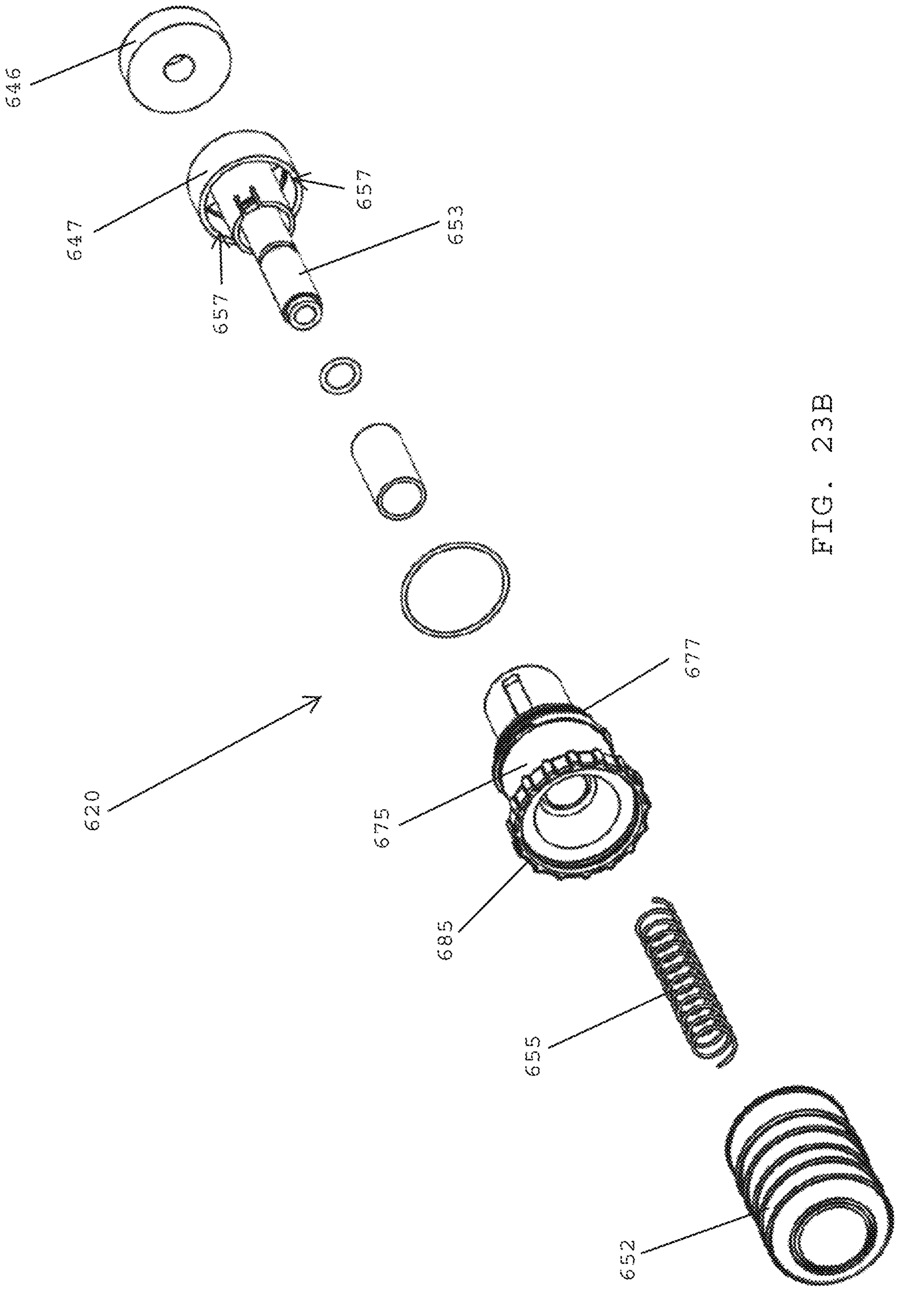
FIG. 23B is another exploded view of the powder delivery system shown in FIGS. 21 and 22.
Figure 24:
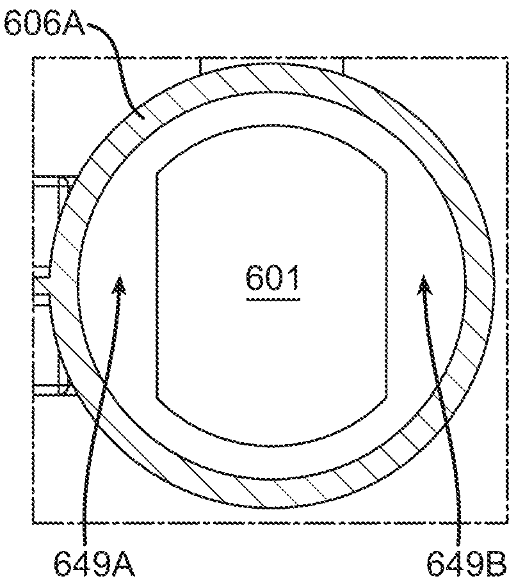
FIG. 24 is a cross-sectional view of a section of the powder delivery system shown in FIG. 22.

Referring to FIGS. 19, 21 and 22, in one embodiment, the powder housing 606A preferably includes an anti-compaction wall 601 that is located adjacent a distal opening at the distal end of the powder housing 606A. The anti-compaction wall 601 preferably defines gaps 649A, 649B (FIG. 24) that are located on opposite sides of the wall 601 that enable powder in the powder chamber 645 to pass around the anti-compaction wall 601 and into the powder delivery channel 660 that is located downstream of a one-way valve 648. The anti-compaction wall 601 preferably prevents the powder within the powder chamber 645 from being packed into an opening at the distal end of the powder housing 606A, which may block the opening and prevent further delivery of powder from the distal end of the applicator tip 624.

In one embodiment, the combined powder and liquid delivery device 600 preferably includes the one-way valve 648 that is located between the distal opening of the powder. housing 606A and a segment of the powder delivery channel 660 that extends into the powder connector 630 of the applicator tip base 626. In one embodiment, the one-way valve 648 preferably includes a ball 650 that is free to move proximally and distally within a central chamber of the one-way valve 648. In one embodiment, the one-way valve may operate in a manner that is similar to the one-way valve shown and described above in FIGS. 2-6.

Referring to FIG. 19, in one embodiment, the combined powder and liquid delivery device 600 preferably includes a liquid delivery system 622 that may be utilized for delivering a liquid from the distal end of the applicator tip 624. In one embodiment, the liquid delivery system 622 preferably includes a syringe barrel 674 that is disposed inside the liquid housing 606B. The liquid delivery system 622 preferably includes a syringe plunger 676 that is disposed inside the syringe barrel 674 and a piston 678 that is secured to a distal end of the syringe plunger 676.

In one embodiment, the syringe barrel 674 preferably surrounds a liquid chamber 675 that is adapted to receive a liquid (e.g., a powder activation fluid).

In one embodiment, the liquid delivery system 622 preferably includes a syringe plunger spring 680 that is configured to urge the syringe plunger to return to the extended position shown in FIGS. 19 and 20.

In one embodiment, the liquid delivery system 622 is preferably adapted to draw a liquid into the liquid chamber 675 of the syringe barrel 674, and then force the liquid from an opening at a distal end of the syringe barrel, whereupon the liquid will flow downstream through the liquid delivery channel 668 for being delivered from the distal end of the applicator tip 624. The combined powder and liquid delivery device 600 preferably include a first one-way valve 682 that enables a liquid to be drawn into the liquid chamber 675 of the syringe barrel 674 when the syringe plunger 676 is retracted in the proximal direction DIR2. As the syringe plunger 676 and the piston 678 are retracted in the proximal direction DIR2, a vacuum is created within the liquid chamber 675 of the syringe barrel 674 for drawing liquid through the first one-way valve 682 and into the liquid chamber 675.

In one embodiment, as the syringe plunger 676 is depressed in the distal direction DIR1, the liquid within the liquid chamber 675 of the syringe barrel 674 is forced to flow in the distal direction DIR1 for passing through the second one-way valve 684 and into the liquid delivery channel 668 of the combined powder and liquid delivery device 600. The liquid preferably travels through the liquid connector 632 of the applicator tip base 626 of the applicator tip 624.

Referring to FIG. 20, in one embodiment, the powder delivery system 620 may be detached and removed from the opening at a proximal end of the powder housing 606A of the combined powder and liquid delivery device 600. The powder delivery system 620 preferably includes the end cap 685 that may be utilized for securing the powder delivery system 620 with a proximal end of the powder housing 606A. In one embodiment, the powder delivery system 620 preferably includes the bellows 652, the filter 646, the filter holder 647, and external threads 651 that are adapted to engage internal threads within the powder housing 606A for securing the powder delivery system 620 inside the powder housing 606A.

In one embodiment, the powder delivery system 620 may be removed from the powder housing 606A so that powder may be disposed (e.g., packed) within the powder chamber 645 (FIG. 19) of the powder housing 606A. In one embodiment, after the powder is disposed within the powder chamber of the powder housing 606A, the powder delivery system 620 may be reinserted into the powder housing 606A and secured to the powder housing, such as by using the threads 651.

Referring to FIG. 21, in one embodiment, as the bellows spring 655 expands the bellows 652 into an extended position, air is drawn through the first air inlet 642 and the one-way valve 643 for filling the interior of the bellows 652. The air that flows through the one-way valve 643 preferably travels in a generally distal direction through a tortuous pathway 651 (FIG. 22), around the gaps 649A, 649B (FIG. 19) between the outer perimeter of the powder anti-compaction wall 601 (FIG. 24) and the inner surface of the powder housing 606A, and through the filter 646 for filling the interior of the bellows 652.

In one embodiment, as air is drawn into the bellows 652, a vacuum is generated within the powder chamber 645 of the powder housing 606A. The vacuum pulls the ball 650 of the one-way valve 648 so that the ball seats against a proximal sealing surface 662 of the one-way valve 648 for preventing any moisture within the powder delivery channel 660 from reaching the powder chamber 645. The one-way valve 648 also preferably prevents the moisture from entering the tortuous pathway 651 or the powder chamber 645, which could clog the combined powder and liquid delivery device 600.

In one embodiment, when the bellows 652 is compressed in the distal direction DIR1, the filter holder 647 and the filter 646 move distally for pushing the powder within the powder chamber 645 toward the distal end of the powder housing 606A. The high-pressure air generated by the compressed bellows 652 preferably flows distally through the filter 646 for forcing the powder to flow around the gaps 649A, 649B (FIG. 19) surrounding the powder anti-compaction wall 601. The distally flowing air and powder flow through the tortuous pathway 651, around the ball 650 of the one-way valve 648, and into the powder delivery channel 660 for being delivered from the distal end of the applicator tip 624 (FIG. 19) of the combined powder and liquid delivery device 600.

As the high-pressure air flows distally (DIR1) through the one-way valve 648, the high-pressure air forces the ball 650 against the ball stop 665 (FIG. 22), which allows the air and powder to flow around the ball 650 for enabling the powder to flow into the powder delivery channel 660.

Figure 25A:
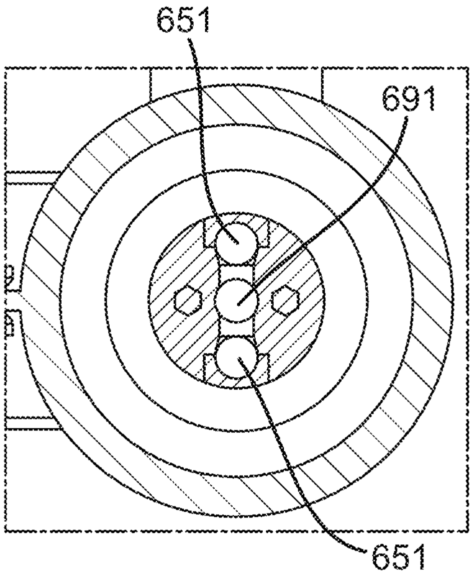
FIG. 25A is a cross-sectional view of a section of the powder delivery system shown in FIG. 22.
Figure 25B:
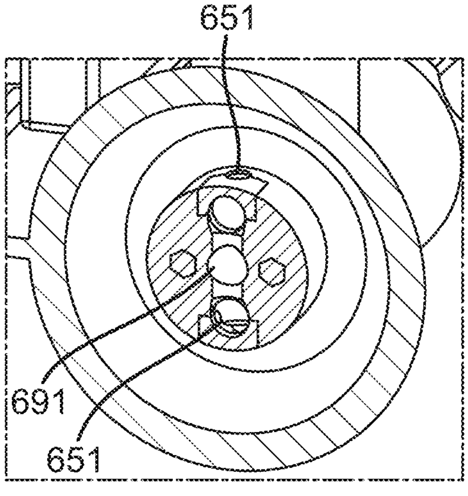
FIG. 25B is a perspective view of the cross-sectional view shown in FIG. 25A.
Figure 25C:
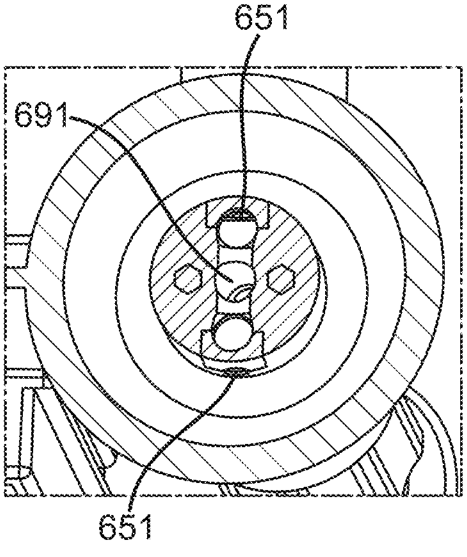
FIG. 25C is another perspective view of the cross-sectional view shown in FIG. 25A.

Referring to FIGS. 21, 22, 23A, and 23B, in one embodiment, the powder delivery system 620 of the combined powder and liquid delivery device 600 preferably includes the powder housing 606A (FIG. 21) having a proximal end and a distal end. The powder delivery system 620 preferably includes a manual air pump, such as a compressible bellows 652, which is mounted onto the proximal end of the powder housing 606A. The powder housing preferably has a hand grip 605 (FIG. 21) at the proximal end thereof. The powder delivery system 620 preferably includes a filter holder 647 (FIG. 21) that is positioned within the powder housing 606A and a filter 646 that is mounted on the filter holder 647. The filter holder 647 and the filter 646 are mounted slidably within the powder housing 606A and are configured for advancing together toward the distal end of the powder housing 606A. The distal end of the powder housing 606A preferably has a powder exit opening 691 (FIGS. 25A-25C). Proximal to the powder exit opening 691 (FIGS. 21 and 22) is mounted the powder anti-compaction wall 601 (FIGS. 21 and 22). The tortuous pathway 651 (FIGS. 21 and 22) preferably extends between a distal side of the powder anti-compaction wall 601 and the powder exit opening 691.

In one embodiment, the filter holder 647 preferably has a plunger stem 653 that extends proximally from the filter holder 647 toward the proximal end of the powder housing 606A. The bellows spring 655 is positioned on the plunger stem 653. The bellows spring 655 is preferably positioned between the bellows 652 and the filter holder 647, and is partially inside the bellows 652, and more specifically between the top, free end of the bellows 652 and the filter holder 647.

In one embodiment, the filter holder 647 and the filter 646 are coaxially and slidably moveable within the powder housing 606A. In one embodiment, the filter holder 647 preferably has one or more apertures 657 (FIGS. 23A and 23B) extending therethrough that provide a path for air or gas to flow through the filter holder 647.

In one embodiment, the filter 646 (e.g., a microporous filter) snugly and slidably fits within the powder housing 606A and moves together with the filter holder 647. A portion of the powder housing 606A that is located between the filter 646 and the powder exit opening 691 of the powder housing defines the powder chamber 645, which may be filled with a powder (not shown). In one embodiment, the volume of the powder chamber 645 preferably decreases as the filter holder 647 and the filter 646 advance toward the distal end of the powder housing 606A.

In one embodiment, the powder housing 606 preferably includes the tortuous pathway 651 (FIGS. 21 and 22) for the powder and air exiting the powder chamber 645. In one embodiment, the tortuous pathway 651 is a channel having several bends and starting with an orifice located within the powder chamber 645. The tortuous pathway 651 results in turning of the direction along which the air and the powder are advancing within the combined powder and liquid delivery device 600, particularly turning from travelling generally from a proximal toward a distal direction, i.e., from the powder chamber 645 to the powder exit opening 691 (FIGS. 25A-25C), to travelling a short distance in another direction, such as in a sideways direction (i.e., perpendicular to the longitudinal axis of the powder housing) or in an opposite direction (i.e., rearwards, from the distal end toward the proximal end of the powder housing). The change in the direction along which the air and powder advance through the powder housing 606A, the powder chamber 645, and the tortuous pathway 651 is shown schematically by arrows (FIG. 22), which indicate air and powder advancement from the proximal end toward the distal end of the powder housing 606A, with a brief intermittent change in the direction when advancing through the tortuous pathway 651.

In one embodiment, the tortuous pathway 651 preferably prevents powder (not shown) in the powder chamber 645 from exiting the combined powder and liquid delivery device 600 via the powder delivery channel 660 when no air flow is present (e.g., prevents the loss of powder when the combined powder and liquid delivery device 600 is pointed down, especially when the combined powder and liquid delivery device is subject to shaking or vibration or any variable acceleration movements). The tortuous pathway 651 prevents unintentional expression of small quantities of powder from the powder chamber 645, while allowing powder expression when driven by air flow.

Referring to FIGS. 21 and 22, in one embodiment, the flow of air with entrained powder from the powder chamber 645 is schematically indicated by arrows. The bellows 652 is in fluid communication with the exit opening 691 through the one or more apertures 657 (FIGS. 23A and 23B) in the filter holder 647, the filter 646, and the tortuous pathway 651. In one embodiment, upon compression of the bellows 652, air moves from the bellows 652 via the one or more apertures 657 (FIGS. 23A and 23B) of the filter holder 647, and through the filter 646 into the powder chamber 645. From the powder chamber 645, as schematically indicated by the arrows (FIG. 22), the powder and air stream enter the tortuous pathway 651 and then move from the tortuous pathway 651 into the powder exit opening 691 of the powder housing 606A.

In one embodiment, upon applying pressure on the free end of the bellow 652, the bellows 652 compresses, which generates positive air pressure inside the bellows. The air flows distally through the one or more apertures 657 (FIGS. 23A and 23B) of the filter holder 647, through the filter 646 and into the powder chamber 645. From the powder chamber 645, the powder and air stream are expressed from the device via the one-way valve 648 and the powder delivery channel 660 (FIG. 22).

In one embodiment, upon release of pressure on the bellows 652, the bellows spring 655 returns the bellows to an uncompressed state, creating a vacuum inside the bellows 652. Air or gas is drawn into the bellows 652, with the air entering the powder housing 606A via the one-way valve 643 (FIG. 22). Under vacuum, the air flows proximally through the tortuous pathway 651, around the powder anti-compaction wall 601, through the powder chamber 645, through the filter 646, and through the one or more apertures 657 (FIG. 23A) of the filter holder 657 for filling the interior of the bellows 652. The filter 646 prevents the powder from reaching the bellows so that the bellows 652 is substantially free of powder throughout the expression.

In one embodiment, the powder chamber 645 is maintained so that the volume of the powder chamber 645 is substantially filled with powder, with substantially no free air space or minimal free air space. The inventors of U.S. Pat. No. 10,507,293, the disclosure of which is hereby incorporated by reference herein, discovered that such an arrangement results in better uniformity of powder expression throughout an expression cycle, i.e., from when the combined powder and liquid delivery device 600 is fully charged with powder to when the powder chamber 645 has been fully emptied of all remaining powder, as well as resulting in better directional expression uniformity, i.e., in minimal differences between the expression of powder with the applicator tip directed horizontally relative to being directed vertically.

In one embodiment, the bellows spring 655 serves as a compressible advancer of the filter holder 647 (FIG. 21) and the filter 646. When the bellows 652 is depressed, the bellows generates a flow of positive air pressure for expressing powder from the distal end of the combined powder and liquid delivery device 600. Simultaneously, the top or free end of the bellows 652 is compressing the bellows spring 655, which, in turn, applies pressure on the filter holder 647 and the filter 646, thereby causing the filter holder 647 and the filter 646 to move in the distal direction DIR1 for decreasing the volume of the powder chamber 645 as the powder is expressed from the combined powder and liquid delivery device 600.

In one embodiment, during each depression or compression of the bellows 652, which generates air flow and powder expression from the powder chamber 645, the filter holder 647 and the filter 646 are simultaneously driven toward the distal end of the powder housing 606A by the bellows spring 655, which is depressed upon compression of the bellows 652. Thus, upon each expression of the powder from the combined powder and liquid delivery device 600, the filter holder 647 and the filter 646 advance distally to take up the space within the powder chamber 645 that is freed by the expressed powder. This action results in the volume of the powder chamber 645 being constantly adjusted to correspond to the volume of the powder remaining inside the powder chamber 645.

In one embodiment, upon release of the bellows 652 so that it is no longer being compressed, the compression on the spring 655 is released so that the spring is free to expand in the proximal direction DIR2 (FIG. 21), without pulling on the filter holder 647 and the attached filter 646. In one embodiment, the spring 655 is not attached to the bellows 652, resulting in the spring 655 not being pulled proximally upon release of pressure on the bellows 652 and expansion of the bellows into an expanded, uncompressed state.

In one embodiment, the filter holder 647 and the filter 646 are configured for snugly and slidably fitting inside the powder housing 606A. After each cycle, the plunger 653 and the filter 646 remain in the position furthest advanced during the latest cycle of powder expression. When the pressure on the bellows 652 is removed and the bellows expands for drawing air into the bellows, the filter holder 647 and the filter 646 do not move in the proximal direction DIR2, but instead maintain the closest position to the distal end of the powder housing 606A that was achieved during the prior powder expression cycle. The frictional engagement of the filter holder 647 and the filter 646 against the inner surface of the powder housing 606A preferably prevents easy movement of the filter holder 647 and the filter 646 in a rearward direction, i.e., in the proximal direction DIR2.

Depression of the bellows 652 results in simultaneous generation of gas pressure within the combined powder and liquid delivery device 600 and pressure on the spring 655, which, in turn, forces the filter holder 647 with the filter 646 to advance distally (DIR1) within the powder chamber 645 to take up any space freed by the powder expressed from the powder chamber 645.

In one embodiment, prior to any expression of the powder, the spring 655 generates no or very little pressure on the powder in the powder chamber 645. Because there is no or very little constant pressure from the spring 655 on the powder in the powder chamber 645, potential agglomeration and caking of powder are prevented.

In one embodiment, the spring 655 is positioned on the plunger stem 653. The spring 655 is preferably located between the top or free end of the bellows 652 and the proximal side of the filter holder 647. In one embodiment, a proximal end of the spring 655 touches the top or free end of the bellows 652. In one embodiment, the proximal end of the spring may be positioned a distance from the top of the bellows 652 (e.g., about 0-20 mm)

FIGS. 21 and 22 show the position of the spring 655, the filter holder 647, the filter 646, and the powder chamber 645 after one or more powder expressions. Upon expression of the powder from the powder chamber 645, the volume of the powder chamber 645 decreases with the filter holder 647 and the filter 646 advancing distally within the powder housing 606A and taking up freed space within the powder chamber 645. In one embodiment, the proximal end of the spring 655 may be positioned at a distance from the top or free end of the bellows 652, with the distance increasing after each powder expression.

Figure 26:
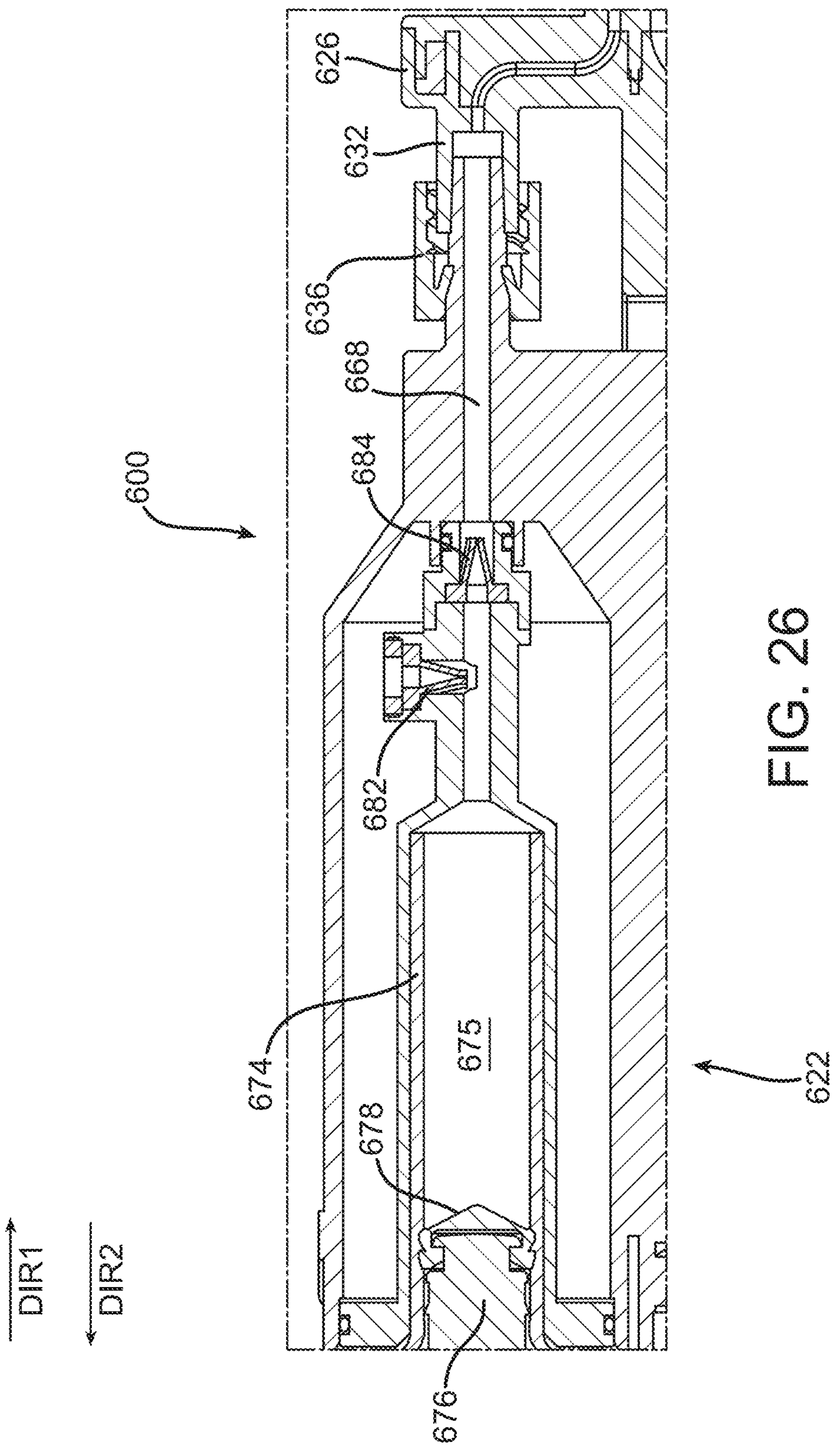
FIG. 26 is a cross-sectional view of a liquid delivery system of the combined powder and liquid delivery device shown in FIGS. 18A-18C.

Referring to FIG. 26, in one embodiment, when the syringe plunger 676 and the piston 678 of the liquid delivery device are retracted in the proximal direction DIR2, a vacuum is generated within the liquid chamber 675 of the syringe barrel 674. The vacuum within the liquid chamber 675 draws a liquid through the first one-way valve 682. After passing through the first one-way valve 682, the liquid fills the liquid chamber 675 of the syringe barrel 674. In one embodiment, when the syringe plunger 676 is depressed in the distal direction DIR1, the piston 678 of the liquid delivery system 622 (FIG. 19) forces the liquid from an opening at the distal end of the syringe barrel 674. The liquid flowing in the distal direction DIR1 preferably passes through the second one-way valve 684 for entering the liquid delivery channel 668. The distally flowing liquid preferably passes through the liquid connector 632 of the applicator tip base 626 of the applicator tip 624 (FIG. 19) for being delivered to the distal end of the combined powder and liquid delivery device 600.

Figure 27A:
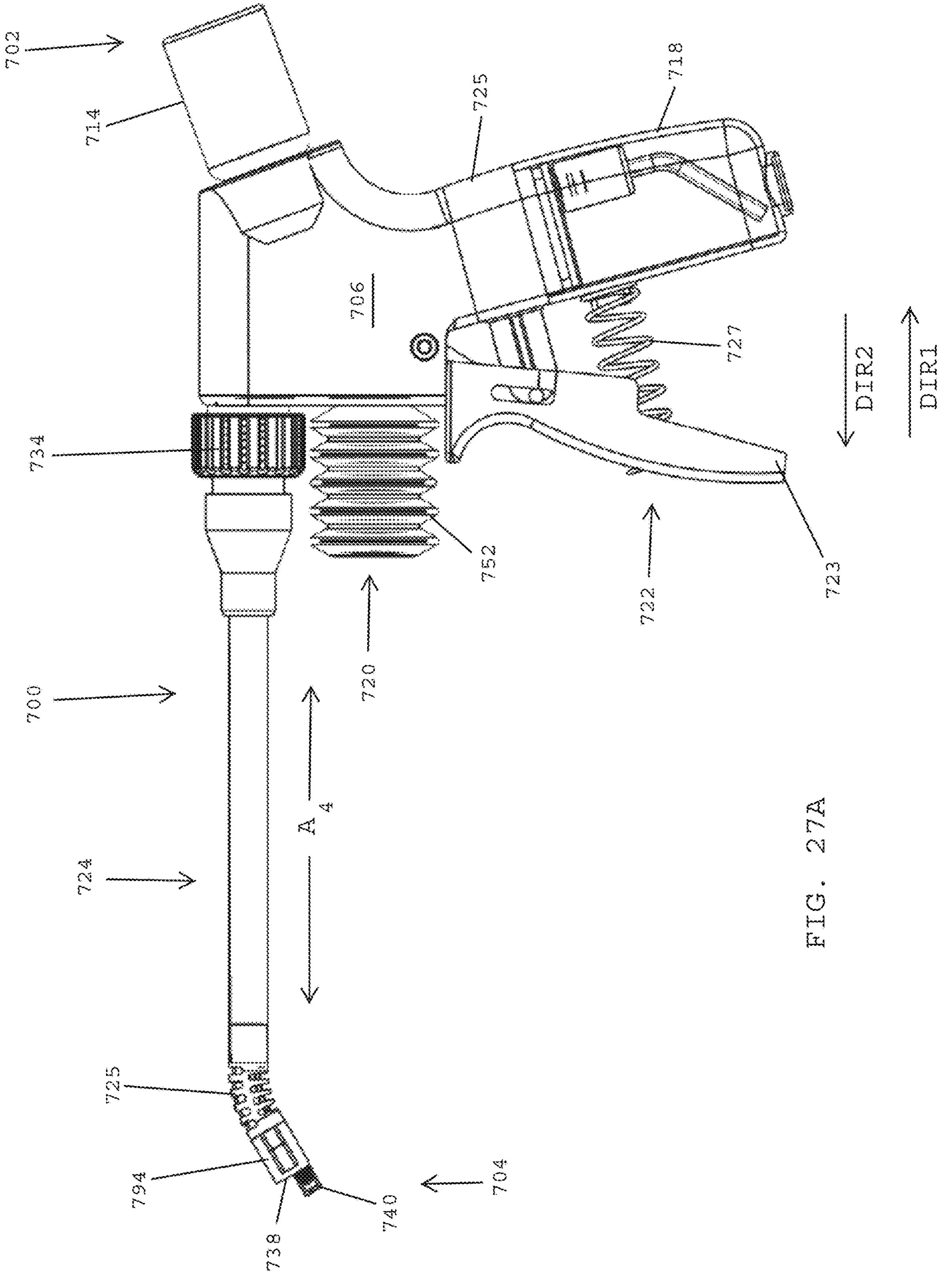
FIG. 27A is a side view of a powder and liquid delivery device, in accordance with one embodiment of the present patent application.
Figure 27B:
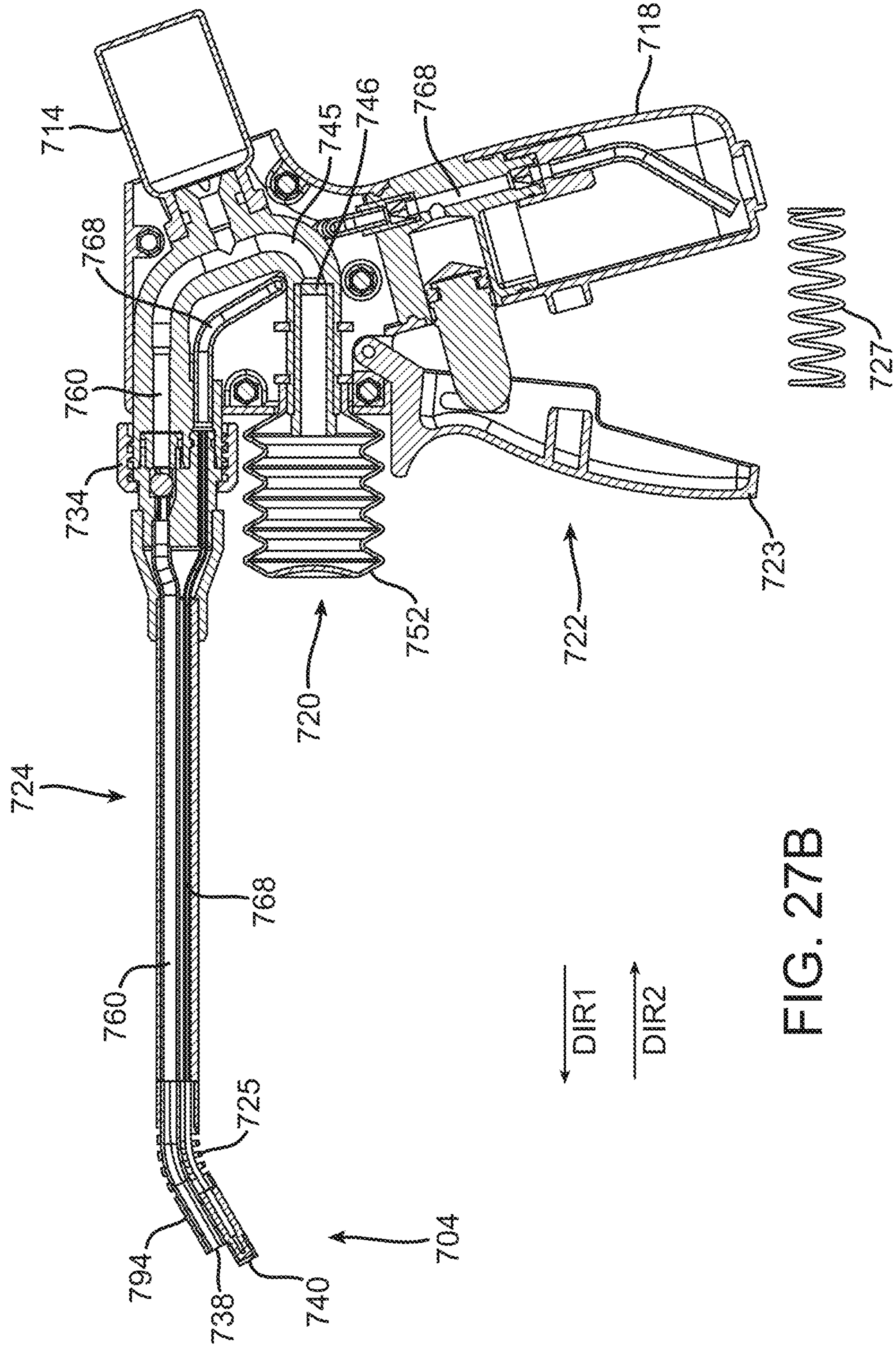
FIG. 27B is a cross-sectional view of the combined powder and liquid delivery device shown in FIG. 27A.

Referring to FIGS. 27A and 27B, in one embodiment, a combined powder and liquid delivery device 700 for delivering a powder and a liquid from a distal end thereof preferably has a proximal end 702 and a distal end 704. In one embodiment, the combined powder and liquid delivery device 700 preferably includes a delivery device housing 706 that has a handle 725 and a trigger 723 that is pivotally connected with the housing 706 for operating a liquid delivery system 722.

In one embodiment, the combined powder and liquid delivery device 700 desirably includes a first vial 714 (e.g., a powder vial; a hemostatic powder vial) that is configured for being connected with the delivery device housing 706 for supplying a powder, and a liquid tank 718 that is configured for being assembled with a lower end of the handle 725 for supplying a liquid.

In one embodiment, the combined powder and liquid delivery device 700 preferably includes an applicator tip 724 that is coupled to a distal end of the device housing 706 via a connecting collar 734. The applicator tip 724 is preferably adapted for delivering a powder and a liquid from the distal end 704 of the combined powder and liquid delivery device 700. In one embodiment, the applicator tip 724 preferably includes a dual-lumen powder and liquid connector 794 that joins together the powder delivery channel 760 and the liquid delivery channel 768 of the combined powder and liquid delivery device 700. In one embodiment, the applicator tip 724 includes a powder delivery opening 738 for delivering the powder from the distal end of the combined powder and liquid delivery device. The applicator tip 724 also preferably includes a liquid spray cup 740 for delivering the liquid from the distal end of the combined powder and liquid delivery device.

In one embodiment, the applicator tip 724 preferably includes a flexible section 725 that enables the dual-lumen powder and liquid connector 794 and/or a distal end of the applicator tip 724 to be angulated relative to a proximal section of the applicator tip that extends along the axis $A_4$ (FIG. 27A). In one embodiment, the combined powder and liquid delivery device 700 preferably includes a powder delivery system 720 that is configured for drawing a powder into the device housing 706 and dispensing the powder from the distal end 704 of the combined powder and liquid delivery device. In one embodiment, the combined powder and liquid delivery device 700 preferably includes the liquid delivery system 722 that is adapted to draw a liquid from the liquid tank 718 and dispense the liquid from the distal end 704 of the combined powder and liquid delivery device.

Referring to FIG. 27B, in one embodiment, a dose of powder is drawn from the powder vial 714 into a powder chamber 745 of the powder delivery channel 760 when the bellows 752 expands in the distal direction designated DIR1. When the bellows 752 is compressed in the proximal direction DIR2, the dose of powder that is within the powder chamber 745 of the powder delivery channel 760 is forced distally through the powder delivery channel 760 for being delivered from the powder delivery opening 738 at the distal end 704 of the applicator tip 724.

In one embodiment, when the lower end of a trigger 723 of the liquid delivery system 722 moves in the distal direction DIR1, a liquid stored in the liquid tank 718 is drawn into the liquid delivery channel 768 of the device housing 706. When the trigger 723 is compressed toward the handle 725 in the proximal direction DIR2, the liquid within the liquid delivery channel 768 is forced downstream through the applicator tip 724 for being sprayed from the liquid spray cup 740 located at the distal end 704 of the applicator tip 724.

Figure 28:
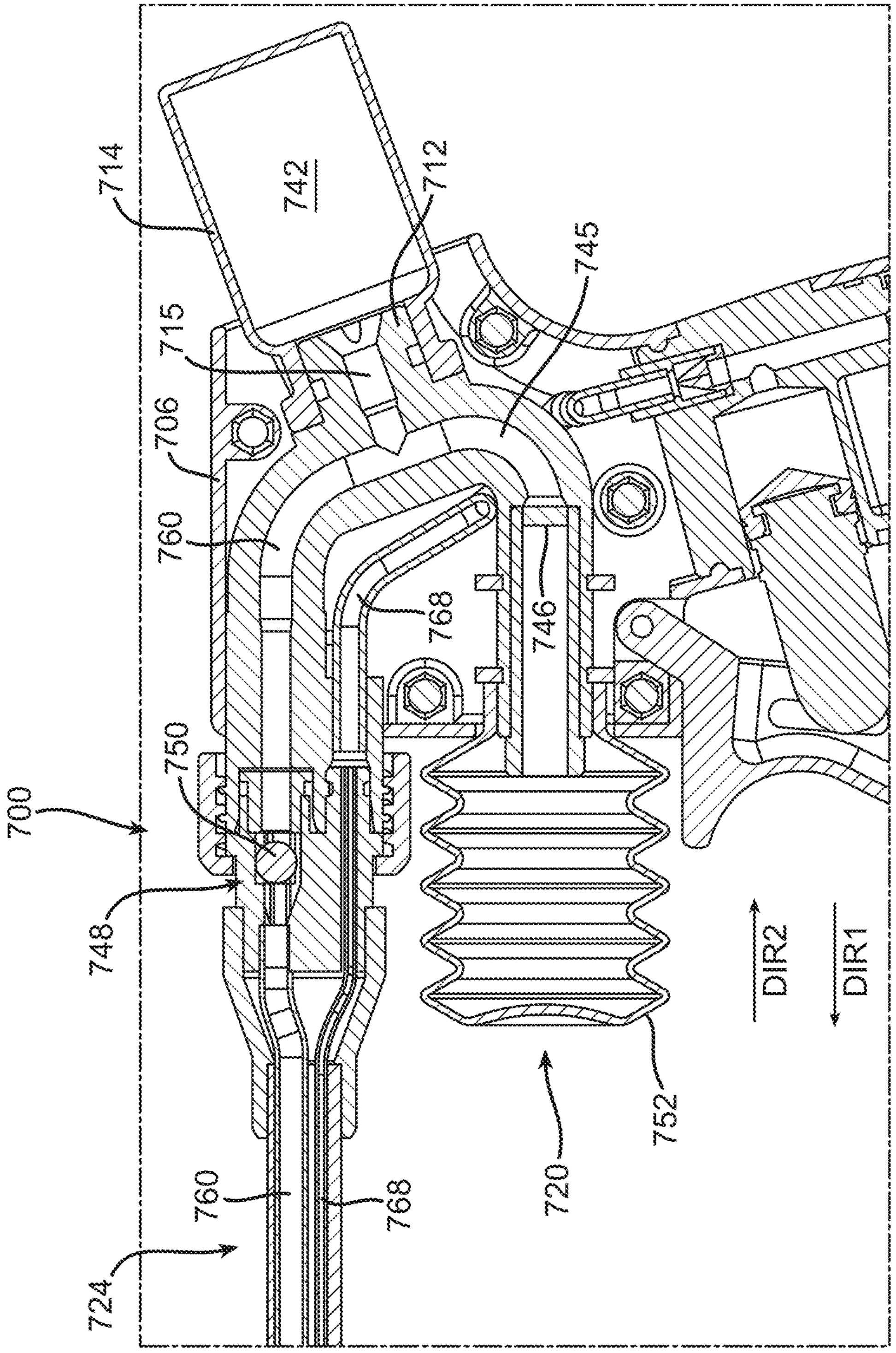
FIG. 28 is a cross-sectional view of a powder delivery system of the combined powder and liquid delivery device shown in FIGS. 27A and 27B.

Referring to FIG. 28, in one embodiment, the combined powder and liquid delivery device 700 preferably includes the powder delivery system 720 for first drawing powder from the powder compartment 742 of the powder vial 714 into the powder chamber 745, and then dispensing the powder via the powder delivery channel 760 from a distal end of the applicator tip 724. In one embodiment, the device housing 706 includes a powder vial connector 712 that is adapted to mate with an open end of the powder vial 714, which contains powder within the powder chamber 742 of the powder vial 714. The powder connector 712 preferably includes a powder inlet port 715 that provides a pathway between the powder compartment 742 of the powder vial 714 and the powder chamber 745.

In one embodiment, the powder delivery system 720 of the combined powder and liquid delivery device 700 preferably includes a filter 746 located between the bellows 752 and the powder chamber 745. The filter 746 preferably allows air to pass therethrough, however, the filter 746 prevents the powder from passing therethrough and into the bellows 752 as air flows into and out of the bellows 752.

In one embodiment, the powder vial 714 containing a powder within the powder compartment 742 is connected to the powder connector 712 of the delivery device housing 706. so that the powder may be drawn through the powder inlet port 715 and into the powder chamber 745 of the powder delivery channel 760. In one embodiment, when the bellows 752 is expanded in the distal direction DIR1, a vacuum is created by the expanding bellows 752, which draws air through the filter 746 for filling the bellows 752. The action of the powder delivery system 720 preferably generates a vacuum within the powder chamber 745, which draws powder from the powder compartment 742 of the powder vial 714, through the powder inlet port 715, and into the powder chamber 745 of the powder delivery channel 760.

In one embodiment, as the bellows 752 creates the vacuum within the powder delivery channel 760, the ball 750 of the one-way valve 748 prevents any moist air in the powder delivery channel 760 from being drawn into the portion of the powder delivery channel 760 that is located within the device housing 706, thereby minimizing the likelihood of moisture reacting with the powder within the powder chamber 745 and the proximal end of the powder delivery channel 760, which could clog the device.

In one embodiment, after the expanding bellows 752 has generated a vacuum for drawing powder into the powder chamber 745, the bellows 752 may be compressed in the proximal direction designated DIR2 for generating high pressure air that forces the powder within the powder chamber 745 to flow downstream through the powder delivery channel 760, flow around the ball 750 of the one-way valve 748, and flow into a distal section of the powder delivery channel 760 that is located within the applicator tip 724 of the combined powder and liquid delivery device 700.

In one embodiment, the applicator tip 724 preferably includes both the powder delivery channel 760 and a liquid delivery channel 768 (FIG. 28). The liquid delivery channel 768 is desirably maintained separate and apart (e.g., isolated) from the powder delivery channel 760 along the length of the applicator tip 724.

Figure 29:
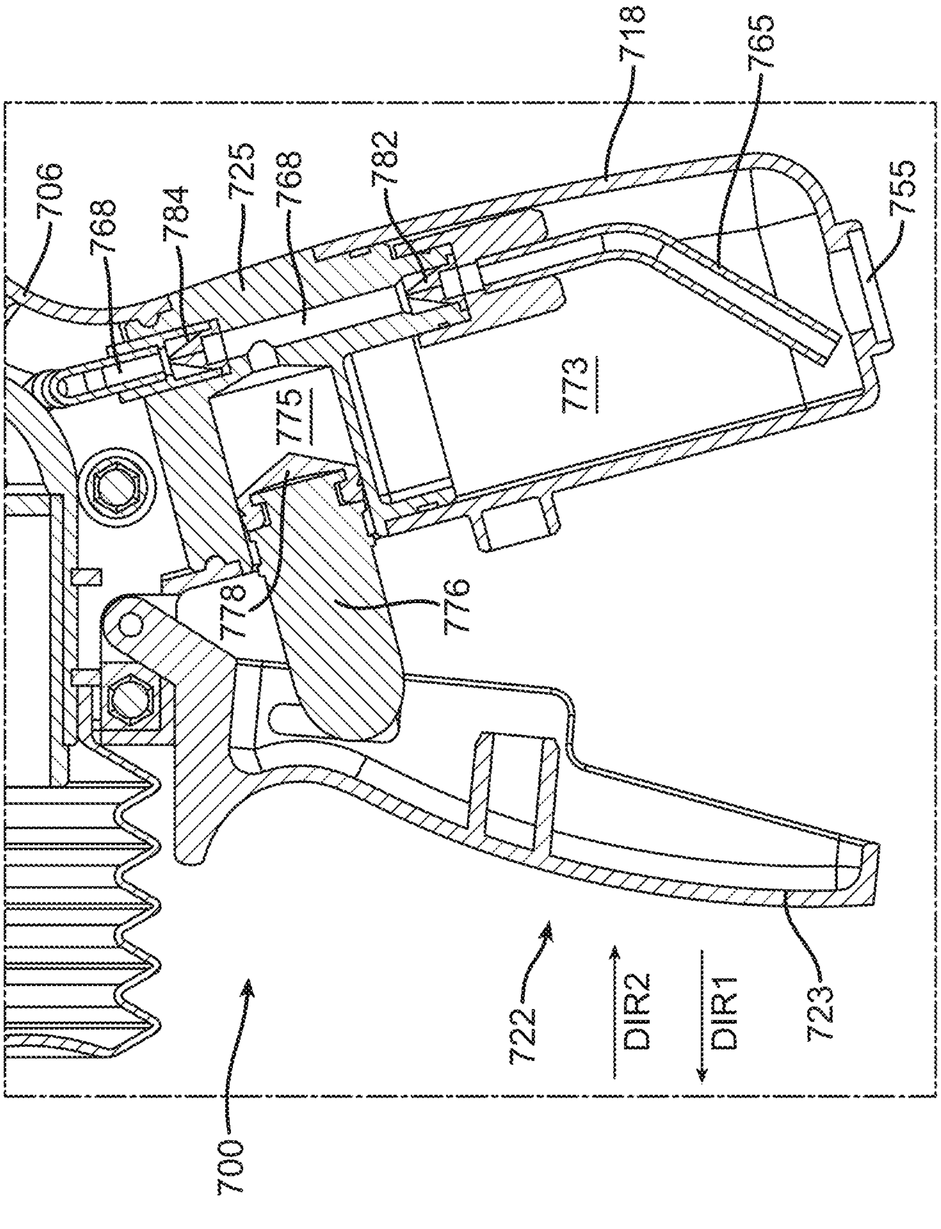
FIG. 29 is a cross-sectional view of a liquid delivery system of the combined powder and liquid delivery device shown in FIGS. 27A and 27B.

Referring to FIG. 29, in one embodiment, the liquid delivery system 722 may be utilized for drawing liquid from the liquid tank 718 and into the liquid delivery channel 768 of the combined powder and liquid delivery device, and for forcing the liquid to flow distally through the liquid delivery channel 768 for being dispensed from the distal end of the applicator tip of the combined powder and liquid delivery device 700. In one embodiment, the combined powder and liquid delivery device 700 preferably includes the device housing 706 having the handle 725 projecting from a lower end thereof. The combined powder and liquid delivery device 700 preferably include the liquid tank 718 having a liquid reservoir 773 that is adapted to store a liquid therein. In one embodiment, the liquid tank 718 preferably includes a valve 755 that may be utilized for filling the liquid chamber 775 with a liquid. In one embodiment, the valve 755 may also be utilized for drawing air into the liquid reservoir 773, such as when a vacuum is generated by the trigger 723 of the liquid delivery system 722.

In one embodiment, the liquid delivery system 722 may include a drainage tube 765 that is utilized for drawing liquid and/or air into the liquid delivery channel 768 of the combined powder and liquid delivery device 700.

In one embodiment, the combined powder and liquid delivery device 700 preferably includes an enclosure 774 (e.g., a barrel) that defines a liquid chamber 775. The combined powder and liquid delivery device 700 preferably include a plunger 776 having a proximal end coupled with the trigger 723 and a distal end that is coupled with a piston 778. The distal end of the plunger 776 and the piston 778 are disposed within the liquid chamber 775 of the barrel 774.

In one embodiment, the combined powder and liquid delivery device 700 preferably includes a first one-way valve 782 that is located downstream of the distal end of the drainage tube 765 and a second one-way valve 784 that is located downstream of the liquid chamber 775 of the barrel 774.

In one embodiment, the trigger 723 may be extended in the distal direction DIR1 for generating a vacuum within the liquid chamber 775 to draw the liquid from the liquid tank 718 and into the liquid chamber 775. A spring 727 (FIGS. 27A and 27B) may extend between the trigger 723 and the handle 725 for returning the trigger to the extended position shown in FIG. 29. In one embodiment, when the lower end of the trigger 723 is moving in the distal direction designated DIR1, the syringe plunger 776 and the piston 778 move away from the liquid delivery channel 768 for generating a vacuum within the liquid chamber 775. The vacuum draws the liquid from the liquid tank 718 into the liquid chamber 775. The liquid that is drawn from the liquid tank 718 preferably flows through the drainage tube 765 and through the first one-way valve 782, whereupon the liquid flows into and fills the liquid chamber 775 of the barrel 774.

In one embodiment, after the liquid chamber 775 has been at least partially filled with a liquid, the trigger 723 may be pulled proximally (DIR2), which forces the liquid from the liquid chamber 775 and into the liquid delivery channel 768 of the combined powder and liquid delivery device. As the trigger 723 is squeezed, the spring 727 (FIGS. 27A and 27B) is preferably compressed between the trigger 723 and the handle 725. As the trigger 723 is squeezed, the liquid is forced to flow downstream through the second one-way valve 784 and into a downstream segment of the liquid delivery channel 768 for being dispensed from a distal end of the applicator tip.

Figure 30:
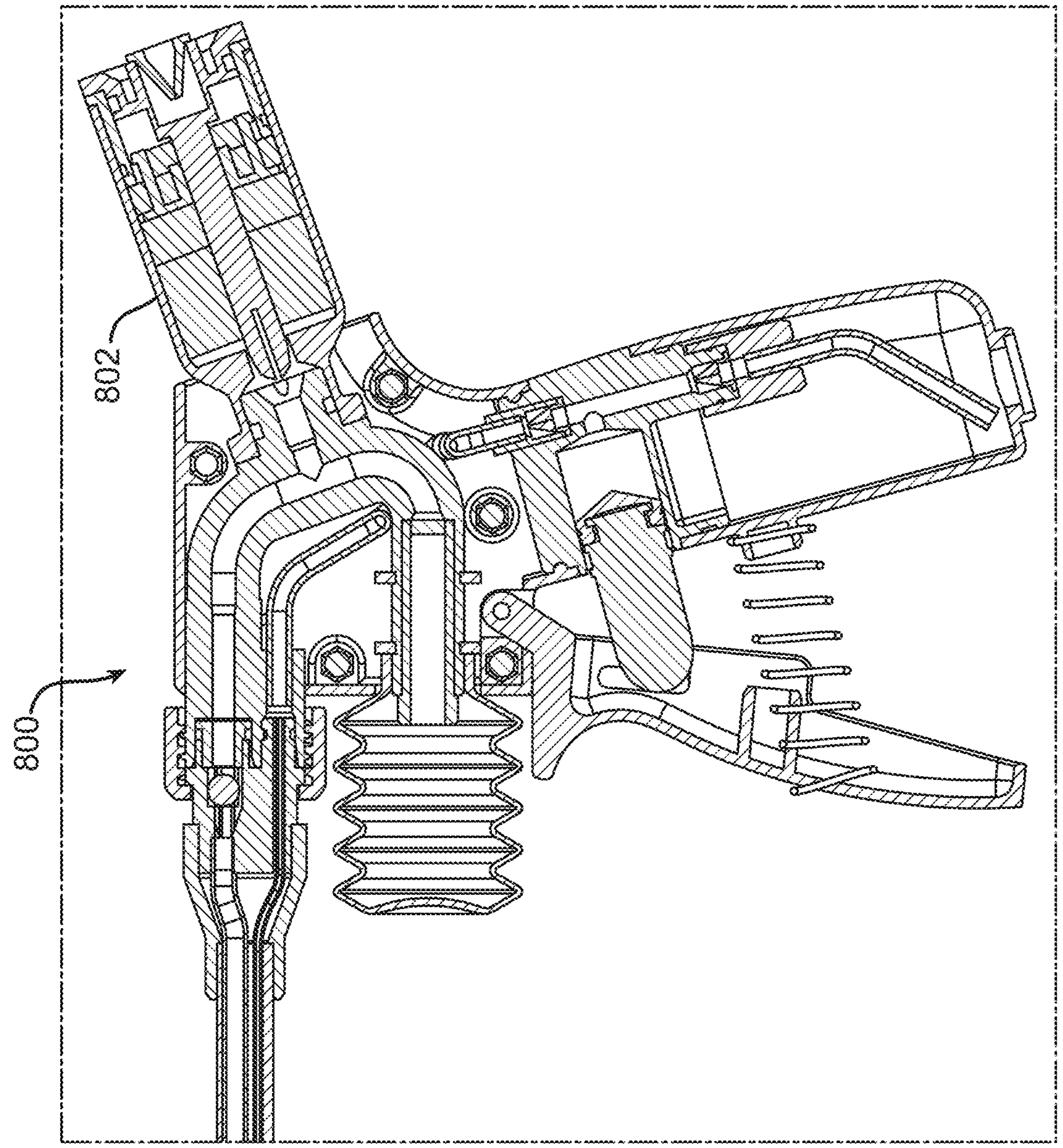
FIG. 30 is a cross-sectional view of a combined powder and liquid delivery device with a powder vial assembly connected to the powder and liquid delivery device, in accordance with one embodiment of the present patent application.

Referring to FIG. 30, in one embodiment, a combined powder and liquid delivery device 800, which may have structure and operate in a manner that is similar to the combined powder and liquid delivery device shown and described above in FIGS. 27A-29, preferably includes a powder vial assembly 802 that may be connected with the combined powder and liquid delivery device for supplying powder to the combined powder and liquid delivery device.

Figure 31A:
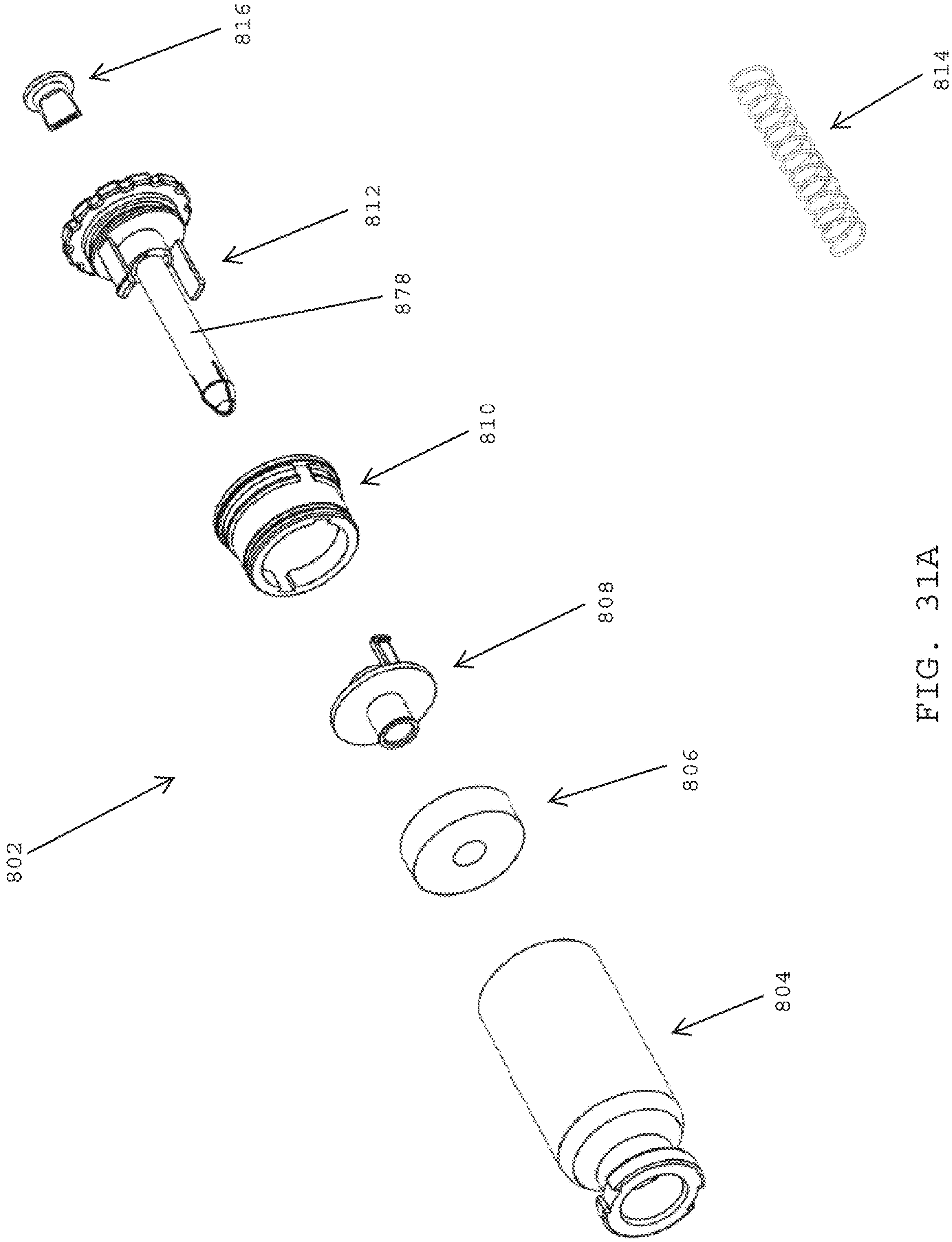
FIG. 31A is an exploded view of the powder vial assembly shown in FIG. 30 including a powder vial housing, a filter, a filter carriage, a fixed guide, a spring, an actuator assembly, and a one-way valve, in accordance with one embodiment of the present patent application.
Figure 31B:
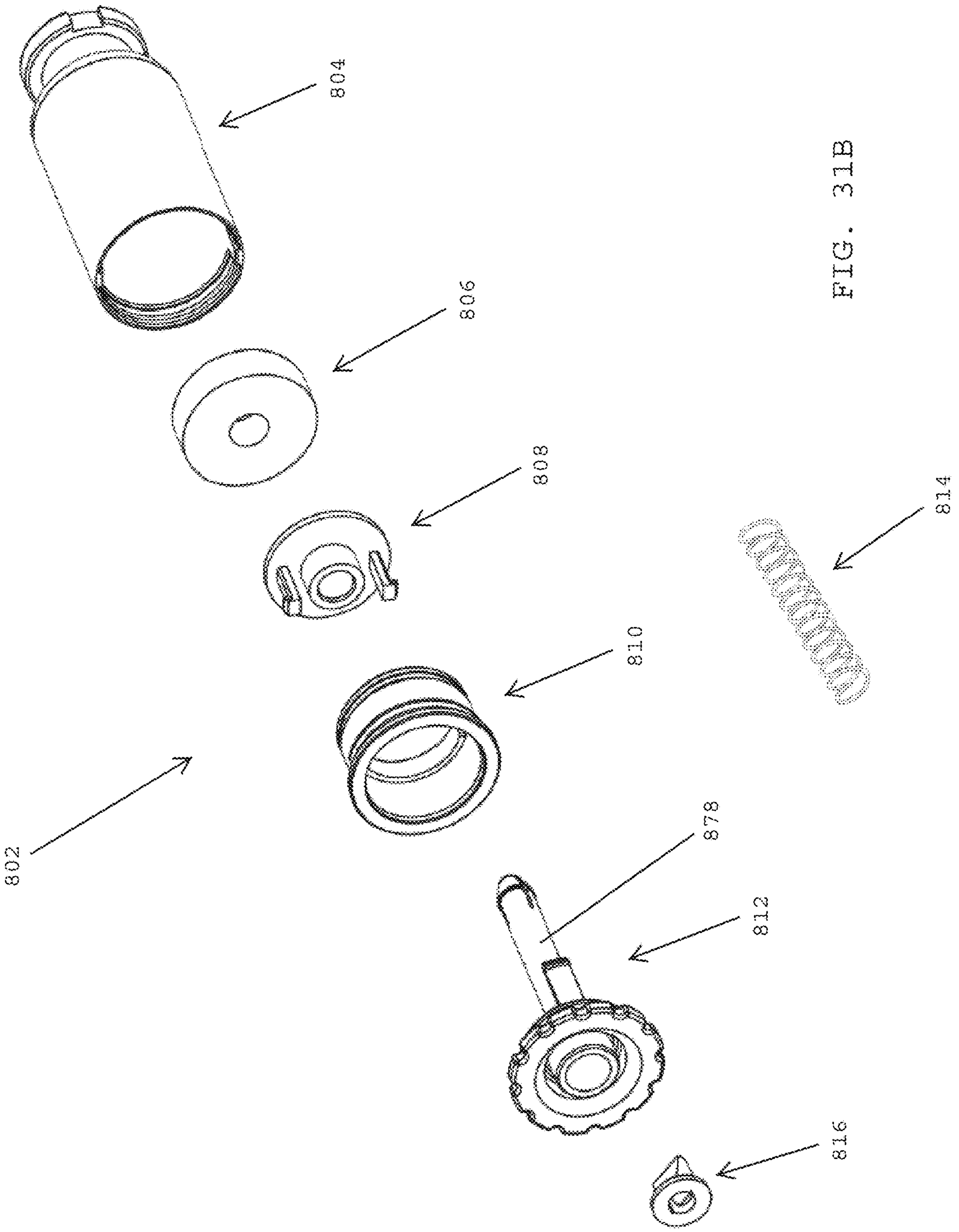
FIG. 31B is another exploded view of the powder vial assembly shown in FIGS. 30 and 31A.

Referring to FIGS. 31A and 31B, in one embodiment, the powder vial assembly 802 preferably includes a powder housing 804, a filter 806, a filter carriage 808, a fixed guide 810, an actuator assembly 812 having a filter carriage guide shaft 878, a spring 814 that extends between a proximal side of the filter carriage 808 and a distal side of the actuator 812, and a one-way valve 816.

In one embodiment, the filter 806 is mounted on the filter carriage 808, and the subassembly of the filter and filter carriage are mounted on the filter carriage guide shaft 878 of the actuator assembly.

Referring to FIGS. 32A-32D, in one embodiment, the powder housing 804 preferably has a proximal end 818 that surrounds a proximal opening 820 (FIG. 32C) and a distal end 822 having an attachment flange 824 that surrounds a powder dispensing opening 826.

Figure 32A:
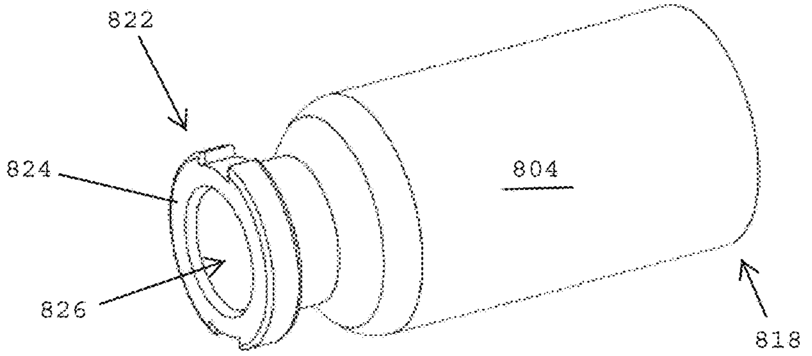
FIG. 32A is a perspective view of the powder vial housing shown in FIGS. 31A and 31B.
Figure 32B:
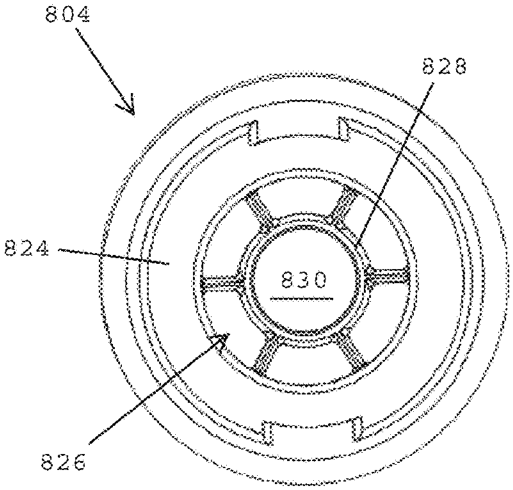
FIG. 32B is a distal end view of the powder vial housing shown in FIG. 32A.

Referring to FIG. 32B, in one embodiment, the connecting flange 824 is preferably adapted to be inserted into an opening of a combined powder and liquid delivery device 800 (FIG. 30) for securing the distal end 822 of the powder housing 804 to the combined powder and liquid delivery device. The connecting flange 824 surrounds the powder dispensing opening 826 for enabling powder stored within a powder chamber 824 of the powder housing 804 to be directed into the combined powder and liquid delivery device 800 (FIG. 30).

Figure 32C:
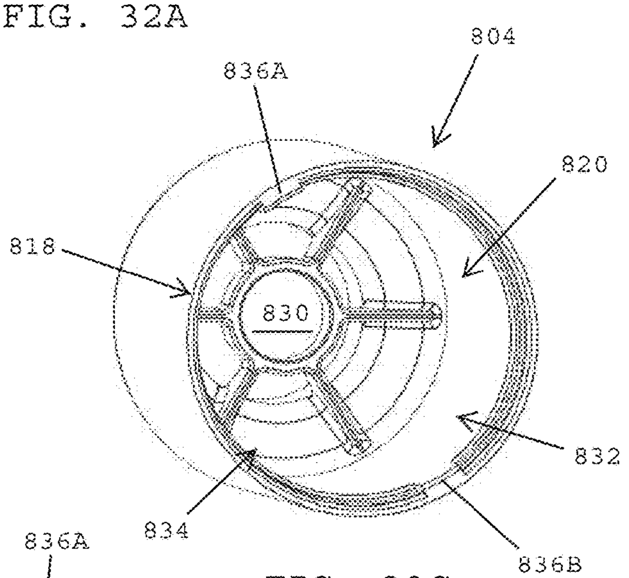
FIG. 32C is a perspective view of a proximal end of the powder vial housing shown in FIGS. 32A and 32B.
Figure 32D:
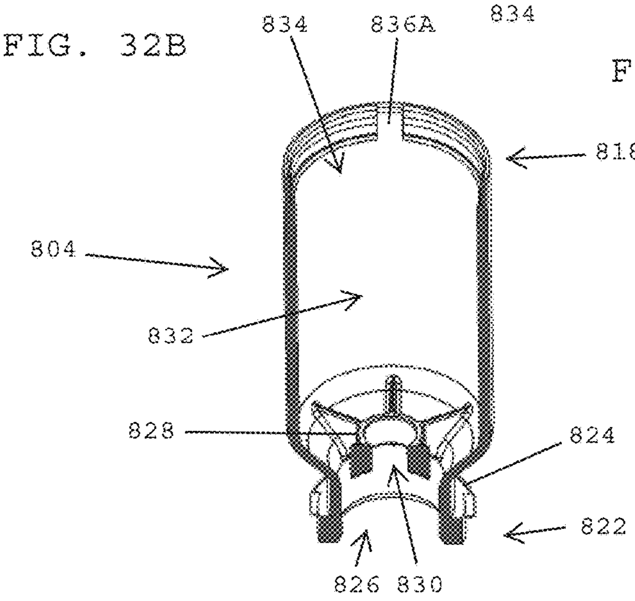
FIG. 32D is a cross-sectional view of the powder vial housing shown in FIGS. 32A-32C.

Referring to FIGS. 32B-32D, in one embodiment, the powder housing 804 preferably includes a support 828 that is located adjacent the powder dispensing opening 826 at the distal end 822 of the powder housing 804. The support 828 has a central opening 830 that is adapted to receive the filter carriage guide shaft 878 of the actuator assembly 812 (FIG. 31A) as will be described in more detail herein.

Referring to FIGS. 32C and 32D, in one embodiment, the powder housing 804 surrounds the powder chamber 832, which is adapted to be filled with a powder that may be dispensed from the powder dispensing opening 826 of the powder vial assembly.

In one embodiment, the proximal end 818 of the powder housing 804 preferably includes a proximal opening 834 that provides access to the powder chamber 832. In one embodiment, the proximal end 818 of the powder housing 804 includes a pair of alignment tabs 836A, 836B that are adapted to engage a corresponding pair of alignment notches formed in an outer surface of the fixed guide 810 (FIG. 31A), as will be described in more detail herein.

Figure 33A:
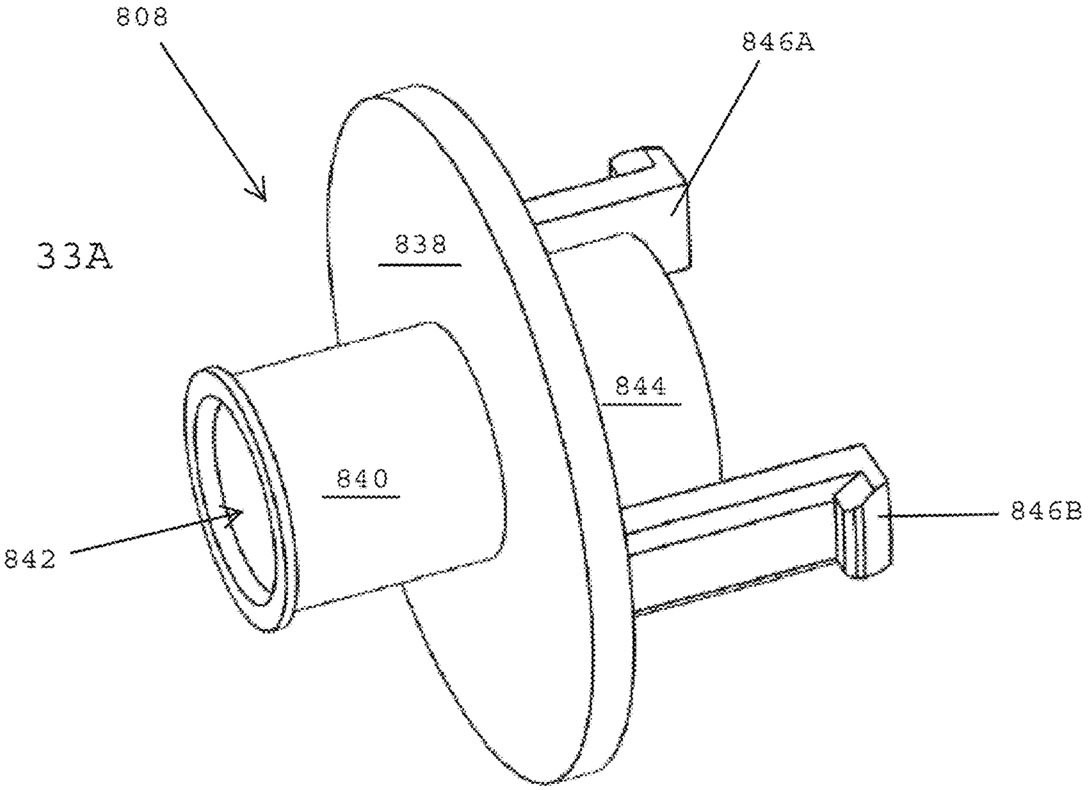
FIG. 33A is a perspective view of a distal end of the filter carriage shown in FIGS. 31A and 31B.
Figure 33B:
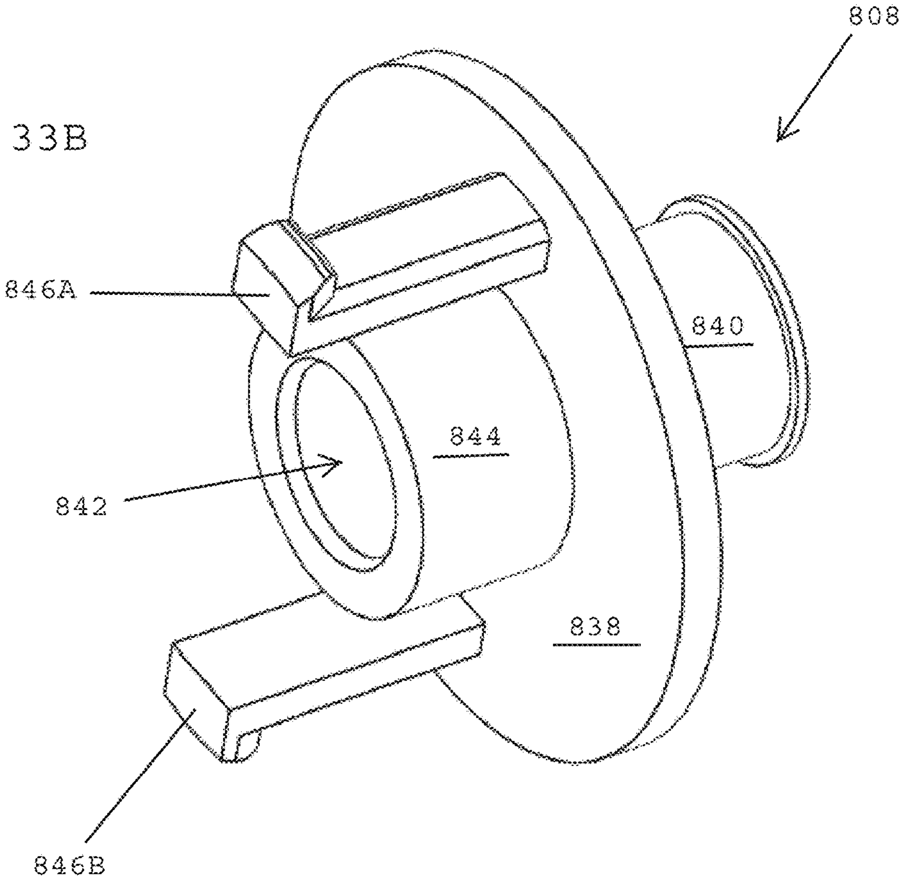
FIG. 33B is a perspective view of a proximal end of the filter carriage shown in FIGS. 31A and 31B.

Referring to FIGS. 33A and 33B, in one embodiment, the filter carriage 808 is adapted to carry the filter 806 (FIG. 31A). The filter carriage 808 preferably includes a filter support base 838 that engages a major face of the filter and a central hub 840 that preferably passes through a central opening of the filter for securing the filter onto the filter carriage 808. The central hub 840 preferably surrounds a central opening 842 that extends through the center of the filter carriage 808 for enabling the filter carriage to be mounted onto the filter carriage guide shaft 878 of the actuator assembly 812 (FIG. 31A).

In one embodiment, the filter carriage 808 preferably includes a spring hub 844 that projects proximally from the filter support base 838, which is adapted to engage a distal end of the compression spring 814 (FIG. 31A). The central opening 842 that extends through the filter carriage 808 also passes through the filter support base 838 and the spring hub 844 so that the filter carriage 808 may be mounted on the filter carriage guide shaft 878 (FIG. 31A) of the actuator assembly 812.

In one embodiment, the filter carriage 808 preferably includes a pair of hooks 846A, 846B that are used for locking and releasing the filter carriage 808 with the fixed guide 810 (FIG. 31A), as will be described in more detail herein.

Figure 34A:
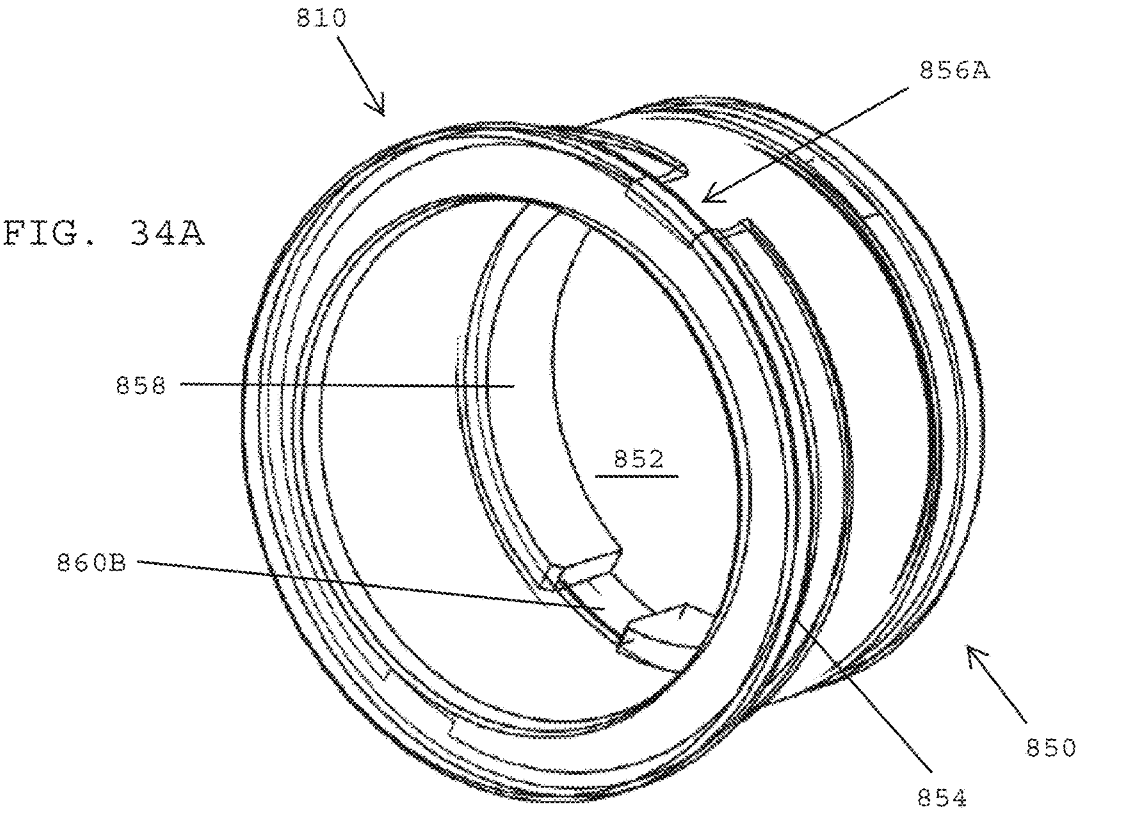
FIG. 34A is a perspective view of a proximal end of the fixed guide shown in FIGS. 31A and 31B.
Figure 34B:
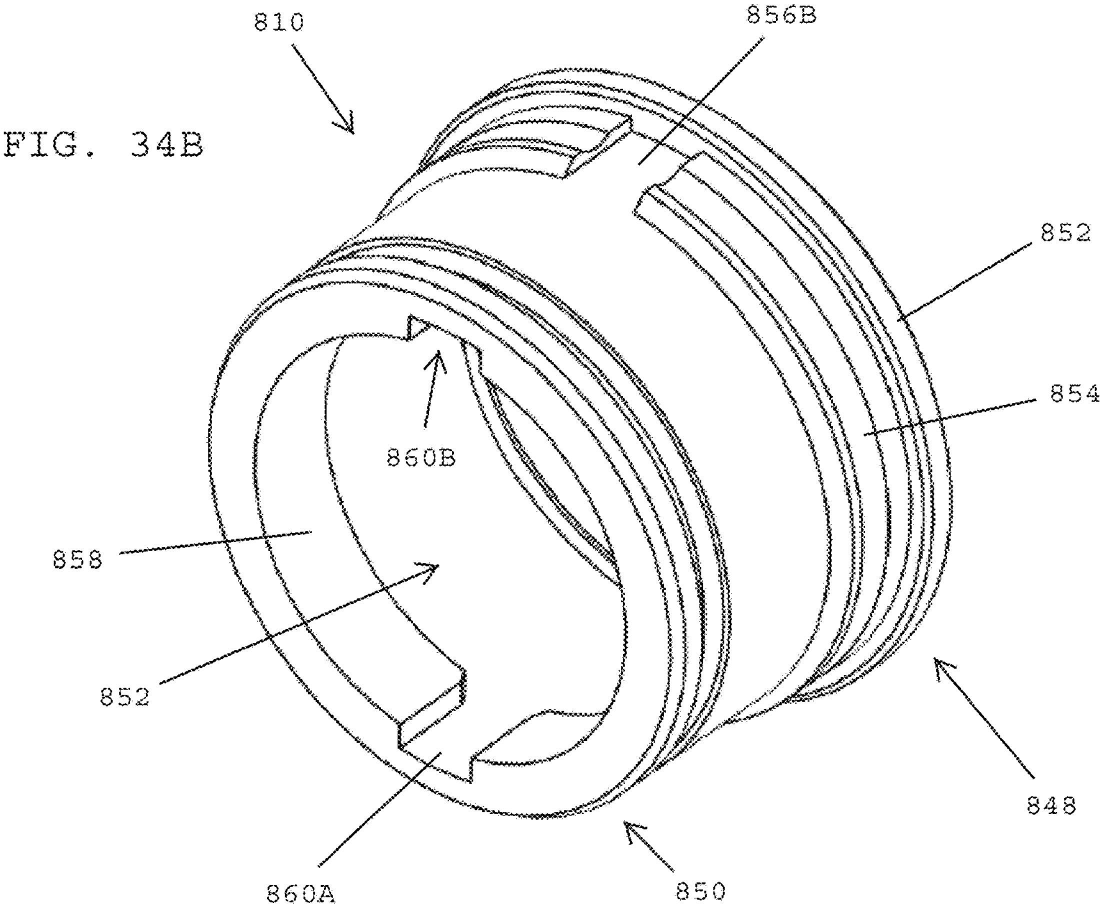
FIG. 34B is a perspective view of a distal end of the fixed guide shown in FIGS. 31A and 31B.

Referring to FIGS. 34A and 34B, in one embodiment, the fixed guide 810 preferably has a proximal end 848, a distal end 850 and a central opening 852 that extends from the proximal end 848 to the distal end 850.

In one embodiment, the proximal end 848 of the fixed guide 810 desirably includes an annular flange 854 that is adapted to abut against the proximal end 818 of the powder housing 804 (FIG. 32D) for securing the fixed guide 810 to the proximal end of the powder housing. In one embodiment, the fixed guide 810 preferably includes an annular band 854 that is adapted to engage an interior surface at the proximal end of the powder housing for forming an air-tight fit between the fixed guide 810 and the proximal opening at the proximal end of the powder housing 804 (FIG. 32D). The annular band 854 preferably forms an air-tight fit with the proximal end of the powder housing and prevents the fixed guide 810 from moving axially relative to the longitudinal axis of the powder housing.

In one embodiment, the fixed guide 810 preferably includes a pair of alignment notches 856A, 856B that extend through the band 854. The pair of alignment notches 856A, 856B preferably mesh with the respective alignment tabs 836A, 836B at the proximal end 818 of the powder housing 804 (FIGS. 32C and 32D) for preventing the fixed guide 810 from rotating relative to the powder housing.

Thus, in one embodiment, when the fixed guide 810 is assembled with the proximal end of the powder housing, the fixed guide will remain stationary relative to the powder housing and will not more axially or rotate relative to the powder housing.

In one embodiment, the distal end 850 of the fixed guide 810 preferably includes a step 858, which may also be referred to as a stop, that is used for initially locking the filter carriage 808 (FIGS. 33A and 33B) to the fixed guide 810. In one embodiment, the fixed guide 810 preferably includes a pair of release slots 860A, 860B that are formed in the step 858 for enabling the hooks 846A, 846B of the filter carriage 808 to be released from the fixed guide 810. In one embodiment, the hooks 846A, 846B (FIG. 33B) of the filter carriage initially engage the step 858 of the fixed guide 810 for preventing the filter carriage and the filter from moving axially toward the distal end of the powder housing. In one embodiment, the hooks may be rotated relative to the fixed guide 810 so that the hooks are aligned with the release slots 860A, 860B of the fixed guide, whereupon the filter carriage and the filter are free to move axially relative to the fixed guide 810.

In one embodiment, when the hooks of the filter carriage are aligned with the release slots 860A, 860B of the fixed guide 810, the compression spring 814 (FIG. 31A) will urge the filter/filter carriage subassembly to slide distally over the filter carriage guide shaft 878 (FIG. 31A).

Figure 35A:
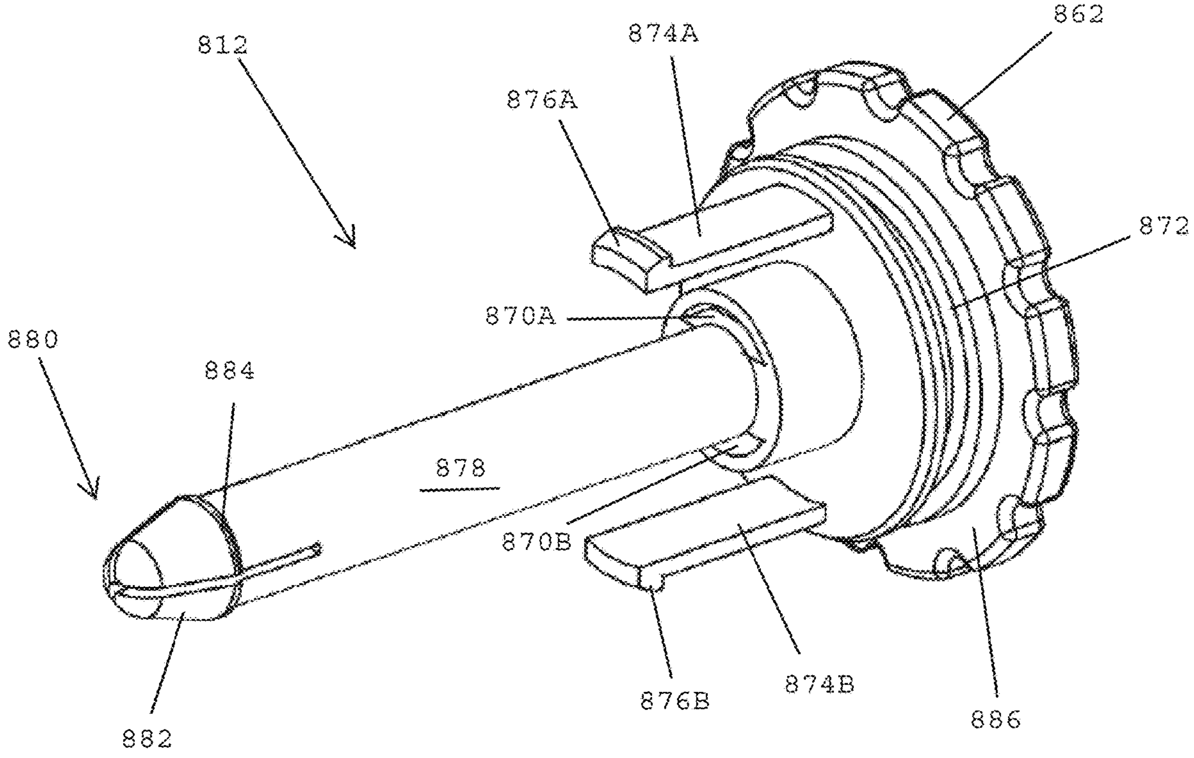
FIG. 35A is a perspective view of a distal end of the actuator assembly shown in FIGS. 31A and 31B.
Figure 35B:
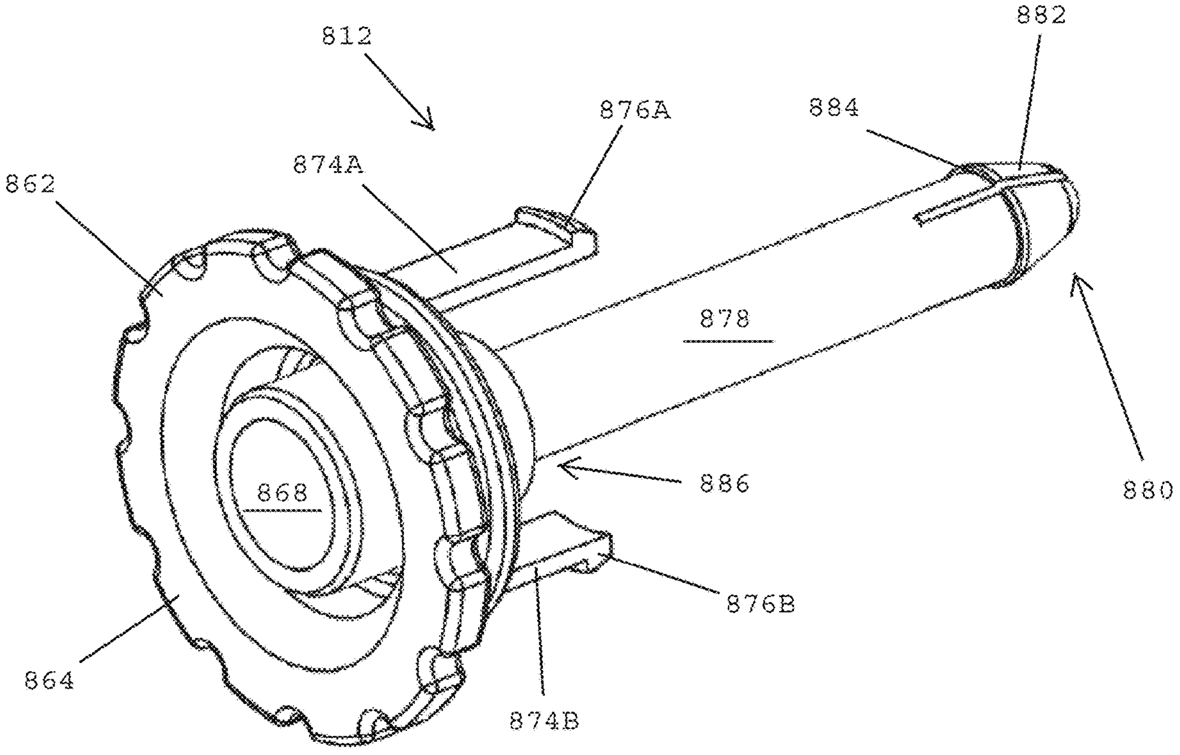
FIG. 35B is a perspective view of a proximal end of the actuator assembly shown in FIGS. 31A and 31B.

Referring to FIGS. 35A and 35B, in one embodiment, the actuator assembly 812 of the powder vial assembly 802 (FIG. 30) preferably includes a rotatable actuating knob 862 having a proximal face 864 and a distal face 886 that is adapted to abut against the proximal end 848 of the fixed guide 810 (FIGS. 35A and 35B). The actuator assembly 812 preferably includes an air inlet opening 868 that passes through the rotatable actuating knob 862. The air inlet opening 868 is adapted to receive the one-way valve 816 (FIG. 31A) for allowing air to be drawn into the powder vial assembly. The air inlet opening 868 is preferably in communication with air channels 870A, 870B that are located downstream from the distal face 866 of the rotatable actuating knob 862. The air channels 870A, 870B preferably direct the air that passes through the air inlet opening 868 into an interior region of the powder vial assembly.

In one embodiment, the actuator assembly 812 preferably includes a sealing band 872 that is adapted to engage an inner surface of the fixed guide 810 at the proximal end 848 of the fixed guide (FIGS. 34A and 34B) for forming an air-tight fit between the actuator assembly 812 and the proximal end of the fixed guide 810. The actuator assembly 812 may be rotated relative to the fixed guide while maintaining the air-tight seal between the actuator assembly and the fixed guide.

In one embodiment, the actuator assembly 812 preferably includes a pair of actuating legs 874A, 874B that project distally beyond the distal face 866 of the rotatable actuating knob 862. In one embodiment, the distal ends of the actuating legs 874A, 874B have actuating leg hooks 876A, 876B, respectively, that are adapted to engage the distal end 850 of the fixed guide 810 (FIG. 34B) for securing the actuating assembly 812 to the fixed guide 810.

In one embodiment, as the rotatable actuating knob 862 is rotated, the actuating legs 874A, 874B rotate simultaneously with the rotatable actuating knob.

In one embodiment, the actuator assembly 812 preferably includes the filter carriage guide shaft 878 that projects distally beyond the distal ends of the actuating legs 874A, 874B. In one embodiment, the subassembly of the filter 806 and the filter carriage 808 (FIG. 31B) may be mounted on the filter carriage guide shaft 878 of the actuator assembly 812. The filter/filter carriage subassembly are adapted to slide over and along the length of the filter carriage guide shaft 878.

In one embodiment, the distal end 880 of the filter carriage guide shaft 878 preferably includes a compressible structure 882 that may be compressed for installing the filter/filter carriage subassembly onto the filter carriage guide shaft 878. In one embodiment, the filter carriage guide shaft 878 desirably includes an annular stop 884 located adjacent the distal end of the guide shaft that holds the filter/filter carriage subassembly on the guide shaft and prevents the filter/filter carriage subassembly from sliding off the distal end 880 of the filter carriage guide shaft 878.

In one embodiment, the pair of air inlet channels 870A, 870B are located adjacent the proximal end 886 of the filter carriage guide shaft 878. In one embodiment, the pair of air inlet channels 870A, 870B guide the air that enters into the powder housing 804 (FIG. 31A) to flow around the outer surface of the filter carriage guide shaft 878 of the actuator assembly.

Referring to FIGS. 31A-35B, in one embodiment, when the rotatable actuating knob 862 of the actuator assembly 812 is rotated, the actuating legs 874A, 874B rotate simultaneously with the rotatable actuating knob 862. In one embodiment, as the actuating legs 874A, 874B rotate about the longitudinal axis of the filter carriage guide shaft 878, the actuating legs engage the hooks 846A, 846B of the filter carriage 808 (FIGS. 33A and 33B) for rotating the filter carriage about the longitudinal axis of the filter carriage guide shaft 878. In one embodiment, as the hooks 846A, 846B of the filter carriage rotate about the longitudinal axis of the filter carriage guide shaft 878, the hooks 846A, 846B rotate into alignment with the release notches 860A, 860B (FIGS. 34A and 34B) located at the distal end 850 of the fixed guide 810 for releasing the filter carriage 808 from its engagement with the fixed guide 810. Upon release of the filter carriage 808, the spring 814 (FIG. 31B) that is under compression pushes the filter carriage 808 and the filter 806 to move toward the distal end 880 of the filter carriage guide shaft 878.

Figure 36A:
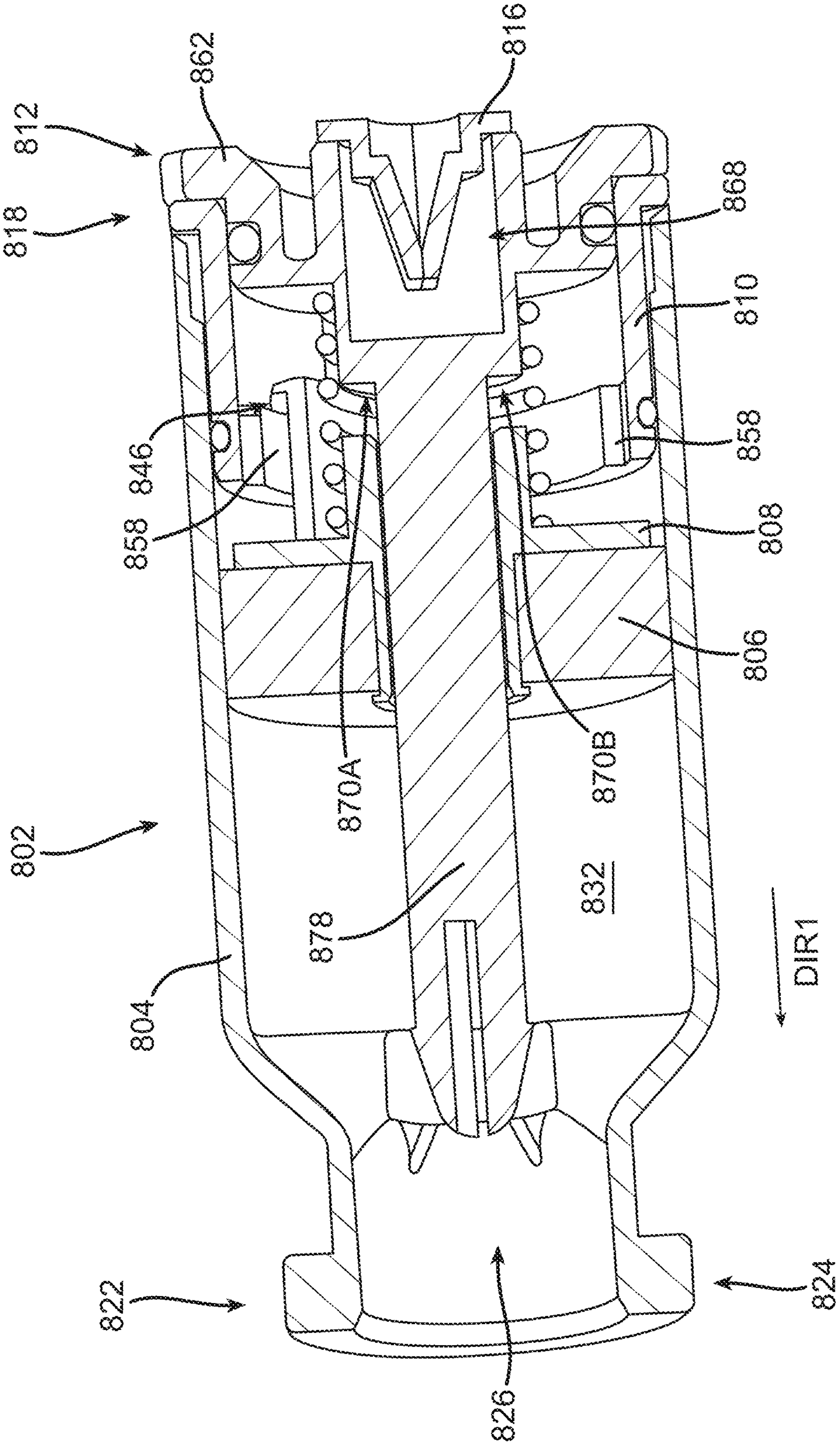
FIG. 36A is a cross-sectional view of a powder vial assembly of a powder and liquid delivery device, in accordance with one embodiment of the present patent application.

Referring to FIG. 36A, in one embodiment, the powder vial assembly 802 preferably includes the powder housing 804 that contains the powder chamber 832. The powder housing 804 preferably has a proximal end 818, and a distal end 822 having the connecting flange 824 that is utilized for securing the distal end 822 of the powder housing 804 to a combined powder and liquid delivery device 800 (FIG. 30). The powder vial assembly 802 preferably includes the powder dispensing opening 826 located at the distal end 822 of the powder housing 804.

The powder vial assembly 802 preferably includes the actuator assembly 812 that is secured to the fixed guide 810 adjacent the proximal end 818 of the powder housing 804. The actuator assembly 812 preferably includes the filter carriage guide shaft 878 that supports the subassembly of the filter 806 and the filter carriage 808, which are adapted to slide over the filter carriage guide shaft 878.

In one embodiment, the one-way valve 816 is disposed within the air inlet opening 868 (FIG. 35B) that extends through the rotatable actuating knob 862 of the actuator assembly 812. In one embodiment, the hooks 846 of the filter carriage 808 engage the step 858 (FIG. 34B) of the fixed guide 810 for preventing the filter carriage 808 and the filter 806 from sliding in the distal direction DIR1 toward the distal end 822 of the powder housing 804.

Figure 36B:
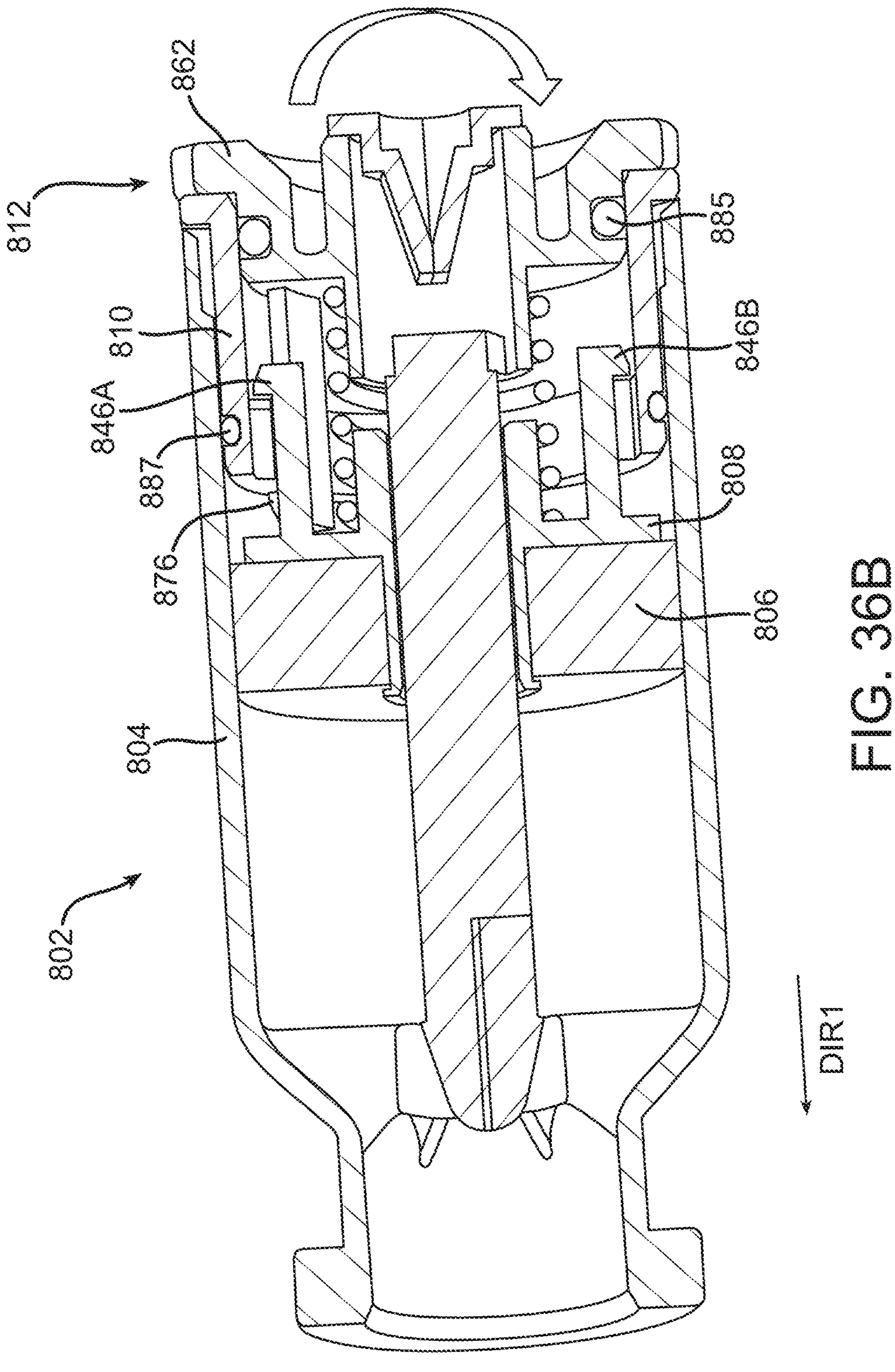
FIG. 36B is another cross-sectional view of the powder vial assembly shown in FIG. 36A.

Referring to FIG. 36B, in one embodiment, the hooks 876 of the actuator assembly 812 couple the actuator assembly 812 with the fixed guide 810. A first O-ring seal 885 preferably forms an air-tight seal between the actuator assembly 812 and the fixed guide 810. A second O-ring seal 887 preferably forms an air-tight seal between an outer surface of the fixed guide 810 and an inner surface of the powder housing 804 of the powder vial assembly 802.

In one embodiment, the rotatable actuating knob 862 of the actuator assembly 812 may be rotated for rotating the actuating legs 874A, 874B (FIG. 35A), which, in turn, engage the hooks 846A, 846B of the filter cartridge 808 for aligning the hooks 846A, 846B with the release slots 860A, 860B (FIGS. 34A and 34B) of the step 858 of the fixed guide 810 to release the filter carriage 808 from the fixed guide 810. At this stage, the subassembly of the filter 806 and the filter carriage 808 are free to slide in the distal direction DIR1 over the filter carriage guide shaft 878.

Figure 36C:
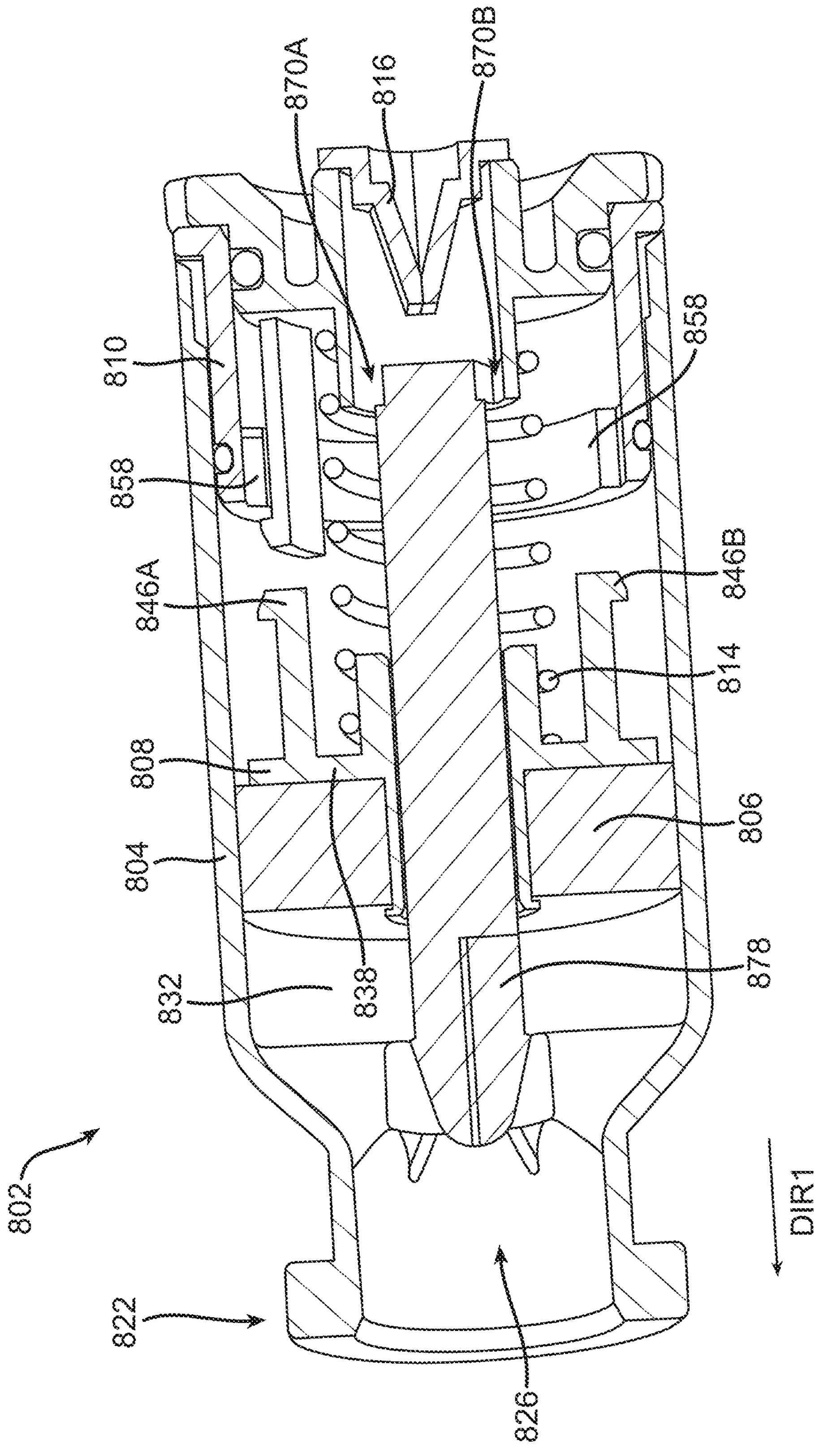
FIG. 36C is another cross-sectional view of the powder vial assembly shown in FIG. 36B.

Referring to FIGS. 36B and 36C, in one embodiment, once the hooks 846A, 846B of the filter carriage 808 have been released from the step 858 of the fixed guide 810, the compression spring 814 releases energy to push the filter carriage 808 and the filter 806 in the distal direction DIR1. At this stage, the filter/filter carriage subassembly slides distally over the filter carriage guide shaft 878 for forcing a dose of powder from the powder chamber 832. The dose of powder preferably passes through the powder dispensing opening 826 located at the distal end 822 of the powder housing 804 of the powder vial assembly.

In one embodiment, ambient air may be drawn through the one-way valve 816 for being directed through the pair of air channels 870A, 870B. In one embodiment, the inflowing air preferably flows distally around the outer surface of the filter carriage guide shaft 878. The air provides positive pressure for forcing the powder within the powder chamber 832 to flow toward the powder dispensing opening 826 located at the distal end 822 of the powder housing 804.

The spring 814 applies a continuous force on the filter support plate 838 of the filter carriage 808. Once the filter carriage 808 guide has been released from the fixed guide 810, as each dose of powder is dispensed from the powder chamber 832, a void will form in the powder chamber, whereupon the compression spring 814 applies a force on the filter carriage that urges the filter carriage 808 to move distally (e.g., slide distally over the filter carriage guide shaft in the direction DIR1) for taking up any excess space that is created by removing a dose of powder from the powder chamber 832.

In one embodiment, as a dose of powder is drawn out of the powder dispensing opening 826 located that the distal end 822 of the powder housing 804, the spring 814 presses the filter carriage 808 and the filter 806 toward the distal end 822 of the powder housing 804 to take up any excess space that was created upon expressing a dose of powder. The action of the compression spring 814 continues as each dose of powder is dispensed from the powder housing 804.

The powder vial assembly 802 disclosed herein provides numerous advantages over the prior art including but not limited to the ability to store the powder separate and apart from a combined powder and liquid delivery device for maintaining the powder in an optimal state and/or condition.

In one embodiment, the powder vial assembly is specially designed to assist feeding powder into the powder delivery channel. In one embodiment, the powder vial assembly may comprise a spring/filter assembly that is configured to push the powder into a powder dispensing opening of a powder housing. In one embodiment, the powder vial assembly may comprise an air valve at a proximal end of the powder vial assembly that allows air to enter the powder vial assembly when a dose of powder is sucked into the powder delivery channel.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A combined powder and liquid delivery device comprising:

a delivery device housing having a powder chamber and a liquid chamber, wherein said powder and liquid chambers are isolated from one another;

an applicator tip having a powder delivery channel extending between a proximal end and a distal end of said applicator tip that is in fluid communication with said powder chamber;

said applicator tip having a liquid delivery channel that extends from the proximal end to the distal end of said applicator tip that is in fluid communication with said liquid chamber;

a powder inlet port in fluid communication with said powder chamber;

a liquid inlet port in fluid communication with said liquid chamber;

a powder delivery system in fluid communication with said powder inlet port, said powder chamber, and said powder delivery channel;

a liquid delivery system in fluid communication with said liquid inlet port, said liquid chamber, and said liquid delivery channel, and further comprising a one-way valve located downstream of said powder chamber and being in fluid communication with said powder delivery system.

2. The combined powder and liquid delivery system as claimed in claim 1, further comprising a dual-lumen powder and liquid connector secured to the distal end of said applicator tip, wherein said dual-lumen powder and liquid connector has a powder exit opening in fluid communication with said powder delivery channel, and a liquid spray opening in fluid communication with said liquid delivery channel, optionally, said powder exit opening and said liquid spray opening being staggered from one another wherein said liquid spray opening is located downstream of said powder exit opening for preventing moisture in said liquid delivery channel from entering said powder delivery channel.

3. The combined powder and liquid delivery device as claimed in claim 1, further comprising:

a powder vial connector secured to said delivery device housing, said powder vial connector including said powder inlet port;

a liquid vial connector secured to said delivery device housing, said liquid vial connector including said liquid inlet port.

4. The combined powder and liquid delivery device as claimed in claim 3, further comprising:

a powder disposed inside said powder vial connector; and a liquid disposed inside said liquid vial connector.

5. The combined powder and liquid delivery system as claimed in claim 4, wherein said liquid delivery system is moveable between a depressed configuration and an extended configuration, wherein when moving from the depressed configuration to the extended configuration said liquid delivery system generates a vacuum within said liquid chamber for drawing a dose of liquid from said liquid vial connector into said liquid chamber, and wherein when moving from the extended configuration to the depressed configuration said liquid delivery system generates positive pressure within said liquid chamber for expressing said dose of liquid from said liquid chamber and forcing said liquid to flow into said liquid delivery channel.

6. The combined powder and liquid delivery system as claimed in claim 5, wherein said liquid delivery system further comprising a second air inlet in fluid communication with said liquid chamber and a one-way valve disposed in said second air inlet that enables ambient air to be drawn into said liquid chamber as said liquid delivery system moves from the depressed configuration to the extended configuration.

7. The combined powder and liquid delivery system as claimed in claim 6, wherein said liquid delivery system further comprises a first one way valve disposed within said liquid inlet port that enables the liquid to be drawn from said liquid vial connector into said liquid chamber of said delivery device housing, and a second one way valve disposed within said liquid delivery channel and downstream of said first one way valve disposed within in said liquid inlet port that enables the liquid in said liquid chamber to flow downstream into said liquid delivery channel.

8. The combined powder and liquid delivery system as claimed in claim 4, wherein said powder delivery system is moveable between a depressed configuration and an extended configuration, wherein when moving from the depressed configuration to the extended configuration said powder delivery system generates a vacuum within said powder chamber for drawing a dose of powder from said powder vial connector into said powder chamber, and wherein when moving from the extended configuration to the depressed configuration said powder delivery system generates positive pressure within said powder chamber for expressing said dose of powder from said powder chamber and forcing said powder to flow into said powder delivery channel.

9. The combined powder and liquid delivery system as claimed in claim 8, wherein said powder delivery system further comprises a first air inlet in fluid communication with said powder chamber and a one-way valve disposed in said first air inlet that enables ambient air to be drawn into said powder chamber as said powder delivery system moves from the depressed configuration to the extended configuration.

10. The combined powder and liquid delivery device as claimed in claim 8, wherein said powder delivery system comprises a bellows assembly having threads for releasably securing said bellows assembly to a proximal end of said delivery device housing, wherein said bellows assembly is configured for being unscrewed from said delivery device housing for enabling powder to be loaded into said powder chamber, optionally, the proximal end of said delivery device housing having an access opening for providing access to said powder chamber wherein said access opening has internal threads that are configured to mesh with the threads of said bellows assembly for securing said bellows assembly to the proximal end of said delivery device housing.

11. The combined powder and liquid delivery device as claimed in claim 10, further comprising:

said powder chamber being surrounded by a tube-shaped wall having a closed distal end, wherein said closed distal end has a distal exit opening formed therein that provides fluid communication between said powder chamber and said powder delivery channel;

an anti-compaction wall disposed inside said powder chamber that is spaced away from said closed distal end of said tube-shaped wall, wherein said anti-compaction wall is located between said closed distal end of said tube-shaped wall and a proximal end of said powder chamber, and wherein said anti-compaction wall has an outer perimeter that is spaced away from an inner surface of said tube-shaped wall that surrounds said powder chamber.

12. The combined powder and liquid delivery system as claimed in claim 11, wherein said bellows assembly comprises:

an end cap disposed in said access opening of said delivery device housing;

a bellows projecting from a proximal face of said end cap;

an elongated shaft projecting from a distal face of said end cap, wherein said distal end of said elongated shaft is disposed inside said powder chamber and opposes a proximal face of said anti-compaction wall;

a filter holder mounted on said elongated shaft between said end cap and the distal end of said elongated shaft;

a filter mounted on said filter holder between said filter holder and the distal end of said elongated shaft;

a compression spring extending between said bellows and said filter holder, said compression spring having a proximal end disposed inside said bellows and a distal end located adjacent a proximal face of said filter holder.

13. The combined powder and liquid delivery system as claimed in claim 12, wherein when said bellows is depressed toward the distal end of said powder chamber, said compression spring is compressed so that the distal end of said compression spring urges said filter holder and said filter to move closer to said anti-compaction wall, optionally said filter holder and said filter being configured to move simultaneously with one another within said powder chamber wherein said filter holder and said filter have respective outer diameters that match an inner diameter of said tube-shaped wall that surrounds said powder chamber for forming an air-tight seal between the respective outer diameters of said filter holder and said filter and the inner surface of said tube-shaped wall that surrounds said powder chamber.

* * * * *